United States Patent [19]

Kawata et al.

[11] Patent Number: 5,397,693
[45] Date of Patent: Mar. 14, 1995

[54] SILVER HALIDE PHOTOGRAPHIC LIGHT-SENSITIVE MATERIAL

[75] Inventors: Ken Kawata; Tadashi Ikeda, both of Kanagawa, Japan

[73] Assignee: Fuji Photo Film Co., Ltd., Kanagawa, Japan

[21] Appl. No.: 44,061

[22] Filed: Apr. 8, 1993

[30] Foreign Application Priority Data

Apr. 9, 1992 [JP] Japan .................................. 4-116809
Sep. 2, 1992 [JP] Japan .................................. 4-259029

[51] Int. Cl.$^6$ ............................................... G03C 1/08
[52] U.S. Cl. ..................................... 430/581; 430/582; 430/583; 430/584; 430/585; 430/586; 430/587; 430/588; 430/576; 430/577
[58] Field of Search ............... 430/581, 582, 583–588, 430/576, 577

[56] References Cited

U.S. PATENT DOCUMENTS 2,231,658 2/1941 Brooker et al. .
3,904,015 11/1972 Brooker ............................ 430/581

FOREIGN PATENT DOCUMENTS 0298158 1/1989 European Pat. Off. .
0474047 3/1992 European Pat. Off. .
700781 1/1941 Germany .
11 59 577 12/1963 Germany .
34 02 480 8/1984 Germany .
36 22 256 1/1987 Germany .

*Primary Examiner*—Thorl Chea
*Attorney, Agent, or Firm*—Sughrue, Mion, Zinn, Macpeak & Seas

[57] ABSTRACT

A silver halide photographic light-sensitive material contains a methine compound represented by the following formula:

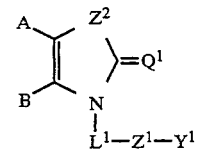

wherein $Y^1$ is a group which is cleavable by a nucleophile; $Z^1$ is —O—, —S—, or other; $Z^2$ is —O—, —S—, —CR$^3$R$^4$ (wherein each of R$^3$ and R$^4$ is alkyl or other), or other; A and B are each independently hydrogen, halogen, alkyl, aryl or a heterocyclic group; A and B may be linked to each other to form an unsaturated aliphatic ring, an aromatic ring or a heterocyclic ring; and $Q^1$ is a methine or polymethine group which may have a heterocyclic group. A novel methine compound is also disclosed.

2 Claims, No Drawings

SILVER HALIDE PHOTOGRAPHIC LIGHT-SENSITIVE MATERIAL

FIELD OF THE INVENTION

The present invention relates to silver halide photographic light-sensitive materials and further relates to a novel methine compound which is useful for preparing the silver halide photographic light-sensitive materials.

BACKGROUND OF THE INVENTION

In an image formation process of a silver halide photographic light-sensitive material, it is recently desired to reduce the processing time. However, if the time is reduced, there is not given sufficient time for completing decoloration of unnecessary dyes (which are required in the exposure step), sensitizing dyes or de-sensitizing dyes contained in the light-sensitive material, or removing those dyes from the light-sensitive material. Therefore, the obtgained image unfavorably has a residual color derived from those dyes.

In order to solve these problems, there has been proposed a method of employing water-soluble dyes to increase the decoloring efficiency. Further, a solution for processing for the decoloring have been studied to increase the decoloring efficiency. For example, there are known as methods of reducing the residual color: (1) a method of adding a water-soluble stilbene compound; a nonionic surface active agent or a mixture thereof to a developing solution, (2) a method of treating the photographic material with an oxidizing agent after bleaching and fixing to rupture the dye, and (3) a method of using a persulfuric acid-bleaching bath as a bleaching bath, as described in "Research Disclosure", Vol. 207, No. 20733 (July, 1981). However, in these methods, satisfactory decoloration can not be attained when the color remains at high density. Further, according to these methods, detachment and removal of the dyes such as sensitizing dye is no accelerated. Hence, these methods are unsuitable for rapid decoloration.

Decoloring methods of dyes are also described, for example, in Japanese Patent Provisional Publications No. 64(1989)-4739, No. 64(1989)-15734, No. 1(1989)-9451, No. 64(1989)-35440, No. 1(1989)-21444, No. 1(1989)-35441 and No. 1(1989)-159645. Any of these methods comprise incorporation of an additive to a developing solution or other processing solution. These methods also are insufficient, although they improve decoloring efficiency to some extent. Further, as a similar method, a method of decoloring by rupturing association of sensitizing dyes is proposed in U.S. Pat. No. 4,906,553 and Japanese Patent Provisional Publication No. 2(1990)-71260. This method comprises incorporation of an additive to a processing solution, so as to give decoloration at high efficiency. Particularly, the method described in Japanese Patent Provisional Publication No. 2(1990)-71260 is excellent in decoloring. However, since the activity of the processing solution for decoloration decreases with the elapse of time or after repeated use of the processing solution, the processing solution should be stored under severe control.

As described previously, there are known the use of water-soluble sensitizing dyes to reduce residual color in the resulting image. Howerver, these sensitizing dyes have disadvantages; for example, the spectral sensitivity is low or the level of the residual color is not sufficiently low (see: U.S. Pat. No. 4,250,224). Japanese Patent Provisional Publication No. 3(1991)-105339 discloses a thiazole type sensitizing dye which gives reduced residual color and showing high spectral sensitivity. However, this thiazole type dye is not still sufficiently improved in giving the residual color when the material containing the dye is processed by a photographic process including a conventional developing step, though the spectral sensitivity of the dye is high.

As described above, in order to decolor unnecessary dyes in the process for forming an image such as a photographic image, these dyes are generally removed from the photographic material after the exposure step. However, the decoloraion process for efficiently removing the unnecessary dyes is complicated, and this complicated process disturbs reduction of the processing time of a photographic light-sensitive material in the developing process. Studies on the sensitizing dyes which are easily removed in the generally employed developing process have been also made, but no sensitizing dyes which are satisfactory in both the spectral sensitivity and the level of the residual color have been discovered.

Recently, small sized development processing devices (so-called "mini-laboratory") have been widely employed, and hence it is desired to carry out the decoloration in a manner as simple as possible and within a short time. Further, a system or a dye which needs no decoloration processing is desired, from the viewpoints of reduction of waste processing solutions and prevention of environmental pollution.

SUMMARY OF THE INVENTION

It is an object of the present invention to provide a silver halide photographic light-sensitive material which gives an excellent photographic image with reduced residual color after an image formation process such as a development process is complete.

It is another object of the invention to provide a silver halide photographic light-sensitive material which gives an excellent photographic image with reduced residual color even when a rapid image formation process is employed.

It is a further object of the invention to provide a novel methine compound which is favorably employed for a silver halide photographic light-sensitive material.

There is provided by the present invention a silver halide photographic light-sensitive material containing a methine compound represented by the following formula (I):

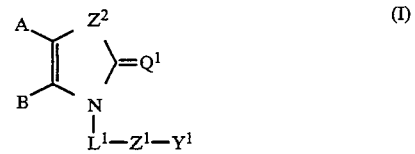

wherein $Y^1$ is a group which is cleavable by a nucleophile at the portion bonding to $Z^1$;

$Z^1$ represents —O—, —S—, or —NR$^1$— in which R$^1$ is a hydrogen atom, or an alkyl, aryl or heterocyclic group which may have a substituent, or a group which is cleavable by a nucleophile at the portion bonding to N;

$L^1$ represents an ethylene or propylene group which may have a substituent group;

$Z^2$ represents —O—, —S—, —Se—, —Te—, —NR$^2$—, —CR$^3$R$^4$—, or —CR$^5$=CR$^6$— in which R$^2$, $R^3$, $R^4$, $R^5$ and $R^6$ are each independently a hydrogen atom, an alkyl, aryl or heterocyclic group which may have a substituent, and $R^3$ and $R^4$, and $R^5$ and $R^6$ each may be combined to each other to form a ring;

A and B represent each independently a hydrogen atom, a halogen atom, a sulfo group, a carboxyl group, a nitro group, a cyano group, a hydroxyl group or an alkyl, alkenyl, acyl, acyloxy, alkoxycarbonyl, carbamoyl, sulfamoyl, acylamino, alkoxy, aryloxy, alkylthio, arylthio, alkylsulfonamido, arylsulfonamido, ureido, alkylsulfonyl, arylsulfonyl, aryl or heterocyclic group which may have a substituent; A and B may be linked to each other to form an unsaturated aliphatic ring, an aromatic ring or a heterocyclic ring; and $Q^1$ represents a methine or polymethine group which may have a heterocyclic group.

Preferred methine compounds for the preparation of the above-mentioned silver halide photographic light-sensitive material of the invention are as follows:

(1) The methine compound of the formula (I) wherein $Z^2$ is —S—, —Se—, —$NR^2$— or —$CR^5$=$CR^6$—.

(2) The methine compound of the formula (I) wherein $L^1$ is an ethylene group.

(3) The methine compound of the formula (I) wherein $Y^1$ is an acyl group, a carbamoyl group, an alkoxycarbonyl group, an aryloxycarbonyl group, an alkylsulfonyl group, an arylsulfonyl group, an alkylaminosulfonyl group, an arylaminosulfonyl group, an acylaminosulfonyl group, a substituted sulfonylaminosulfonyl group, a phosphoric ester group, a heterocyclic group, a silyl group or a sulfo group.

(4) The methine compound of the formula represented by the following formula (II):

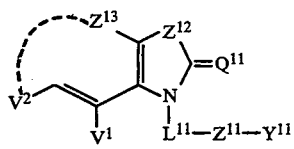

(II)

wherein $Y^{11}$ is a group which is clearable by a nucleophile at the portion bonding to $Z^{11}$;

$Z^{11}$ represents —O—, —S—, or —$NR^{11}$— in which $R^{11}$ is a hydrogen atom, an alkyl group which may be substituted with alkoxy, an aryl group which may be substituted with halogen, a heterocyclic group, or a group which is cleavable by a nucleophile at the portion bonding to N;

$L^{11}$ represents an ethylene or propylene group which may be substituted with a hydroxyl group, a sulfo group, a carboxyl group, an alkyl group, an alkoxy group, an aryloxy group, an alkylthio group, an acyloxy group, an acyl group, a sulfamoyl group, an aryl group or a heterocyclic group;

$Z^{12}$ represents —O—, —S—, —Se—, —Te—, —$NR^{12}$—, —$CR^{13}R^{14}$—, or —$CR^{15}$=$CR^{16}$—, in which $R^{12}$, $R^{13}$, $R^{14}$, $R^{15}$ and $R^{16}$ are each independently a hydrogen atom, an alkyl group which may be substituted with carboxyl, sulfo, halogen, hydroxyl, acetyl, methylthio, methoxy, methanesulfonamino, acetylamino or methanesulfonylcarbamoyl, an aryl group which may be substituted with carboxyl, sulfo, cyano, nitro, hydroxyl, halogen, alkyl, alkoxy, aryloxy, acyloxy, acyl, sulfamoyl, carbamoyl or aryl, or a heterocyclic group, and $R^{13}$ and $R^{14}$, and $R^{15}$ and $R^{16}$ each may be combined to each other to form a ring;

$V^1$ represents a halogen atom, a sulfo group, a carboxyl group, a nitro group, an alkyl group which may be substituted with alkoxy, an alkenyl group, an acyl group, an acyloxy group, an alkoxycarbonyl group, a carbamoyl group, a sulfamoyl group, an acylamino group, an alkoxy group, an aryloxy group, an alkylthio group, an arylthio group, an alkylsulfonamido group, an arylsulfonamido group, a ureido group, an alkylsulfonyl group, an arylsulfonyl group, an aryl group which may be substituted with halogen, or a heterocyclic group;

$V^2$ represents a hydrogen atom, a halogen atom, a sulfo group, a carboxyl group, a nitro group, a cyano group, a hydroxyl group, an alkyl which may be substituted with alkoxy, an alkenyl group, an acyl group, an acyloxy group, an alkoxycarbonyl group, a carbamoyl group, a sulfamoyl group, an acylamino group, an alkoxy group, an aryloxy group, an alkylthio group, an arylthio group, an alkylsulfonamido group, an arylsulfonamido group, a ureido group, an alkylsulfonyl group, an arylsulfonyl group, an aryl group which may be substituted with halogen, or a heterocyclic group; $V^1$ and $V^2$ may be linked to each other to form an unsaturated aliphatic ring, an aromatic ring or a heterocyclic ring;

$Z^{13}$ represents —$CV^3$=$CV^4$—, —$CV^5V^6$—$CV^7V^8$—, —$CV^9$=N—, —$CV^{10}V^{17}$—$NR^{17}$—, —$CV^{11}V^{12}$—O—, —$CV^{13}V^{14}$—S—, —$CV^{15}V^{16}$—CO—, —O—, —S—, —$CV^{18}V^{19}$—, —$NR^{20}$— in which $V^3$, $V^4$, $V^5$, $V^6$, $V^7$, $V^8$, $V^9$, $V^{10}$, $V^{11}$, $V^{12}$, $V^{13}$, $V^{14}$, $V^{15}$, $V^{16}$, $V^{17}$, $V^{18}$ and $V^{19}$ are each independently a hydrogen atom, a halogen atom, a sulfo group, a carboxyl group, a nitro group, a cyano group, a hydroxyl group, an alkyl group, an alkenyl group, an acyl group, an acyloxy group, an alkoxycarbonyl group, a carbamoyl group, a sulfamoyl group, an acylamino group, an alkoxy group, an aryloxy group, an alkylthio group, an arylthio group, an alkylsulfonamido group, an arylsulfonamido group, a ureido group, an alkylsulfonyl group, an arylsulfonyl group, an aryl group or a heterocyclic group, $R^{17}$ and $R^{20}$ represent each a hydrogen atom or an alkyl group which may be substituted with carboxyl, sulfo, halogen, hydroxyl, acetyl, methylthio, methoxy, methanesulfonamino, acetylamino or methanesulfonylcarbamoyl, an aryl group which may be substituted with carboxyl, sulfo, cyano, nitro, hydroxyl, halogen, alkyl, alkoxy, aryloxy, acyloxy, acyl, sulfamoyl, carbamoyl or aryl, or a heterocyclic group, and $R^{17}$ and $V^{10}$, and $R^{17}$ and $V^{17}$ each may be combined to each other to form a ring; and $Q^{11}$ represents a methine or polymethine group which may have a heterocyclic group.

Preferred methine compounds of the formula (II) are as follows:

(a) The methine compound wherein $Z^{12}$ is —S—, —Se—, —$NR^{12}$— or —$CR^{15}$=$CR^{16}$—.

(b) The methine compound wherein $L^{11}$ is an ethylene group.

(c) The methine compound wherein $Y^{11}$ is an acyl group, a carbamoyl group, an alkoxycarbonyl group, an aryloxycarbonyl group, an alkylsulfonyl group, an arylsulfonyl group, an alkylaminosulfonyl group, an arylaminosulfonyl group, an acylaminosulfonyl group, a substituted sulfonylaminosulfonyl group, a phosphoric ester group, a heterocyclic group, a silyl group or a sulfo group.

(d) The methine compound wherein $V^1$ is a methyl group, a chlorine or bromine atom or a benzene ring formed by combining to $V^2$.

(5) The methine compound represented by the following formula (III):

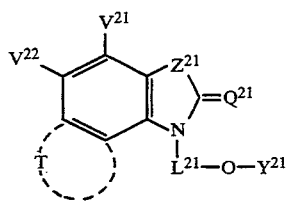

wherein each of $V^{21}$ and $V^{22}$ independently represents a hydrogen atom, an alkyl group which may be substituted with carboxyl, sulfo or halogen, a halogen atom, an acyl group, an acyloxy group, an alkoxycarbonyol group, a carbamoyl group, a sulfamoyl group, a sulfo group, a carboxy group, a cyano group, a hydroxyl group, an amino group, an acylamino group, an alkoxy group, an aryloxy group, an alkylthio group, an arylthio group, a sulfonamide group, a ureido group, an alkylsulfonyl group, an arylsulfonyl group, an aryl group which may be substituted with halogen or methyl, or a heterocyclic group;

$Z^{21}$ represents —O—, —S—, —Se—, —NR$^{22}$— in which $R^{22}$ represents a hydrogen atom, a hydrogen atom or an alkyl group which may be substituted with carboxyl, sulfo, halogen, hydroxyl, acetyl, methylthio, methoxy, methanesulfonamino, acetylamino or methanesulfonylcarbamoyl, an aryl group which may be substituted with carboxyl, sulfo, cyano, nitro, hydroxyl, halogen, alkyl, alkoxy, aryloxy, acyloxy, acyl, sulfamoyl, carbamoyl or aryl, or a heterocyclic group, —CR$^{23}$R$^{24}$— in which each of $R^{23}$ and $R^{24}$ independently represents a hydrogen atom or an alkyl group which may be substituted with carboxyl, sulfo, halogen, hydroxyl, acetyl group, methylthio, methoxy, methanesulfonamino, acetylamino or methanesulfonylcarbamoyl, or —CV$^{23}$=V$^{24}$— in which each of $V^{23}$ and $V^{24}$ independently represents a hydrogen atom, an alkyl group which may be substituted with carboxyl, sulfo or halogen, a halogen atom, an acyl group, an acyloxy group, an alkoxycarbonyol group, a carbamoyl group, a sulfamoyl group, a sulfo group, a carboxy group, a cyano group, a hydroxyl group, an amino group, an acylamino group, an alkoxy group, an aryloxy group, an alkylthio group, an arylthio group, a sulfonamide group, a ureido group, an alkylsulfonyl group, an arylsulfonyl group, an aryl group which may be substituted with halogen or methyl, or a heterocyclic group;

T represents a group of atoms to form an aromatic ring, an aliphatic ring or a heterocyclic ring together with the hydrocarbon moiety of the benzene ring to which T is bonded;

$L^{21}$ represents an ethylene group or propylene group which may be substituted with a hydroxyl group, a sulfo group, a carboxyl group, an alkyl group, an alkoxy group, an aryloxy group, an alkylthio group, an acyloxy group, an acyl group, a sulfamoyl group, an aryl group or a heterocyclic group;

$Y^{21}$ represents a group that is cleavable at a portion bonding to oxygen of the group; and $Q^{21}$ represents a methine group or polymethine group which may have a heterocyclic group.

Preferred methine compounds of the formula (III) are as follows:

(a) The methine compound wherein $Z^{21}$ represents —S—, —Se— or —NR$^{22}$—.

(b) The methine compound wherein $L^{21}$ represents an ethylene group.

(c) The methine compound wherein T represents a group to form a benzene ring together with a hydrocarbon group of a benzene ring (d) The methine compound wherein that $Y^{21}$ is an alkyl group, an aryl group, an acyl group, a carbamoyl group, an alkoxycarbonyl group, an aryloxycarbonyl group, an alkylsulfonyl group, an arylsulfonyl group, an alkylaminosulfonyl group, an arylaminosulfonyl group, an acylaminosulfonyl group, a substituted sulfonylaminosulfonyl group, a phosphoric ester group, a heterocyclic group, a silyl group or a sulfo group.

Preferred embodiments of the silver halide photographic light-sensitive material of the invention are as follows.

(1) The silver halide photographic light-sensitive material which comprises a support and an emulsion layer and the emulsion layer contains the above-mentioned methine compound.

(2) The silver halide photographic light-sensitive material which comprises a support, an emulsion layer and a protective layer and at least the protective layer contains the above-mentioned methine compound.

(3) The silver halide photographic light-sensitive material which comprises a back layer, a support, an emulsion layer and a protective layer and at least the back layer contains the above-mentioned methine compound.

(4) The silver halide photographic light-sensitive material which comprises a back layer, a support, an antihalation layer, an emulsion layer, an intermediate layer, an ultraviolet absorbing layer and a protective layer and at least one of these layers contains the above-mentioned methine compound.

In the silver halide photographic light-sensitive material of the invention, a layer or layers such as an emulsion layer constituting the material contain the specific methine compound of the formula (I). By use of the material, the unnecessary dyes can be removed only by utilizing properties of a developing solution such as alkaline characteristics even under rapid processing conditions, without using a specific decoloring agent to remove the dyes. Accordingly, color stains caused by various unnecessary dyes, which are usually observed, are reduced.

In other words, when the methine compound of the aforementioned formula (I) is used as a sensitizing dye in the emulsion layer, the dye can be easily removed by the developing solution. Further, even if a certain amount of the dye remains in the photographic material, residual color is rarely observed because the dye can be easily decolored by the alkaline property of the developing solution. In addition, the dye of the formula (I) shows a high spectral sensitivity and is excellent as a sensitizing dye.

DETAILED DESCRIPTION OF THE INVENTION

The silver halide photographic light-sensitive material of the invention contains a methine compound of the above formula (I), preferably a methine compound of the above formula (II), and more preferably a methine compound of the above formula (III)

The methine compound represented by the formula (I) is described below in more detail.

$Z^1$ is —O—, —S— or —NR$^1$— (wherein R$^1$ is a hydrogen atom, an alkyl, aryl or heterocyclic group which may be substituted or a group which can be cleaved at the portion (position) bonding to the nitrogen atom).

Examples of R$^1$ include a hydrogen atom, an alkyl group of 1 to 18 carbon atoms (e.g., methyl, ethyl), an alkoxyalkyl group of 1 to 18 carbon atoms (e.g., methoxyethyl), an aryl group of 6 to 15 carbon atoms (e.g., phenyl, p-chlorophenyl), and a heterocyclic group of 5 to 15 carbon atoms (e.g., 2-thiazolyl). R$^1$ may be combined to Y$^1$ to form a phthaloyl group. R$^1$ is preferred to be an alkyl group, and particularly preferred to be methyl.

Y$^1$ is a group having property that can be cleaved by a nucleophile at the portion (position) bonding to Z$^1$.

Examples of the nucleophiles which cleaves the bond between Y$^1$ and Z$^1$ (e.g., —O—, —S—) include water, alcohol, amine, mercaptane, hydrazine, hydroxylamine, hydroxamic acid or anions thereof, halogen ion, thiocyanic acid ion and sulfate ion. Hydrolysis under acidic or basic condition is most generally employed for the cleavage. As a special case, there can be mentioned a method in which the methine compound and the nucleophile are separately kept from each other and then are heated from the outside to fuse them or bring them into contact with each other.

Y$^1$ preferably is a group corresponding to a block group capable of releasing a development inhibitor or a precursor thereof in the photographic developing process (e.g., a block group disclosed in Japanese Patent Provisional Publication No. 62(1987)-30243).

Examples of such block groups include an acyl group and a sulfonyl group as described in Japanese Patent Publication No. 48(1973)-9968, Japanese Patent Provisional Publications No. 52(1977)-8828 and No. 57(1982)-82834, U.S. Pat. No. 3,311,476, and Japanese Patent Publication No. 47(1972)-44805 (U.S. Pat. No. 3,615,617); groups which are cleaved by so-called "reverse Michael reaction" as described in Japanese Patent Publications No. 55(1980)- 17369 (U.S. Pat. No. 3,888,677), No. 55(1989)-9696 (U.S. Pat. No. 3,791,830) and No. 55(1980)-34927 (U.S. Pat. No. 4,009,029), and Japanese Patent Provisional Publications No. 56(1981)-77842 (U.S. Pat. No. 4,307,175), No. 59(1984)-105642 and No. 59(1984)-105640; groups which are cleaved with production of quinonemethide or quinonemethide compound by intramolecular electron transfer as described in Japanese patent Publication No. 54(1979)-39727, U.S. Pat. No. 3,674,478, No. 3,932,480 and No. 3,993,661, and Japanese Patent Provisional Publications No. 57(1982)-135944, No. 57(1982)-135945 and No. 57(1982)-136640; groups which are cleaved by intramolecular ring closure reaction as described in Japanese Patent Provisional Publications No. 55(1980)-53330 and No. 50(1984)-218439; groups which are cleaved by formation of 5- or 6-membered ring as described in Japanese Patent Provisional Publications No. 57(1982)-76541 (U.S. Pat. No. 4,335,200), No. 57(1982)-135949, No. 57(1982)-179842, No. 59(1984)-137945, No. 59(1984)-140445, No. 59(1984)-219741 and No. 60(1985)-41034; and groups which are cleaved by addition of a nucleophile to unsaturated bond as described in Japanese Patent Provisional Publication No. 59(1984)-201057, and Japanese Patent Applications No. 59(1984)-145593, No. 59(1984)-216926 and No. 59(1984)-216928.

In general, Y$^1$ is an acyl group of 1 to 22 carbon atoms (e.g., benzoyl, acetyl, pivaloyl, stearoyl), a carbamoyl group of 1 to 22 carbon atoms (e.g., carbamoyl, methylcarbamoyl, ethylcarbamoyl, phenylcarbamoyl), an alkoxycarbonyl group of 1 to 22 carbon atoms (e.g., methoxycarbonyl, ethoxycarbonyl), an aryloxycarbonyl group of 7 to 16 carbon atoms (e.g., phenoxycarbonyl), an alkylsulfonyl group of 1 to 22 carbon atoms (e.g., methanesulfonyl), an arylsulfonyl group of 6 to 16 carbon atoms (e.g., benzenesulfonyl, p-toluenesulfonyl), an alkylaminosulfonyl group of 1 to 12 carbon atoms (e.g., ethylaminosulfonyl), an arylaminosulfonyl group of 16 or less carbon atoms (e.g., phenylaminosulfonyl), an acylaminosulfonyl group of 1 to 16 carbon atoms (e.g., acetylaminosulfonyl), a phosphoric acid ester group of 1 to 12 atoms (e.g., dimethoxyphosphoryl), a heterocyclic group of 5 to 15 carbon atoms (e.g., 2-benzoxazolyl, 2-tetrahydropyranyl), a silyl group of 1 to 16 carbon atoms or sulfo group. These groups may further have one or more substituents. Examples of substituents of those groups include cyano, hydroxyl, methoxy, nitro, methanesulfonyl, carbamoyl, carboxyl, sulfo, halogen, mercapto, methylthio, ureido, methanesulfonylamino, acetyl, thioacetyl, thioamido, 2-cyanoethyl, methoxyethyl, methanesulfonylcarbamoyl and 4-chlorophenoxy.

When Y$^1$ is bonded to the oxygen atom or a sulfur atom, Y$^1$ preferably is acetyl, ethoxycarbonyl, ethylcarbamoyl or dimethylsulfamoyl group. When Y$^1$ is bonded to the nitrogen atom, Y$^1$ preferably is ethoxycarbonyl, benzenesulfonyl, phthaloyl or trifluoroacetyl.

Y$^1$ may further have a divalent linking group between Y$^1$ and the oxygen atom to which Y$^1$ is bonded.

Such linking group includes groups which are cleaved by intramolecular ring closure reaction as described in Japanese Patent Provisional Publication No. 54(1979)-145135 (U.K. Patent No. 2010818A), groups which are cleaved by intramolecular electron transfer as described in Japanese Patent Provisional Publication No. 57(1982)-154234, groups which are cleaved with release of carbon dioxide gas as described in Japanese Patent Provisional Publication No. 57(1982)-179842 and groups which are cleaved with release of formalin as described in Japanese Patent Provisional Publication No. 59(1984)-93442.

Typical examples of the above-described linking groups are given below.

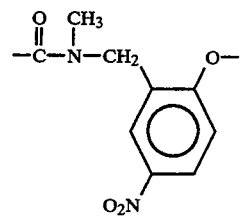

ZY-1

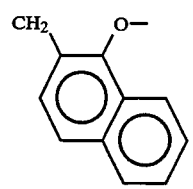

ZY-2

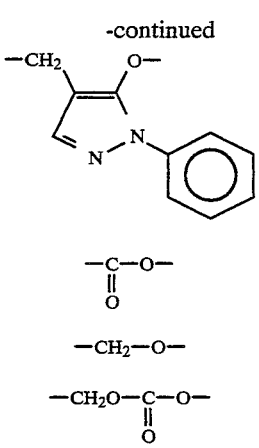

ZY-3

—C—O—
‖
O
ZY-4

—CH₂—O—   ZY-5

—CH₂O—C—O—
‖
O
ZY-6

L¹ is an ethylene or propylene group which may have a substituent group. Examples of the substituent groups include a hydroxyl group, a sulfo group, a carboxyl group, an alkyl group of 1 to 8 carbon atoms (e.g., methyl, ethyl, propyl, butyl), an alkoxy group of 1 to 8 carbon atoms (e.g., methoxy, ethoxy, benzyloxy, phenetyloxy), an aryloxy group of 6 to 15 carbon atoms (e.g., phenoxy), an alkylthio group of 1 to 8 carbon atoms (e.g., methylthio, ethylthio, benzylthio), an acyloxy group of 1 to 8 carbon atoms (e.g., acetyloxy), an acyl group of 1 to 8 carbon atoms, a sulfamoyl group of 1 to 8 carbon atoms, an aryl group of 6 to 15 carbon atoms (e.g., phenyl, 4-methylphenyl, 4-chlorophenyl, 2-naphthyl) and a heterocyclic group of 5 to 15 carbon atoms (e.g., 2-pyrimidyl, 2-thiazolyl). L¹ is usually ethylene, methylethylene, 1,2-dimethylethylene, phenylethylene, propylene or 2-methylpropylene; preferably ethylene or propylene; more preferably ethylene.

$Z^2$ is —O—, —S—, —Se—, —Te—, —NR²—, —CR³R⁴— or —CR⁵=CR⁶— (wherein R², R³, R⁴, R⁵ and R⁶ are each independently a hydrogen atom or an alkyl, aryl or heterocyclic group which may be substituted, and each of R³ and R⁴, and R⁵ and R⁶ may be combined to each other to form a ring). Preferred are —S—, —Se—, —Te—, —NR²— and —CR⁵=CR⁶—, and a particularly preferred is —S—.

Each of R², R³, R⁴, R⁵ and R⁶ is generally a hydrogen atom, an alkyl group of 1 to 8 carbon atoms which may have substituent, an aryl group of 6 to 15 carbon atoms which may have substituent or heterocyclic group of 5 to 15 carbon atoms which may have substituent.

Examples of the alkyl group of 1 to 8 carbon atoms include groups of methyl, ethyl, propyl, isopropyl, allyl, butyl, isobutyl, hexyl and octyl. Examples of the substituents of these groups include carboxyl, sulfo, halogen, hydroxyl, acetyl, methylthio, methoxy, methanesulfonamino, acetylamino and methanesulfonylcarbamoyl. Preferred are methyl, ethyl and methoxyethyl.

Examples of the aryl group of 6 to 15 carbon atoms which may have substituent include phenyl, 2-naphthyl and 1-naphthyl. Example of the substituent group include carboxyl, sulfo, cyano, nitro, hydroxyl, halogen, alkyl of 1 to 8 carbon atoms (e.g., methyl, ethyl), alkoxy of 1 to 8 carbon atoms (e.g., methoxy, ethoxy), aryloxy of 6 to 15 carbon atoms (e.g., phenoxy), acyloxy of 1 to 8 carbon atoms (e.g., acetyloxy), acyl of 1 to 8 carbon atoms, sulfamoyl of 1 to 8 carbon atoms, carbamoyl of 1 to 8 carbon atoms and aryl of 6 to 15 carbon atoms. Preferred are phenyl and 4-methylphenyl.

Examples of the heterocyclic group of 1 to 15 carbon atoms which may be substituted include 2-pyridyl, 2-thiazolyl, 2-furyl and 2-thiophenyl.

An example of the ring formation is a case where —CR³R⁴— forms a piperidine ring.

Preferred groups indicated by R², R³, R⁴, R⁵ and R⁶ are an unsubstituted alkyl group (e.g., methyl, ethyl, propyl, butyl) and an unsubstituted aryl group (e.g., phenyl, 1-naphthyl). Particularly preferred are methyl, ethyl, and phenyl.

In the formula (I) for the methine compound, A and B are each independently a hydrogen atom, a halogen atom, a sulfo group, a carboxyl group, a nitro group, a cyano group, a hydroxyl group, or an alkyl, alkenyl, acyl, acyloxy, alkoxycarbonyl, carbamoyl, sulfamoyl, acylamino, alkoxy, aryloxy, alkylthio, arylthio, alkylsulfonamido, arylsulfonamido, ureido, alkylsulfonyl, arylsulfonyl, aryl or heterocyclic group which may have a substituent; and A and B may be combined to each other to form an unsaturated aliphatic ring, an aromatic ring or a heterocyclic ring.

Each of A and B is generally a hydrogen atom, an alkyl group of 1 to 18 carbon atoms (e.g., methyl, ethyl, propyl, 2-methoxyethyl), an alkenyl group of 1 to 18 carbon atoms (e.g., vinyl, styryl), a halogen atom (e.g., chlorine, bromine), an acyl group of 1 to 8 carbon atoms (e.g., acetyl), an acyloxy group of 1 to 8 carbon atoms (e.g., acetyloxy), an alkoxycarbonyl group of 1 to 8 carbon atoms (e.g., methoxycarbonyl), a carbamoyl group of 1 to 8 carbon atoms (e.g., N-methylcarbamoyl), a sulfamoyl group of 1 to 8 carbon atoms (e.g., N-methylsulfamoyl), a carboxyl group, an alkylsulfonamido group of 1 to 8 carbon atoms (e.g., methanesulfonamido), an acylamino group of 1 to 8 carbon atoms (e.g., acetylamino), an alkoxy group of 1 to 15 carbon atoms (e.g., methoxy, ethoxy, benzyloxy, phenetyloxy), an aryloxy group of 6 to 15 carbon atoms (e.g., phenoxy), an alkylthio group of 1 to 8 carbon atoms (e.g., methylthio, ethylthio), an arylthio group of 6 to 15 carbon atoms (e.g., phenylthio), an arylsulfonamido group of 6 to 12 carbon atoms (e.g., benzenesulfonamido), a ureido group, an alkylsulfonyl group of 1 to 8 carbon atoms (e.g., methanesulfonyl, ethylsulfonyl), an arylsulfonyl group of 6 to 15 carbon atoms (e.g., benzenesulfonyl, p-toluenesulfonyl), an aryl group of 6 to 15 carbon atoms (e.g., phenyl, 4-methylphenyl, 4-chlorophenyl, 2-naphthyl), a nitro group, a sulfo group, a hydroxyl group, a cyano group or a heterocyclic group of 5 to 15 carbon atoms (e.g., morpholino, 2-pyridyl). These groups may be further substituted. A and B may be combined to each other to form a cyclohexene ring, an aromatic ring or a heterocyclic ring, so as to form a condensed ring together with the heterocyclic ring having A and B.

Q¹ is a methine group which may have a heterocyclic group or a polymethine group which may have a heterocyclic group. Details with respect to Q¹ will be described later.

The methine compound of the formula (I) is described hereinbefore. Description on the symbols other than A and B in the above description can be basically applied to the methine compound of the formula (II); i.e., Q¹, Y¹, L¹, Z¹, Z², R², R³, R⁴, R⁵ and R⁶ correspond to Q¹¹, Y¹¹, L¹¹, Z¹¹, Z¹², R¹², R¹³, R¹⁴, R¹⁵ and R¹⁶, respectively.

The methine compound of the formula (II) is novel, and is a preferred methine compound among the compounds of the formula (I). The methine compound of the formula (II) is described below.

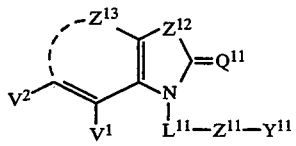

In the formula (II), $Y^{11}$ is the same group as defined for $Y^1$ of the formula (I).

$Q^{11}$ is the same group as defined for $Q^1$ of the formula (I).

$Z^{11}$ is —O—, —S— or —NR$^{11}$— (wherein R$^{11}$ is a hydrogen atom, an alkyl, aryl or heterocyclic group which may have a substituent or a group which is cleavable at the portion bonding to the nitrogen atom, said substituent being an alkoxy group or a halogen atom). The preferred examples are the same as those mentioned for $Z^1$ of the formula (I).

$L^{11}$ is an ethylene or propylene group which may have a substituent group, said substituent being a hydroxyl group, a sulfo group, a carboxyl group, an alkyl group of 1 to 8 carbon atoms, an alkoxy group of 1 to 8 carbon atoms, an aryloxy group of 6 to 15 carbon atoms, an alkylthio group of 1 to 8 carbon atoms, an acyloxy group of 1 to 8 carbon atoms, an acyl group of 1 to 8 carbon atoms, a sulfamoyl group of 1 to 8 carbon atoms, an aryl group of 6 to 15 carbon atoms and a heterocyclic group of 5 to 15 carbon atoms. The preferred examples are the same as those mentioned for $L^1$ of the formula (I).

$Z^{12}$ is —O—, —S—, —Se—, —Te—, —NR$^{12}$—, —CR$^{13}$R$^{14}$— or —CR$^{15}$=CR$^{16}$— (wherein R$^{12}$, R$^{13}$, R$^{14}$, R$^{15}$ and R$^{16}$ are each independently a hydrogen atom or an alkyl group which may have a substituent, an aryl group which may have a substituent or a heterocyclic group, and each of R$^{13}$ and R$^{14}$, and R$^{15}$ and R$^{16}$ may be combined to each other to form a ring, said substituent of said alkyl group being carboxyl, sulfo, halogen, hydroxyl, acetyl, methylthio, a methoxy, methanesulfonamino, acetylamino or methanesulfonylcarbamoyl, said substituent of said aryl group being carboxyl, sulfo, cyano, nitro, hydroxyl, halogen, alkyl of 1 to 8 carbon atoms, alkoxy group of 1 to 8 carbon atoms, aryloxy group of not more than 15 carbon atoms, acyloxy of 1 to 8 carbon atoms, acyl of 1 to 8 carbon atoms, sulfamoyl of 1 to 8 carbon atoms, carbamoyl of 1 to 8 carbon atoms and aryl of not more than 15 carbon atoms). The preferred examples are the same as those mentioned for $Z^2$, $R^2$, $R^3$, $R^4$, $R^5$ and $R^6$ of the formula (I).

$V^1$ is a halogen atom, a sulfo group, a carboxyl group, a nitro group, an alkyl which may be substituted with an alkoxy group, an alkenyl group, an acyl group, an acyloxy group, an alkoxycarbonyl group, a carbamoyl group, a sulfamoyl group, an acylamino group, an alkoxy group, an aryloxy group, an alkylthio group, an arylthio group, an alkylsulfonamido group, an arylsulfonamido group, a ureido group, an alkylsulfonyl group, an group, an arylsulfonyl group, an aryl group which may be substituted with a halogen atom or a heterocyclic group which may have a substituent.

$V^1$ generally is an alkyl group of 1 to 18 carbon atoms (e.g., methyl, ethyl, propyl, 2-methoxyethyl), an alkenyl group of 1 to 18 carbon atoms (e.g., vinyl, styryl), a halogen atom (e.g., chlorine, bromine), an acyl group of 1 to 8 carbon atoms (e.g., acetyl), an acyloxy group of 1 to 8 carbon atoms (e.g., acetyloxy), an alkoxycarbonyl group of 1 to 8 carbon atoms (e.g., methoxycarbonyl), a carbamoyl group of 1 to 8 carbon atoms (e.g., N-methylcarbamoyl), a sulfamoyl group of 1 to 8 carbon atoms (e.g., N-methylsulfamoyl), a carboxyl group, an alkylsulfonamido group of 1 to 8 carbon atoms (e.g., methanesulfonamido), an acylamino group of 1 to 8 carbon atoms (e.g., acetylamino), an alkoxy group of 1 to 15 carbon atoms (e.g., methoxy, ethoxy, benzyloxy, phenetyloxy), an aryloxy group of 6 to 15 carbon atoms (e.g., phenoxy), an alkylthio group of 1 to 8 carbon atoms (e.g., methylthio, ethylthio), an arylthio group of 6 to 15 carbon atoms (e.g., phenylthio), an arylsulfonamido group of 6 to 12 carbon atoms (e.g., benzenesulfonamido), a ureido group, an alkylsulfonyl group of 1 to 8 carbon atoms (e.g., methanesulfonyl, ethylsulfonyl), an arylsulfonyl group of 6 to 15 carbon atoms (e.g., benzenesulfonyl, p-toluenesulfonyl), an aryl group of 6 to 15 carbon atoms (e.g., phenyl, 4-methylphenyl, 4-chlorophenyl, 2-naphthyl), a nitro group, a sulfo group, or a heterocyclic group of 5 to 15 carbon atoms (e.g., morpholino, 2-pyridyl). These substituent groups may be further substituted.

Examples of the group indicated by $V^2$ include a hydrogen atom, a hydroxyl group and a cyano group in addition to the above groups exemplified for $V^1$. $V^2$ generally is a hydrogen atom, a hydroxyl group or a cyano group in addition to the above groups exemplified for $V^1$.

$V^1$ and $V^2$ may be combined to each other to form a cyclohexene ring, an aromatic ring or a heterocyclic ring, so as to form a condensed ring together with the heterocyclic ring having $V^1$ and $V^2$.

$V^1$ is preferred to be methyl or chlorine. It is also preferred that $V^1$ and $V^2$ are combined to each other to form a benzene ring. $V^2$ is preferred to be hydrogen, methyl and chlorine.

$Z^{13}$ is —CV$^3$=CV$^4$—, —CV$^5$V$^6$—CV$^7$V$^8$—, —CV$^9$=N—, —CV$^{10}$V$^{17}$—NR$^{17}$—, —CV$^{11}$V$^{12}$—O—, —CV$^{13}$V$^{14}$—S—, —CV$^{15}$V$^{16}$—CO—, —O—, —S—, —CV$^{18}$V$^{19}$—, —NR$^{20}$—; wherein V$^3$, V$^4$, V$^5$, V$^6$, V$^7$, V$^8$, V$^9$, V$^{10}$, V$^{11}$, V$^{12}$, V$^{13}$, V$^{14}$, V$^{15}$, V$^{16}$, V$^{17}$, V$^{18}$ and V$^{19}$ are each independently a hydrogen atom, a halogen atom, a sulfo group, a carboxyl group, a nitro group, a cyano group, a hydroxyl group, an alkyl group, an alkenyl group, an acyl group, an acyloxy group, an alkoxycarbonyl group, a carbamoyl group, a sulfamoyl group, an acylamino group, an alkoxy group, an aryloxy group, an alkylthio group, an arylthio group, an alkylsulfonamido group, an arylsulfonamido group, a ureido group, an alkylsulfonyl group, an arylsulfonyl group, an aryl group or a heterocyclic group. These groups may have substituents.

$V^3$, $V^4$, $V^5$, $V^6$, $V^7$, $V^8$, $V^9$, $V^{10}$, $V^{11}$, $V^{12}$, $V^{13}$, $V^{14}$, $V^{15}$, $V^{16}$, $V^{17}$, $V^{18}$ and $V^{19}$ are each generally a hydrogen atom, a halogen atom, a sulfo group, a carboxyl group, a nitro group, a cyano group, a hydroxyl group, an alkyl group of 1 to 18 carbon atoms (e.g., methyl, ethyl, propyl, 2-methoxyethyl), an alkenyl group of 1 to 18 carbon atoms (e.g., vinyl, styryl), a halogen atom (e.g., chlorine, bromine), an acyl group of 1 to 8 carbon atoms (e.g., acetyl), an acyloxy group of 1 to 8 carbon atoms (e.g., acetyloxy), an alkoxycarbonyl group of 1 to 8 carbon atoms (e.g., methoxycarbonyl), a carbamoyl group of 1 to 8 carbon atoms (e.g., N-methylcarbamoyl), a sulfamoyl group of 1 to 8 carbon atoms (e.g., N-methylsulfamoyl), a carboxyl group, an alkylsulfonamido group of 1 to 8 carbon atoms (e.g., methanesulfonamido), an acylamino group of 1 to 8 carbon atoms (e.g., acetylamino), an alkoxy group of 1 to 15 carbon atoms (e.g., methoxy, ethoxy, benzyloxy, phenetyloxy), an aryloxy group of 6 to 15 carbon atoms (e.g., phenoxy), an alkylthio group of 1 to 8 carbon atoms (e.g., methylthio, ethylthio), an arylthio group of 6 to 15 carbon atoms (e.g., phenylthio), an arylsulfonamido group of 6 to 12 carbon atoms (e.g., benzenesulfonamido), a ureido group, an alkylsulfonyl group of 1 to 8 carbon atoms (e.g., methanesulfonyl, ethylsulfonyl), an arylsulfonyl group of 6 to 15 carbon atoms (e.g., benzenesulfonyl, p-toluenesulfonyl), an aryl group of 6 to 15 carbon atoms (e.g., phenyl, 4-methylphenyl, 4-chlorophenyl, 2-naphthyl), a nitro group, a sulfo group, or a heterocyclic group of 6 to 15 carbon atoms (e.g., morpholino, 2-pyridyl).

$R^{17}$ and $R^{20}$ are each a hydrogen atom or an alkyl group (preferably, an alkyl group of 1 to 8 carbon atoms), an aryl group (preferably, an aryl group of 6 to 15 carbon atoms) or heterocyclic group (preferably; a heterocyclic group 5 to 15 carbon atoms). These groups may have substituents. Each of $R^{17}$ and $V^{10}$, and $R^{17}$ and $V^{17}$ may be combined to each other to form a ring. The substituent of the alkyl group is carboxyl, sulfo, halogen, hydroxyl, acetyl, amethylthio, a methoxy, methanesulfonamino, acetylamino or methanesulfonylcarbamoyl. The substituent of the aryl group is carboxyl, sulfo, cyano, nitro, hydroxyl, halogen, alkyl of 1 to 8 carbon atoms, alkoxy of 1 to 8 carbon atoms, aryloxy of not more than 15 carbon atoms, acyloxy of 1 to 8 carbon atoms, acyl of 1 to 8 carbon atoms, sulfamoyl of 1 to 8 carbon atoms, carbamoyl of 1 to 8 carbon atoms and aryl of not more than 15 carbon atoms. The preferred examples are the same as those mentioned for $Z^2$, $R^2$, $R^3$, $R^4$, $R^5$ and $R^6$ of the formula (I).

$Z^{13}$ is particularly preferable to be —CH=CH—.

From the methine compound of the above formula (II), various dyes can be obtained by varying the atomic group indicated by $Q^{11}$. Preferred examples of the dyes include amidinium ion type cyanine dye represented by the following formula (IV), dipolar amide type merocyanine dye having the following formula (V) and rhodacyanine dye having the following formula (VI) which is a combined dye of the cyanine dye and the merocyanine dye.

In the above formulas, $V^1$, $V^2$, $Z^{11}$, $Z^{12}$, $Z^{13}$, $L^{11}$ and $Y^{11}$ have the same meanings as defined in the formula (II).

$Z^{14}$ is an atomic group which forms a nitrogen-containing 5 or 6 membered heterocyclic ring together with "C=(CH—CH)$_{n1}$=N$^+$", and examples thereof are given below (in the following examples, the atomic groups are expressed, for convenience, by designations in the case where they are not quaternary salts):

thiazole nucleus (e.g., thiazole, 4-methylthiazole, 4-phenylthiazole, 4,5-dimethylthiazole, 4,5-diphneylthiazole), benzothiazole nucleus (e.g., benzothiazole, 4-chlorobenzothiazole, 5-chlorobenzothiazole, 6-chlorobenzothiazole, 5-nitrobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methylbenzothiazole, 6-methoxybenzothiazole, 5-ethoxybenzothiazole, 5-ethoxycarbonylbenzothiazole, 5-carboxybenzothiazole, 5-phenetylbenzothiazole, 6-fluorobenzothiazole, 5-chloro-6-methylbenzothiazole, 5,6-dimethylthiobenzothiazole, 5,6-dimethylbenzothiazole, 5-hydroxy-6-methylbenzothiazole, tetrahydrobenzothiazole, 4-phenylbenzothiazole), naphthothiazole nucleus (e.g., naphtho[2,1-d]thiazole, naphtho[1,2-d]thiazole, naphtho[2,3-d]thiazole, 5-methoxynaphtho[1,2-d]thiazole, 7-ethoxynaphtho[2,1-d]thiazole, 8-methoxynaphtho[2,1-d]thiazole, 8-methylthionaphtho[1,2-d]thiazole, 5-methoxynaphtho[2,3-d] thiazole, thiazoline nucleus (e.g., thiazoline, 4-methylthiazoline, 4-nitrothiazoline);

oxazole nucleus (e.g., oxazole, 4-methyloxazole, 4-nitrooxazole, 5-methyloxazole, 4-phenyloxazole, 4,5-diphenyloxazole, 4-ethyloxazole), benzoxazole nucleus (e.g., benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-niyrobenzoxazole, 5-trifluoromethylbenzoxazole, 5-hydrobenzoxazole, 5-carboxybenzoxazole, 6-methylbenzoxazole, 6-chlorobenzoxazole, 6-nitrobenzoxazole, 6-methoxybenzoxazole, 6-hydroxybenzoxazole, 5,6-dimethylbenzoxazole, 4,6-dimethylbenzoxazole, 5-ethoxybenzoxazole), naphthoxazole nucleus (e.g., naphtho[2,1-d]oxazole, naphtho[1,2-d]oxazole, naphtho[2,3-d]oxazole, 5-nitronaphtho[2,1-d]oxazole), oxazoline nucleus (e.g., 4,4-dimethyloxazoline);

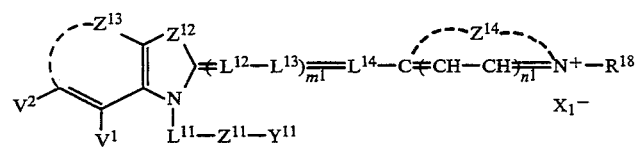

(IV)

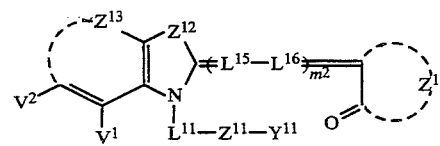

(V)

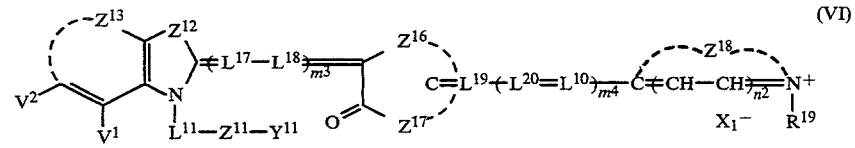

(VI)

selenazole nucleus (e.g., 4-methylselenazole, 4-nitroselenazole, 4-phenylselenazole), benzoselenazole nucleus (e.g., benzoselenazole, 5-chlorobenzoselenazole, 5-nitrobenzoselenazole, 5-methoxybenzoselenazole, 5-hydroxybenzoselenazole, 6-nitrobenzoselenazole, 5-chloro-6-nitrobenzoselenazole), naphthoselenazole nucleus (e.g., naphtho[2,1-d]selenazole, naphtho[1,2-d]selenazole), 3,3-dialkylindolenine nucleus (e.g., 3,3-dimethylindolenine, 3,3-diethylindolenine, 3,3-dimethyl-5-cyanoindolenine, 3,3-dimethyl-6-nitroindolenine, 3,3-dimethyl-5-nitroindolenine, 3,3-dimethyl-5-methoxyindolenine, 3,3,5-trimethylindolenine, 3,3-dimethyl-5-chloroindolenine);

imidazole nucleus (e.g., 1-alkylimidazole, 1-alkyl-4-phenylimidazole, 1-alkylbenzimidazole, 1-alkyl-5-chlorobenzimidazole, 1-alkyl-5,6-dichlorobenzimidazole, 1-alkyl-5-methoxybenzimidazole, 1-alkyl-5-cyanobenzimidazole, 1-alkyl-5-fluorobenzimidazole, 1-alkyl-5-trifluoromethylbenzimidazole, 1-alkyl-6-chloro-5-cyanobenzimidazole, 1-alkyl-6-chloro-trifluoromethylbenzimidazole, 1-alkylnaphtho[1,2-d]imidazole, 1-allyl-5,6-dichlorobenzimidazole, 1-arylimidazole, 1-arylbenzimidazole, 1-aryl-5-chlorobenzimidazole, 1-aryl-5,6-dichlorobenzimidazole, 1-aryl-5-methoxybenzimidazole, 1-aryl-5-cyanobenzimidazole, 1-arylnaphtho[1,2-d]imidazole, {The alkyl groups which are substituent groups of the above-mentioned heterocyclic rings are preferably alkyl groups of 1 to 8 carbon atoms, for example, unsubstituted alkyl groups such as methyl, ethyl, propyl, isopropyl and butyl, and hydroxyalkyl groups (e.g., 2-hydroxyethyl, 3-hydroxypropyl). Particularly preferred are methyl and ethyl. The above aryl group is phenyl, phenyl substituted with halogen (e.g., chlorine), phenyl substituted with alkyl of 1 to 8 carbon atoms (e.g., methyl) and phenyl substituted with alkoxy of 1 to 8 carbon atoms (e.g., methoxy)};

pyridine nucleus (e.g., 2-pyridine, 4-pyridine, 5-methyl-2-pyridine, 3-methyl-4-pyridine), quinoline nucleus (e.g., 2-quinoline, 3-methyl-2-quinoline, 5-ethyl-2-quinoline, 6-methyl-2-quinoline, 6-nitro-2-quinoline, 8-fluoro-2-quinoline, 6-methoxy-2-quinoline, 6-hydroxy-2-quinoline, 8-chloro-2-quinoline, 4-quinoline, 6-ethoxy-4-quinoline, 6-nitro-4-quinoline, 8-chloro-4-quinoline, 8-fluoro-4-quinoline, 8-methyl-4-quinoline, 8-methoxy-4-quinoline, isoquinoline, 6-nitro-1-isoquinoline, 3,4-dihydro-1-isoquinoline, 6-nitro-3-isoquinoline), imidazo[4,5-b]quinoxaline nucleus (e.g., 1,3-diethylimidazo[4,5-b]quinoxaline, 6-chloro-1,3-diallylimidazo[4,5-b]-quinoxaline), benzotellurazole nucleus (e.g., benzotellurazole, 5-methylbenzotellurazole, 5-methoxybenzotellurazole), naphthotellurazole nucleus (e.g., naphtho[1,2-d]tellurazole), oxadiazole nucleus, thiadiazole nucleus, tetrazole nucleus, pyrimidine nucleus.

$Z^{15}$ is an atomic group which forms a nitrogen-containing 5 or 6-membered heterocyclic ring together with "C—CO", and examples thereof include rhodanine nucleus, 2-thiohydantoin nucleus, 2-thiooxazolidine-4-one nucleus, 2-pyrazoline-5-one nucleus, barbituric acid nucleus, 2-thiobarbituric acid nucleus, thiazolidine-2,4-dione nucleus, thiazolidine-4-one nucleus, isooxazolone nucleus, hydantoin nucleus and indandione nucleus.

$Z^{15}$ may be of ring-opening type having a structure that a ring derived from acetylacetone, malondinitrile, ethyl acetoacetate, ethyl cyanoacetate or the like is opened.

Examples of the 5 or 6-membered substituent groups formed by $Z^{15}$ include an alkyl group, a substituted alkyl group, an aryl group, a substituted aryl group and a heterocyclic group. Preferred examples thereof include an alkyl group of 1 to 18 carbon atoms (e.g., methyl, ethyl, propyl, isopropyl, butyl, isobutyl, hexyl, octyl, dodecyl, octadecyl; more preferably, an alkyl group of 1 to 7 carbon atoms, particularly preferably an alkyl group of 1 to 4 carbon atoms), a substituted alkyl group of 1 to 18 carbon atoms (e.g., aralkyl such as benzyl or 2-phenylethyl), a hydroxyalkyl group of 1 to 18 carbon atoms (e.g., 2-hydroxyethyl, 3-hydroxypropyl), a carboxylalkyl group of 1 to 18 carbon atoms (e.g., 2-carboxyethyl, 3-carboxypropyl, 4-carboxybutyl, carboxymethyl), an alkoxyalkyl group of 1 to 18 carbon atoms (e.g., 2-methoxyethyl group, 2-(2-methoxyethoxy)ethyl group), a sulfoalkyl group of 1 to 18 carbon atoms (e.g., 2-sulfoethyl, 3-sulfopropyl, 3-sulfobutyl, 4-sulfobutyl, 2-[3-sulfopropoxy]ethyl, 2-hydroxy-3-sulfopropyl, 3-sulfopropoxyethoxyethyl), a sulfatoalkyl group of 1 to 18 carbon atoms (e.g., 3-sulfatopropyl, 4-sulfatobutyl), a heterocyclic substituted alkyl group of 1 to 18 carbon atoms (e.g., 2-(pyrrolidine-2-one-1-yl)ethyl, tetrahydrofurfuryl, 2-morpholinoethyl), 2-acetoxyethyl, carbomethoxymethyl, 2-methanesulfonylaminoethyl, allyl, an aryl group of 6 to 14 carbon atoms (e.g., phenyl group, 3-naphthyl group), a substituted aryl group (e.g., 4-carboxyphenyl group, 4-sulfophenyl group, 3-chlorophenyl group, 3-methylphenyl group), and a heterocyclic group of 5 to 14 carbon atoms (e.g., 2-pyridyl, 2-thiazolyl).

Each of $Z^{16}$ and $Z^{17}$ is an atomic group which forms a nitrogen-containing 5 or 6 membered heterocyclic ring together with "C—CO" and "C", and the 5 or 6-membered rings formed by $Z^{16}$ and $Z^{17}$ together with "C—CO" are the same as those obtained by removing oxo group or thioxo group from the 5 or 6-membered rings formed by $Z^{15}$.

Each of $L^{12}$, $L^{13}$, $L^{14}$, $L^{15}$, $L^{16}$, $L^{17}$, $L^{18}$, $L^{19}$, $L^{20}$ and $L^{10}$ is a methine group or a substituted methine group. Examples of the substituent groups thereof include an alkyl group of 1 to 8 carbon atoms (e.g., methyl, ethyl), an aryl group of 6 to 14 carbon atoms (e.g., phenyl), an aralkyl group of 6 to 14 carbon atoms (e.g., benzyl), an alkoxy group of 1 to 8 carbon atoms (e.g., methoxy, ethoxy), an aryloxy group of 6 to 14 carbon atoms (e.g., phenoxy), an alkylthio group of 1 to 8 carbon atoms (e.g., methylthio, ethylthio), an arylthio group of 6 to 14 carbon atoms (e.g., phenylthio), or a halogen atom (e.g., chlorine, bromine). The substituent groups of the methyl may be combined each other to form a 4 to 6-membered ring.

$Z^{18}$ has the same meaning as that of $Z^{14}$.

Each of $R^8$ and $R^9$ is an alkyl group which may be substituted, for example, an alkyl group of 1 to 18 carbon atoms, preferably an alkyl group of 1 to 7 carbon atoms, particularly preferably an alkyl group of 1 to 4 carbon atoms. Examples of the unsubstituted alkyl group include methyl, ethyl, propyl, isopropyl, butyl, isobutyl, hexyl, octyl, dodecyl and octadecyl. Examples of the substituted alkyl group include an aralkyl group of 7 to 14 carbon atoms (e.g., benzyl, 2-phenylethyl), a hydroxyalkyl group of 1 to 18 carbon atoms (e.g., 2-hydroxyethyl, 3-hydroxypropyl), a carboxyalkyl group of 1 to 18 carbon atoms (e.g., 2-carboxyethyl, 3-carboxypropyl, 4-carboxybutyl, carboxymethyl), an alkoxyalkyl group of 1 to 18 carbon atoms (e.g., 2-methoxyethyl, 2-(2-methoxyethoxy) ethyl), a sulfoalkyl group of 1 to 18 carbon atoms (e.g., 2-sulfoethyl, 3-sulfopropyl, 3-sulfobutyl, 4-sulfobutyl, 4-sulfo-3-methylbutyl, 2-(3-sulfopropoxy) ethyl), 2-hydroxy-3-sulfopropyl, 3-sulfopropoxyethoxyethyl), a sulfatoalkyl group of 1 to 18 carbon atoms (e.g., 3-sulfatopropyl, 4-sulfatobutyl), a heterocyclic ring substituted alkyl group of 5 to 14 carbon atoms (e.g., 2-(pyrrolidine-2-one-1-yl)ethyl, tetrahydrofurfuryl), 2-acetoxyethyl, carbomethoxymethyl, 2-methanesulfonylaminoethyl and allyl group. $R^8$ or $R^9$ may form a ring containing methine group of the α position of these groups.

Each of $n^1$ and $n^2$ is 0 or 1; each of $m^1$ and $m^4$ is an integer of 0 to 5; and each of $m^2$ and $m^3$ is an integer of 1 to 5.

$X_1^-$ is a counter anion of quaternary salt. This serves to supply negative electric charge necessary for neutralizing the electric charge of the quaternary nitrogen cation, and is not always monovalent. Preferred examples of the counter anions include halogen ions such as $F^-$, $Cl^-$, $Br^-$ and $I^-$; $SO_4^{2-}$, $HSO_4^-$, and alkyl sulfuric acid ions such as $CH_3OSO_3^-$; sulfonic acid ions such as paratoluenesulfonic acid ion, methanesulfonic acid ion and trifluoromethanesulfonic acid ion; caboxylic acid ions such as acetic acid ion, trifluoroacetic acid ion and oxalic acid ion; and $PF_6^-$, $BF_4^-$, $ClO_4^-$, $IO_4^-$, $PO_4^{3-}$, $NO_3^-$ and phenolate ions such as picric acid ion.

Of various methine compounds represented by the formula (II), a cyanine dye of the following formula (VII) is particularly preferred as the decoloration dye of the photographic light-sensitive material.

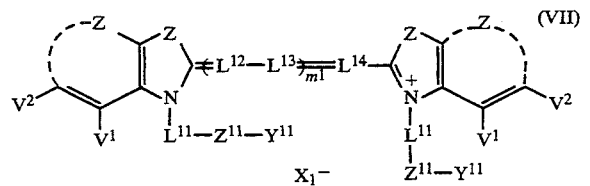

(VII)

In the above formula, $V^1$, $V^2$, $Z^{11}$, $Z^{12}$, $Z^{13}$, $L^{11}$, $L^{12}$, $L^{13}$, $L^{14}$, $Y^{11}$, $m^1$ and $X_1^-$ have the same meanings as defined in the above formula (IV).

In the compounds having the formula (I), (II) or (III) employable for the silver halide photographic material of the invention, the methine compound having the following formula (III) as well as the formula (II) is a novel compound, and is preferably employed for the material of the invention.

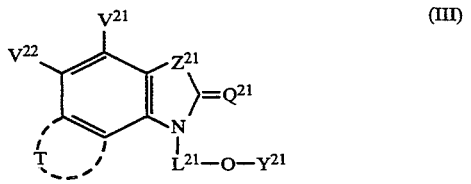

(III)

In the formula (III), $Y^{21}$ is the same group as one defined for $Y^1$ of the formula (I).

$Q^{21}$ is the same group as that defined for $Q^1$ of the formula (I).

$L^{21}$ is the same group as that defined for $L^{11}$ of the formula (II).

$V^{21}$ and $V^{22}$ independently represents a hydrogen atom, an alkyl group which may be substituted with carboxyl, sulfo or halogen, a halogen atom, an acyl group, an acyloxy group, an alkoxycarbonyl group, a carbamoyl group, a sulfamoyl group, a sulfo group, a carboxyl group, a cyano group, a hydroxy group, an amino group, an acylamino group, an alkoxy group, an aryloxy group, an alkylthio group, an arylthio group, a sulfonamide group, a ureido group, an alkylsulfonyl group, an arylsulfonyl group, an aryl group which may be substituted with halogen or methyl, or a heterocyclic ring.

Each of $V^{21}$ and $V^{22}$ generally is an alkyl group of 1 to 18 carbon atoms which may be substituted with carboxyl, sulfo or halogen (e.g., methyl, ethyl, propyl), a halogen atom (e.g., chlorine, bromine), an acyl group of 1 to 8 carbon atoms (e.g., acetyl), an acyloxy group of 1 to 8 carbon atoms (e.g., acetyloxy), an alkoxycarbonyl group of 1 to 8 carbon atoms (e.g., methoxycarbonyl), a carbamoyl group of 1 to 8 carbon atoms (e.g., N-methylcarbamoyl), a sulfamoyl group of 1 to 8 carbon atoms (e.g., N-methylsulfamoyl), a carboxyl group, a cyano group, a hydroxyl group, an amino group of 1 to 8 carbon atoms (e.g., amino, methylamino, dimethylamino), an acylamino group of 1 to 8 carbon atoms (e.g., acetylamino), an alkoxy group of 1 to 15 carbon atoms (e.g., methoxy, ethoxy, benzyloxy, phenetyloxy), an aryloxy group of 6 to 15 carbon atoms (e.g., phenoxy), an alkylthio group of 1 to 8 carbon atoms (e.g., methylthio, ethylthio), an arylthio group of 6 to 15 carbon atoms (e.g., phenylthio), a sulfonamido group, an alkylsulfonyl group of 1 to 8 carbon atoms (e.g., methanesulfonyl, ethylsulfonyl), an arylsulfonyl group of 6 to 15 carbon atoms (e.g., benzenesulfonyl, p-toluenesulfonyl), an aryl group of 6 to 15 carbon atoms which may be substituted with halogen or methyl (e.g., phenyl, 4-methylphenyl, 4-chlorophenyl, 2-naphthyl), a sulfo group, or a heterocyclic group of 15 or less carbon atoms (e.g., morpholino, 2-pyridyl).

Preferred examples of the group indicated by $V^{21}$ or $V^{22}$ are a hydrogen atom, a methyl group, a methoxy group, a methylthio group and a halogen atom. Particularly preferred is a hydrogen atom.

$V^{21}$ and $V^{22}$ may be combined to each other to form a cyclohexene ring, an aromatic ring or a heterocyclic ring, so as to form a condensed ring together with the benzene ring having $V^1$ and $V^2$.

$Z^{21}$ represents —O—; —S—; —Se—;

—$NR^{22}$— in which $R^{22}$ represents a hydrogen atom, an alkyl group which may be substituted with carboxyl, sulfo, halogen, hydroxyl, acetyl, methylthio, methoxy, methanesulfonamino, acetylamino group or methanesulfonylcarbamoyl, an aryl group which may be substituted with carboxyl, sulfo, cyano, nitro, halogen, hydroxyl, alkyl, alkoxy, aryloxy, acyloxy, acyl, sufamoyl, carbamoyl, or an aryl group or a heterocyclic group;

—$CR^{23}R^{24}$— in which each of $R^{23}$ and $R^{24}$ independently represents a hydrogen atom or an alkyl group which may have a substituent, said substituent being a carboxyl group, a sulfo group, a halogen atom, a hydroxyl group, an acetyl group, a methylthio group, a methoxy group, a methanesulfonamino group, an acetylamino group or a methanesulfonylcarbamoyl group; or —$CV^{23}=V^{24}$— in which $V^{23}$ represents the same group as that of $V^{21}$ and $V^{24}$ represents the same group as that of $V^{21}$.

$R^{22}$ is each generally a hydrogen atom, an alkyl group of 1 to 18 carbon atoms which may be substiteted with the above group, or an aryl group of 6 to 15 carbon atoms which may be substiteted with the above group.

Preferred examples of the alkyl group include methyl, ethyl, propyl, butyl, isobutyl, hexyl, octyl, dodecyl and octadecyl. Preferred examples of the aryl group which may be substituted are phenyl, 2-naphthyl and 1-naphthyl. Preferred examples of the substituents are carboxyl, sulfo, cyano, nitro, halogen, hydroxyl, alkyl of 1 to 8 carbon atoms (e.g., methyl, ethyl), alkoxy of 1 to 8 carbon atoms (e.g., methoxy, ethoxy), aryloxy of 6 to 15 carbon atoms (e.g., phenoxy), acyloxy of 1 to 8 carbon atoms (e.g., acetyloxy), acyl of 1 to 8 carbon atoms, sufamoyl of 1 to 8 carbon atoms, carbamoyl, or aryl group of 6 to 15 carbon atoms (e.g., phenyl). The heterocyclic group is generally a group of 5 to 15 carbon atoms. Preferred examples of the group are 2-pyridyl, 2-thiazolyl, 2-furyl and 2-thiophenyl.

$R^{22}$ is preferred to be unsubstituted alkyl of 1 to 8 carbon atoms (e.g., methyl, ethyl, propyl, butyl) or unsubstituted aryl of 6 to 15 carbon atoms (e.g., phenyl, 1-naphthyl). Particularly preferred is methyl, ethyl or phenyl.

Each of $R^{23}$ and $R^{24}$ is generally an alkyl group of 1 to 8 carbon atoms (e.g., methyl, ethyl, propyl, butyl, isobutyl, hexyl, octyl, dodecyl or octadecyl) which may be substituted with the above group. Further, $R^{23}$ and $R^{24}$ may be combined to each other to form a ring. Examples of the ring include cyclohexene ring, 4-pyridine ring and 4-(N-methyl)piperidine ring. $R^{23}$ and $R^{24}$ is particularly preferred to be methyl.

T represents a group to form an aromatic ring, an aliphatic ring or a heterocyclic ring together with a hydrocarbon group of a benzene ring to which T is attached. The aromatic ring is preferred to be a benzene ring (the substituent include the groups shown in $V^{21}$ or $V^{22}$). The aliphatic ring is preferred to be cyclohexene ring. The heterocyclic ring is preferred to be a furan ring, a thiophene ring, a pyrrole ring, a thiazole ring, an oxazole ring, an imidazole ring and a triazole ring. Particularly preferred is a benzene ring.

From the methine compound of the above formula (III), various dyes can be obtained by varying the atomic group indicated by $Q^{21}$. Preferred examples of the dyes include amidinium ion type cyanine dye represented by the following formula (VIII), dipolar amide type merocyanine dye of the following formula (IX) and rhodacyanine dye of the following formula (X) which is a combined dye of the cyanine dye and the merocyanine dye.

Hence, the methine compound (III) preferably is represented by the following formula (VIII), (IX) or (X):

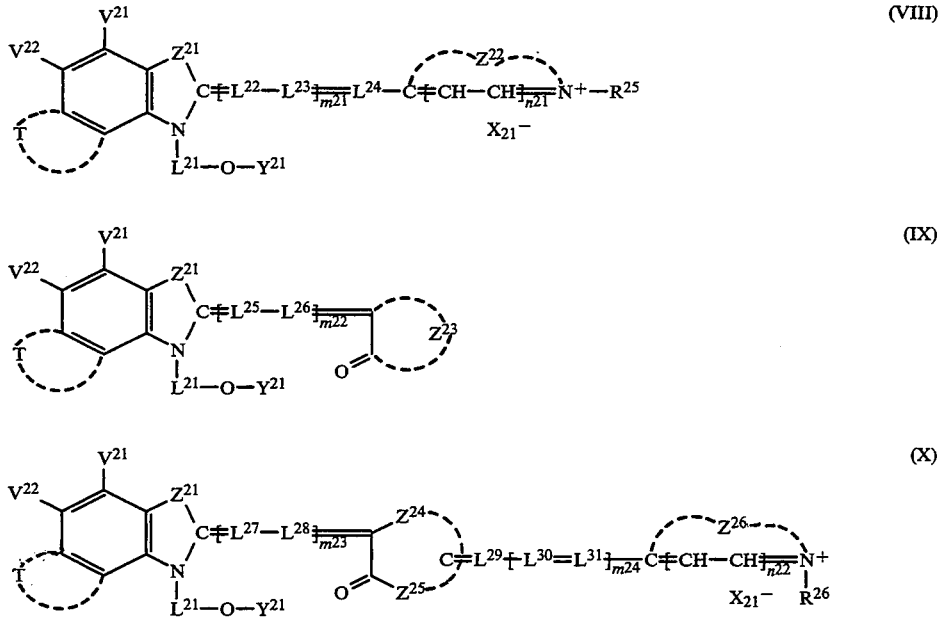

In the formulae (VIII) to (X), $V^{21}$, $V^{22}$ $Z^{21}$, T, $L^{21}$ and $Y^{21}$ have the meanings defined in the above formula (III).

$Z^{22}$ represents a group to form a 5- or 6-membered nitrogen atom-containing heterocyclic ring together with "C=(CH—CH)$_{n23}$=N+". As examples of the heterocyclic ring, there can be mentioned the same rings as those mentioned for $Z^{14}$.

$Z^{23}$ represents a group to form a 5- or 6-membered nitrogen atom-containing heterocyclic ring together with "C=CO". As examples of the heterocyclic ring, there can be mentioned the same rings as those mentioned for $Z^{15}$.

$Z^{24}$ and $Z^{25}$ represent a group to form a 5- or 6-membered nitrogen atom-containing heterocyclic ring together with "C=CO" and "C", and the 5 or 6-membered rings formed by $Z^{24}$ and $Z^{25}$ together with "C—CO" and "C" are the same as those obtained by removing oxo group or thioxo group from the 5- or 6-membered rings formed by $Z^{23}$.

Each of $L^{22}$, $L^{23}$, $L^{24}$, $L^{25}$, $L^{26}$, $L^{27}$, $L^{28}$, $L^{29}$, $L^{30}$ and $L^{31}$ represents a methine group or a substituted methine group. As examples of the substituents, there can be mentioned the same groups as those mentioned for $L^{12}$, $L^{13}$, $L^{14}$, $L^{15}$, $L^{16}$, $L^{17}$, $L^{18}$, $L^{19}$, $L^{20}$ and $L^{10}$.

$Z^{26}$ has the same meaning as that of $Z^{22}$.

Each of $R^{25}$ and $R^{26}$ is an alkyl group which may be substituted. As examples of the substituents, there can be mentioned the same groups as those mentioned for $R^{18}$ and $R^{19}$.

$n^{21}$ and $n^{22}$ represent 0 or 1, $m^{21}$ and $m^{24}$ represent an integer of 0 to 5, $m^{22}$ and $m^{23}$ represent an integer of 1 to 5, and $X_{21}^-$ represents an anion to form a pair with a quaternary ammonium ion. As examples of the anions, there can be mentioned the same anions as those mentioned for $X_1^-$.

Of various methine compounds represented by the formula (III), a cyanine dye of the following formula (XI) is particularly preferred as the decoloration dye of the photographic light-sensitive material of the invention.

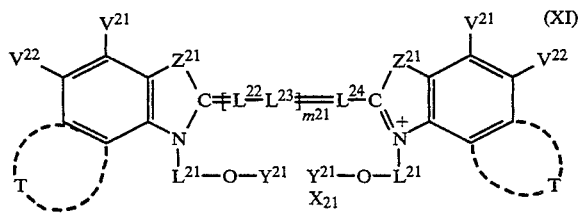

In the formula (XI), $V^{21}$, $V^{22}$, $Z^{21}$, T, $L^{21}$, $L^{22}$, $L^{23}$, $L^{24}$, $Y^{21}$, $X_{21}^-$ and $m^{21}$ have the meanings defined in the above formula (VIII).

Examples of the methine compounds represented by the formulae (I), (II) or (III) are given below. In the following formulas, some have a nitrogen cation ($N^+$) on the right side and some have it on the left hand, for convenience sake, but there is no difference in the structure because of resonance even if the cation is placed on the right side or the left side.

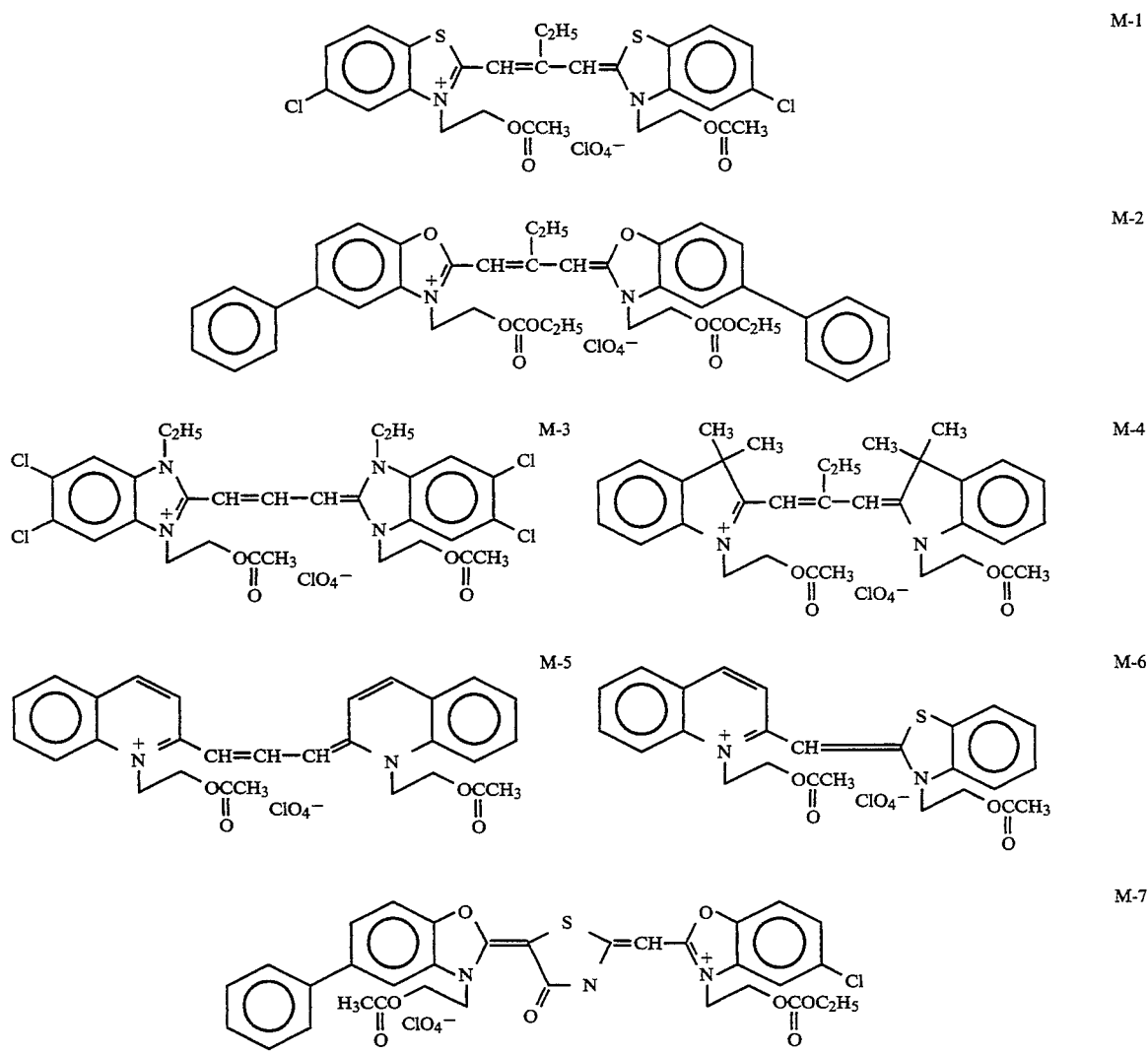

-continued
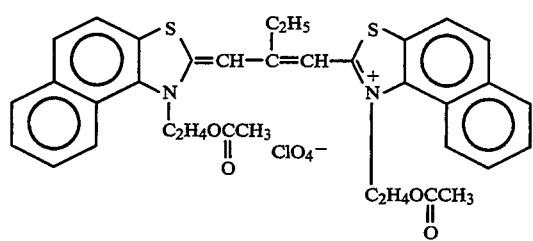
M-8
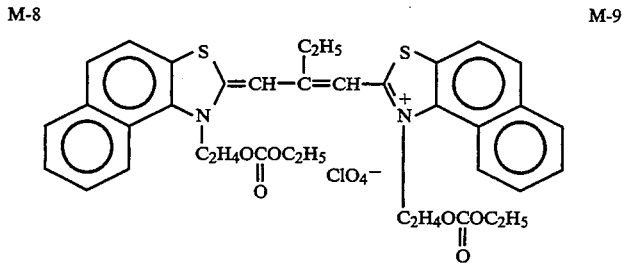
M-9
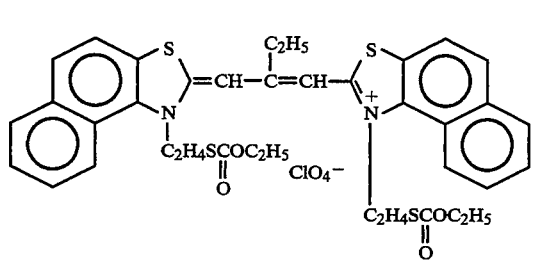
M-10
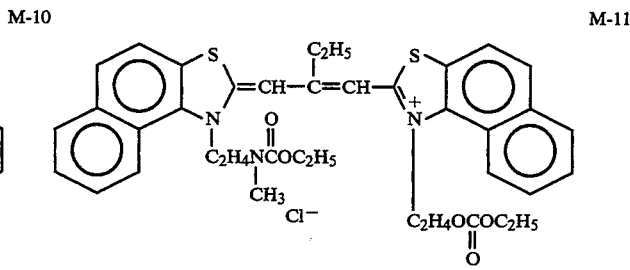
M-11
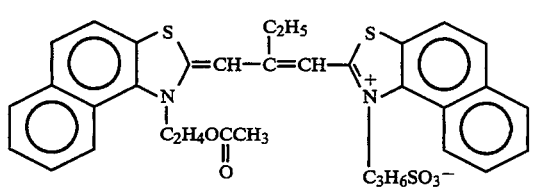
M-12
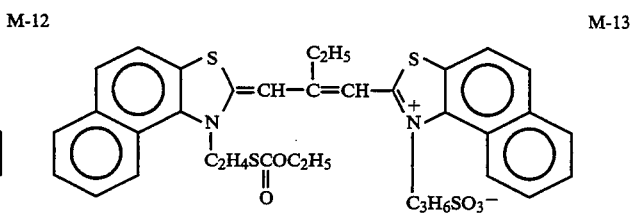
M-13
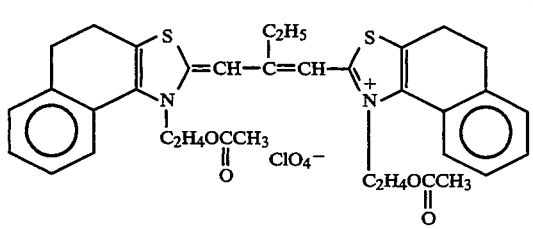
M-14
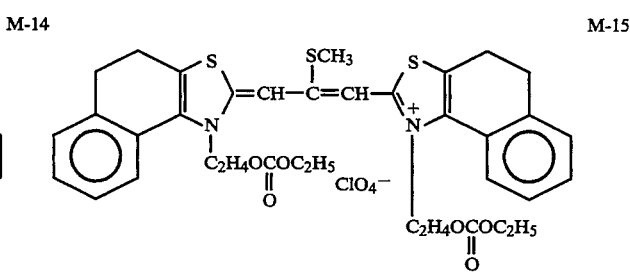
M-15
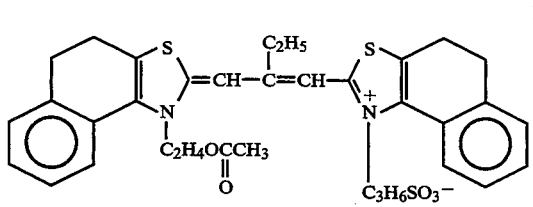
M-16
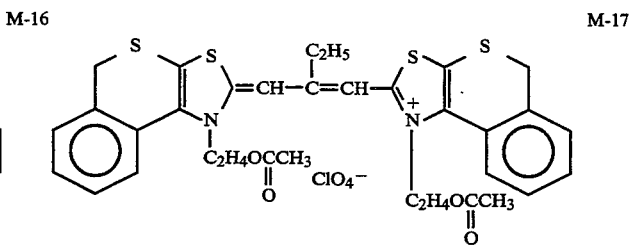
M-17
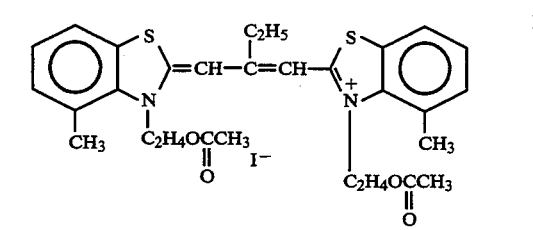
M-18
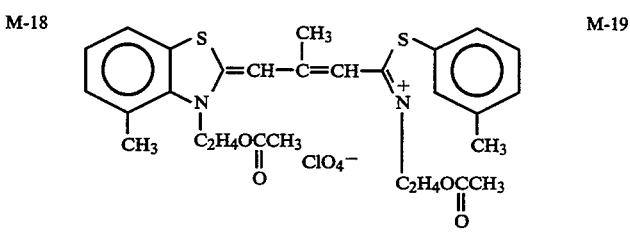
M-19

-continued
M-20 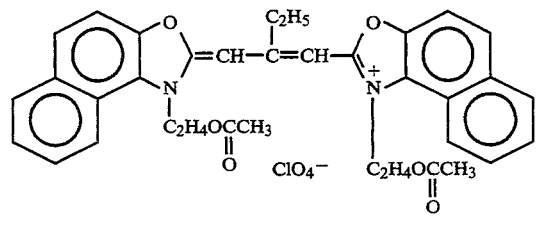 M-21 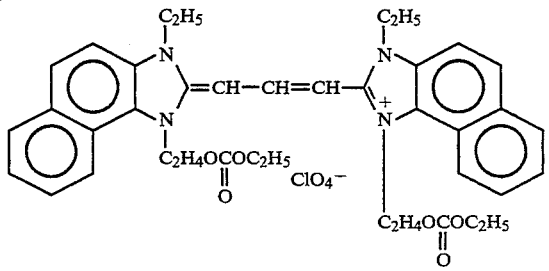
M-22 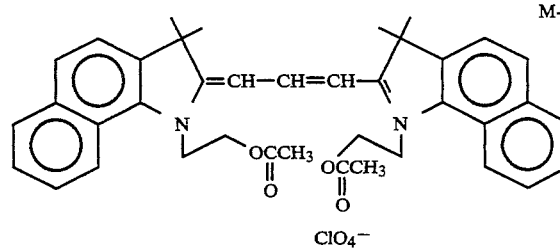 M-23 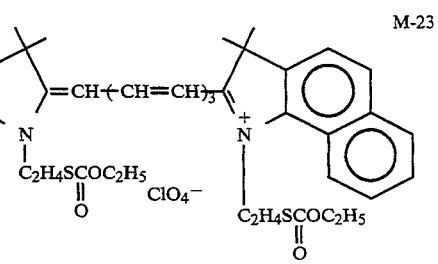
M-24 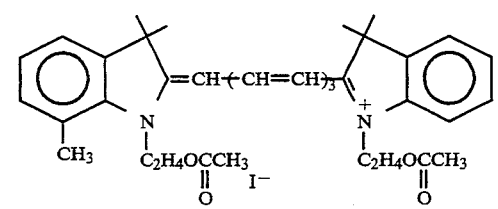 M-25 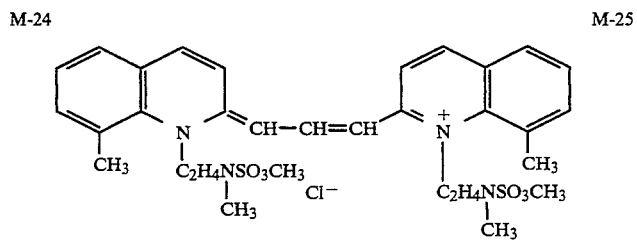
M-26 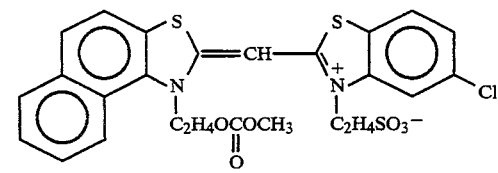 M-27 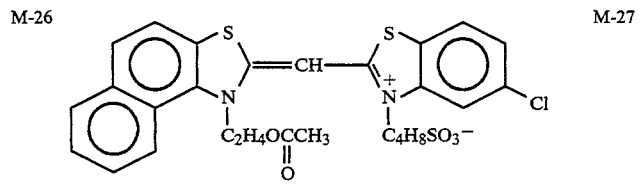
M-28 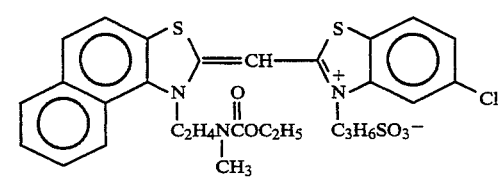 M-29 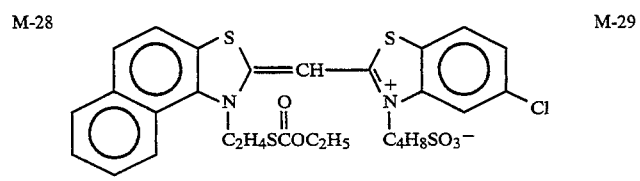
M-30 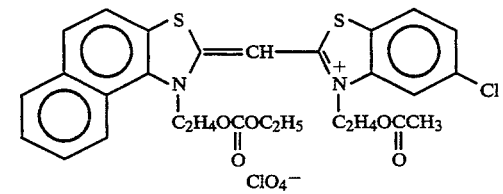 M-31 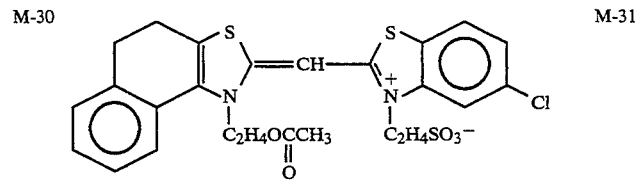
M-32 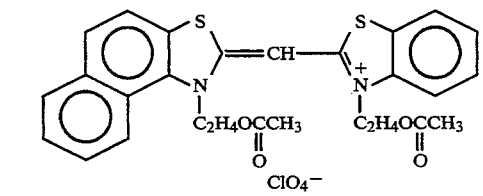 M-33 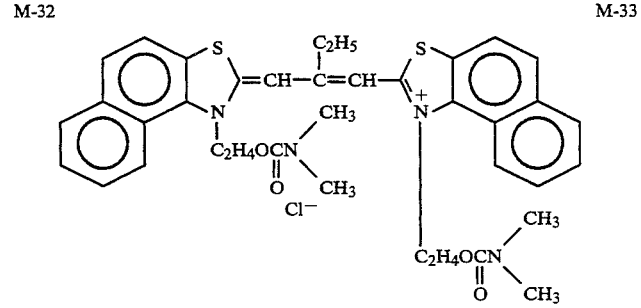

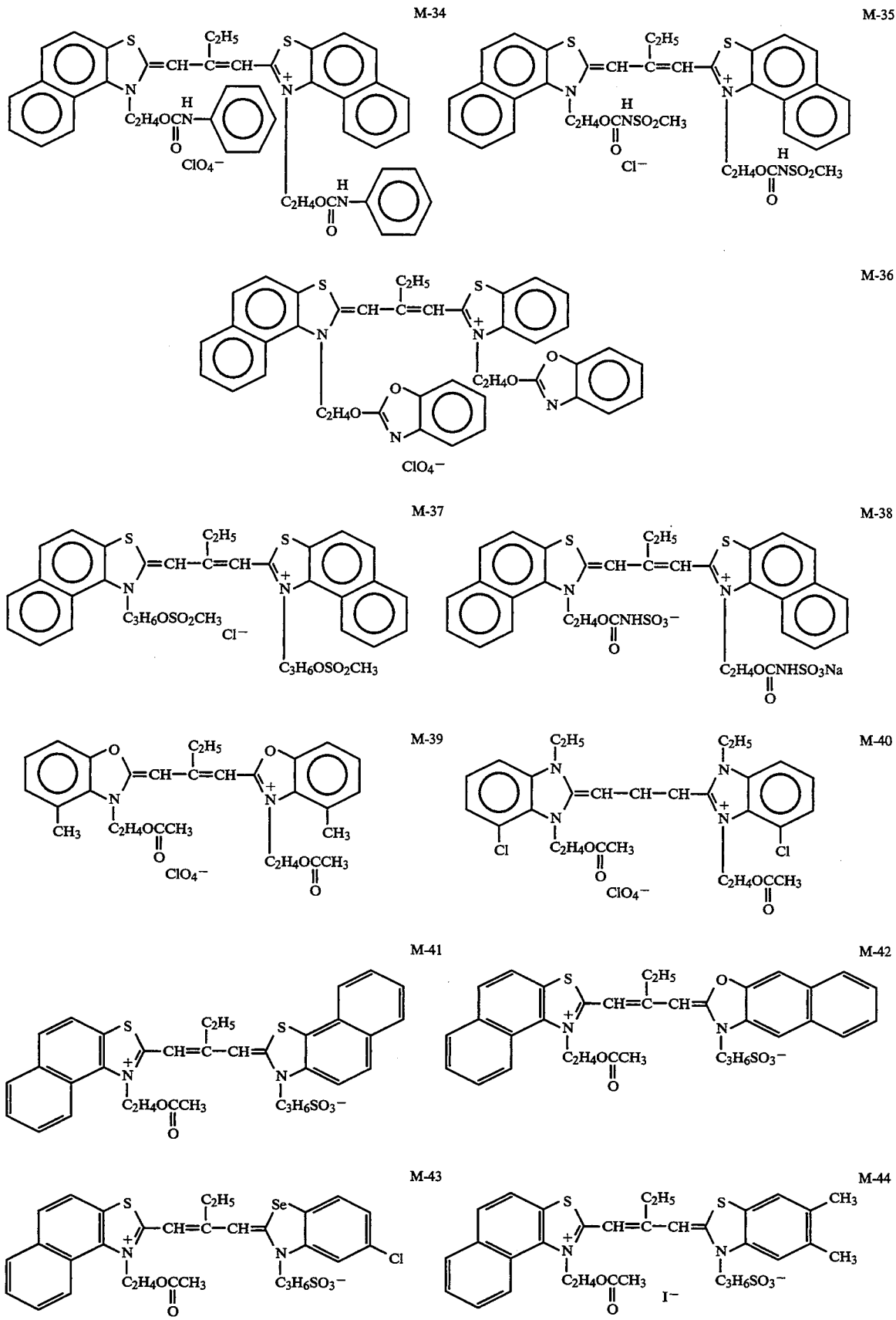

-continued
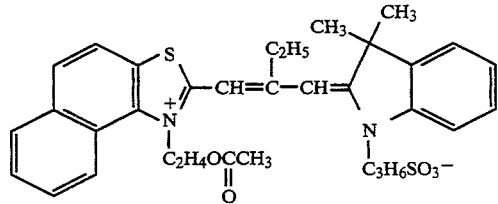 M-45
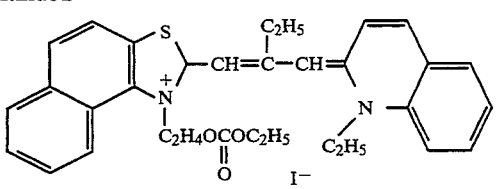 M-46
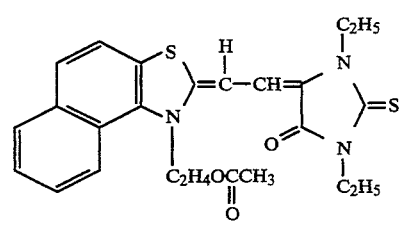 M-47
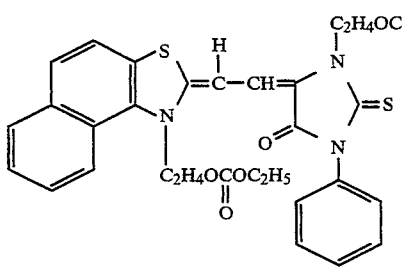 M-48
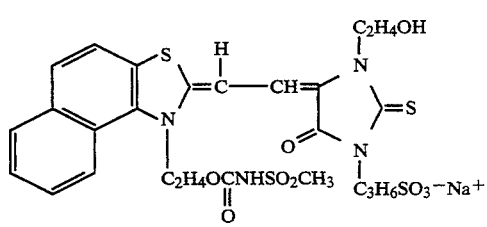 M-49
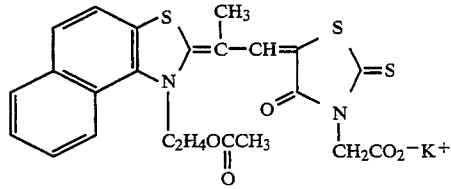 M-50
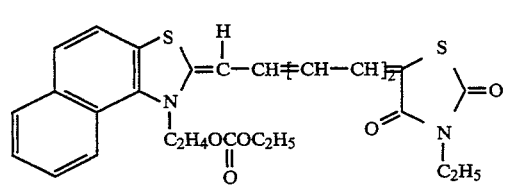 M-51
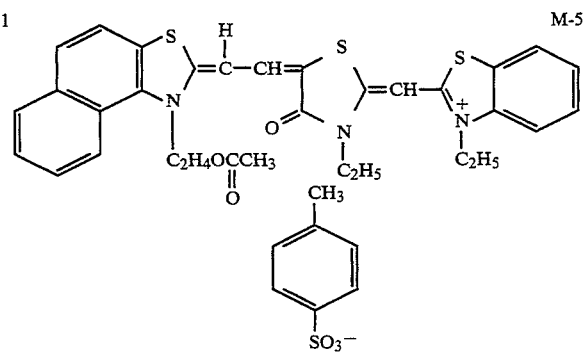 M-52
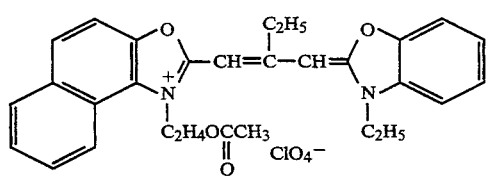 M-53
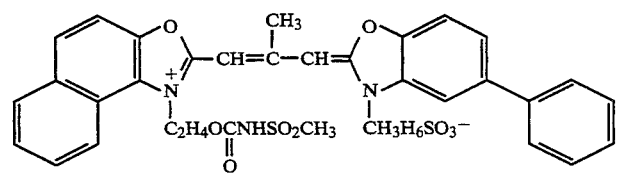 M-54
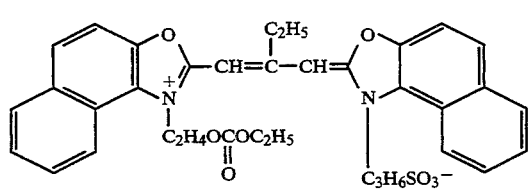 M-55
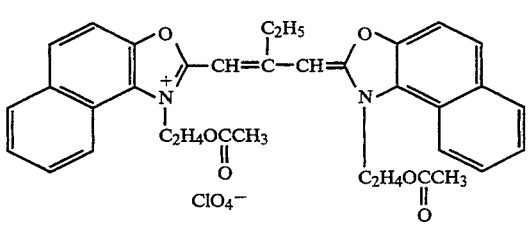 M-56

-continued
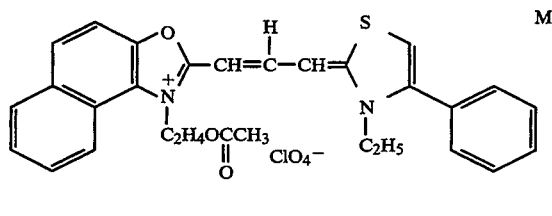 M-57
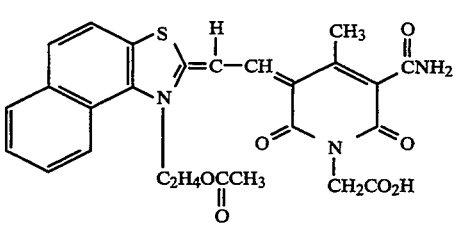 M-58
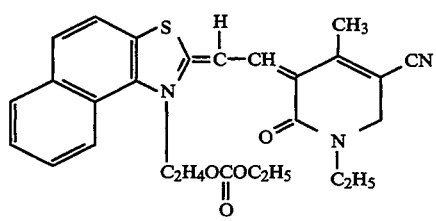 M-59
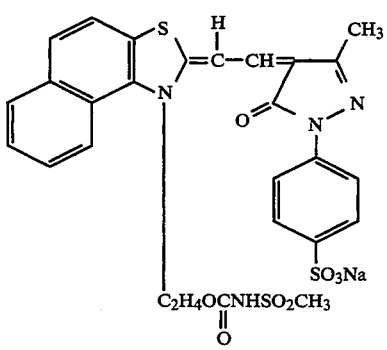 M-60
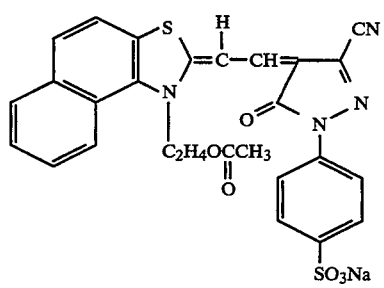 M-61
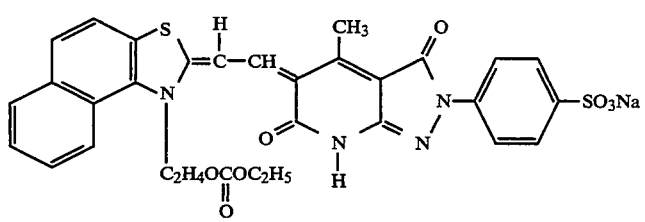 M-62
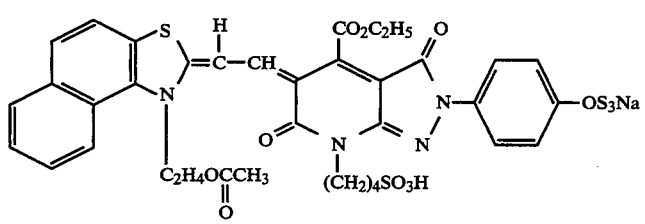 M-63
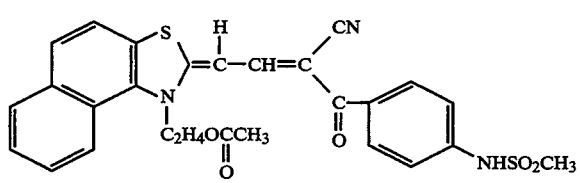 M-64

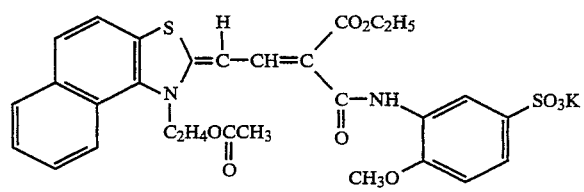
M-65
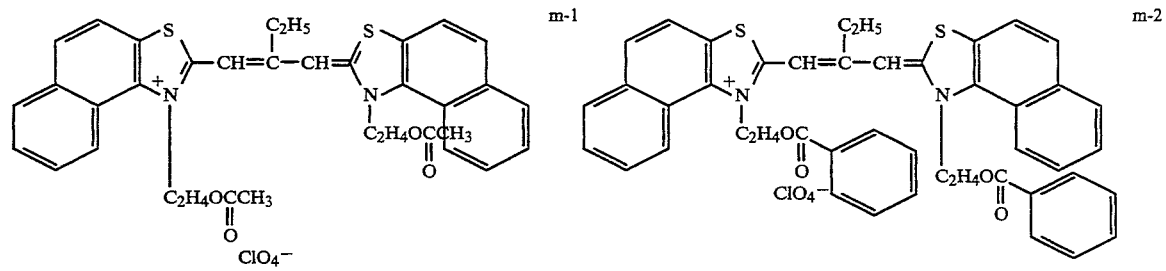
m-1 m-2
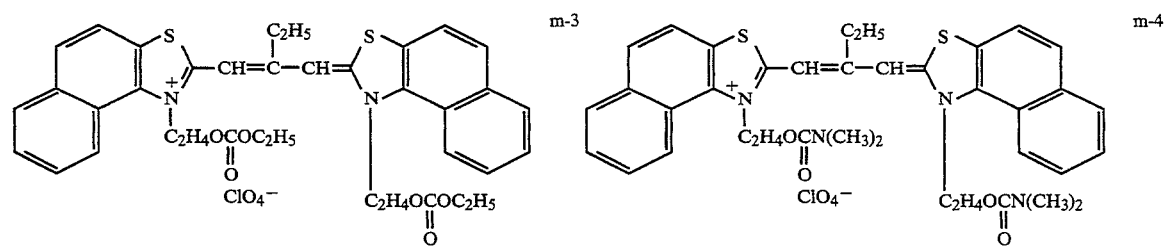
m-3 m-4
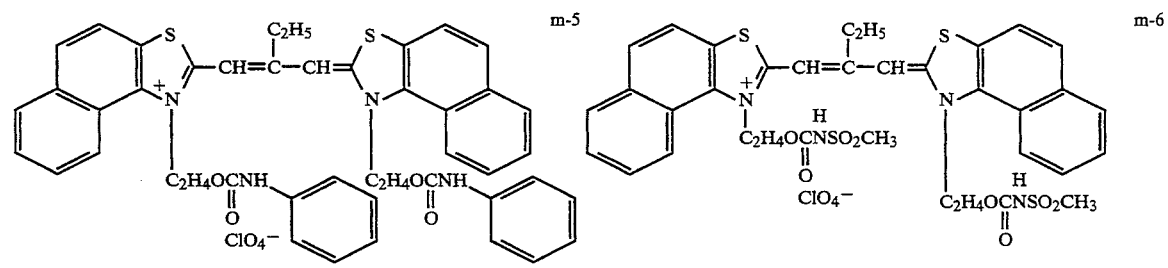
m-5 m-6
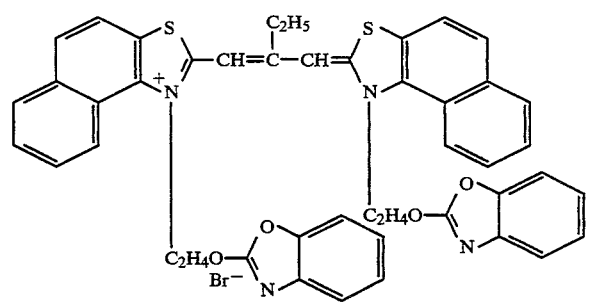
m-7
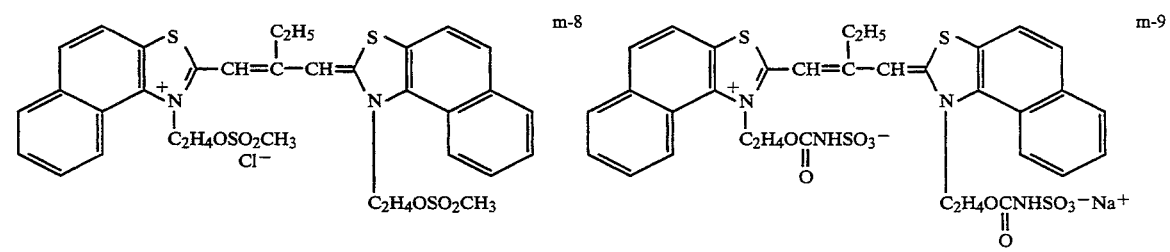
m-8 m-9

-continued
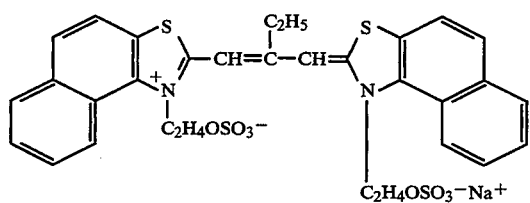
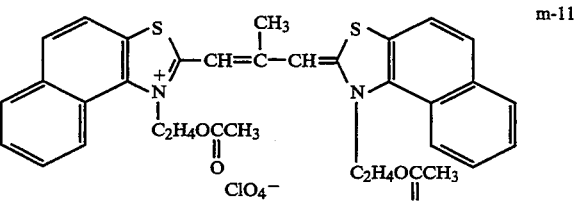
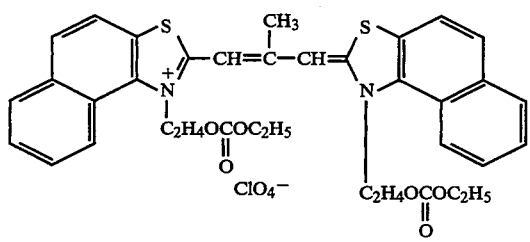
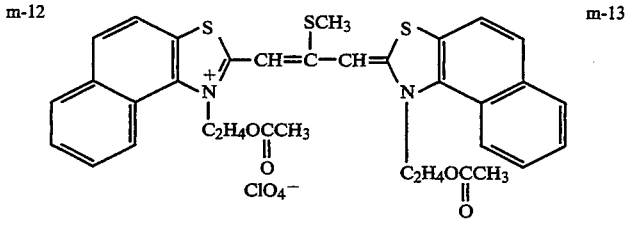
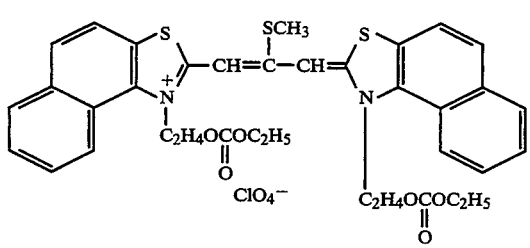
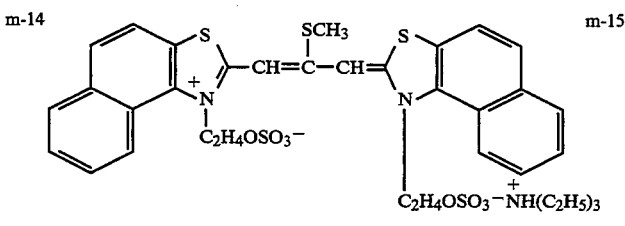
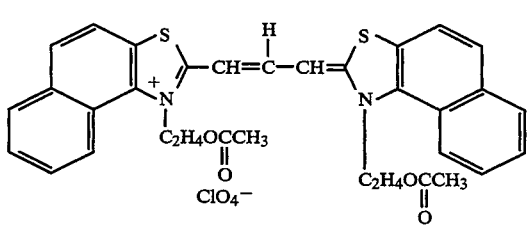
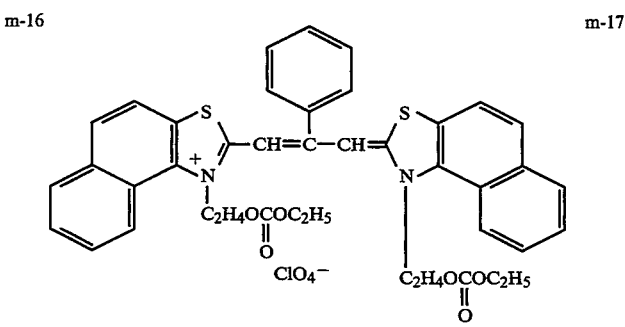
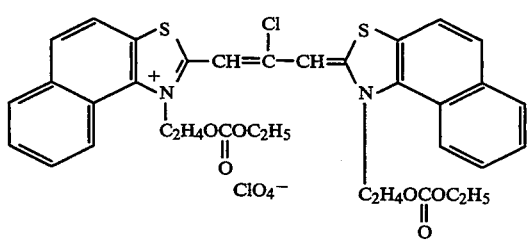
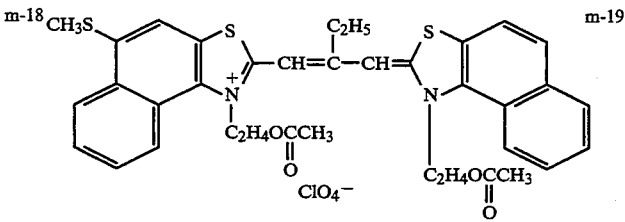
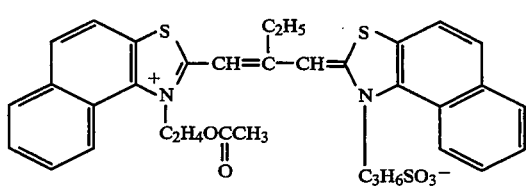
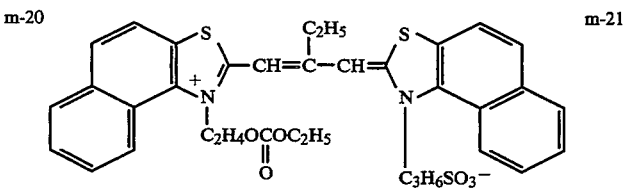
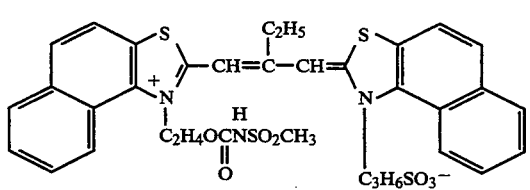
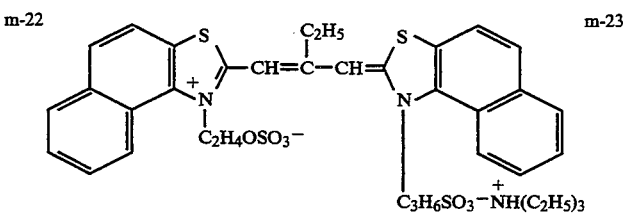

-continued
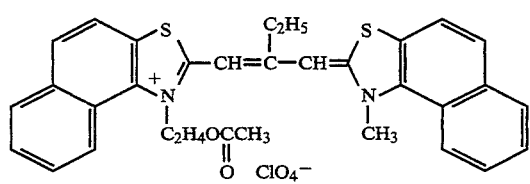 m-24
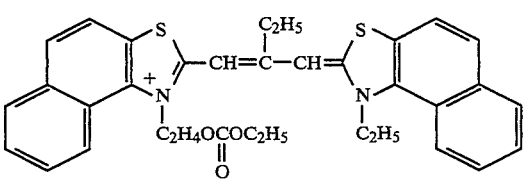 m-25
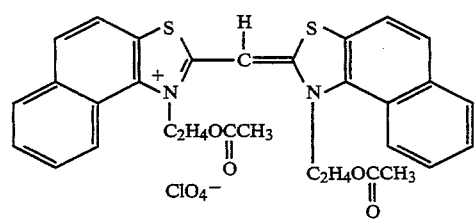 m-26
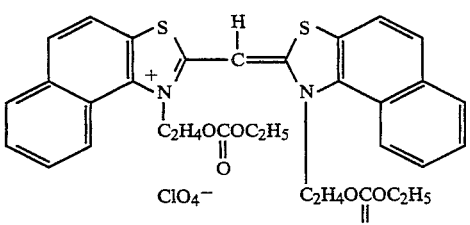 m-27
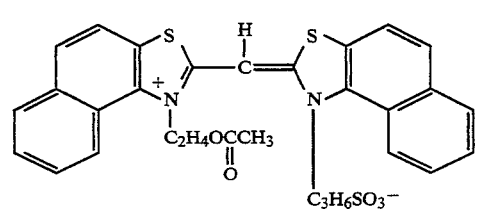 m-28
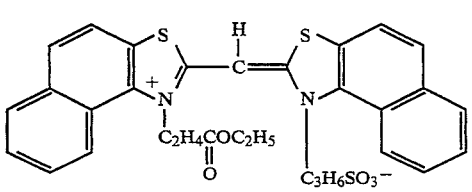 m-29
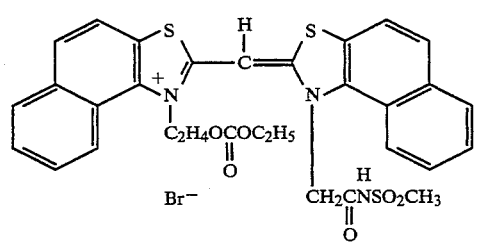 m-30
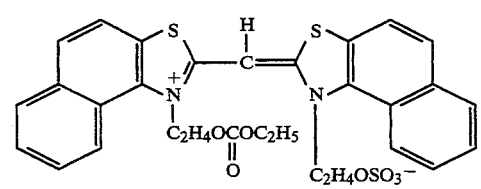 m-31
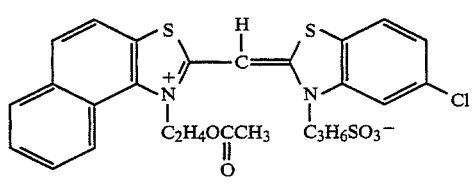 m-32
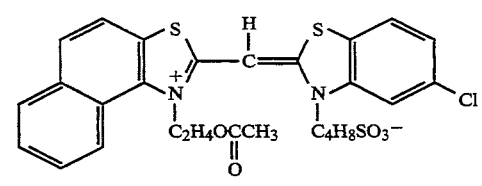 m-33
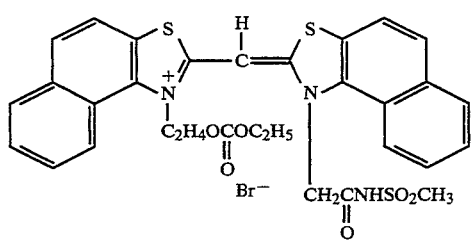 m-34
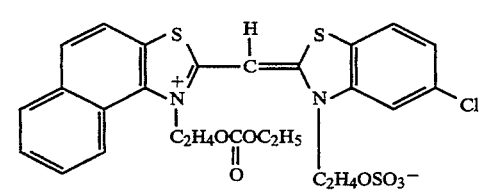 m-35
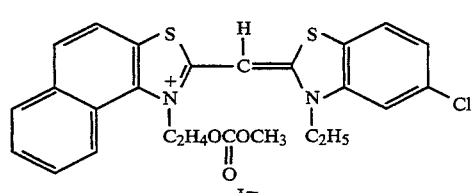 m-36

-continued
m-37
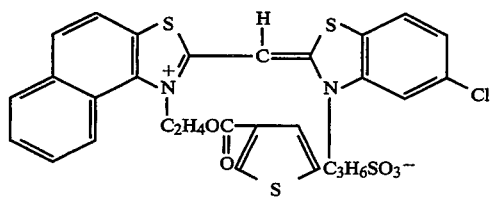
m-38
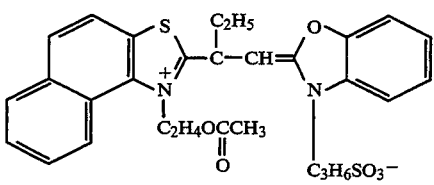
m-39
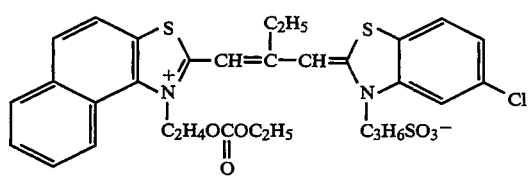
m-40
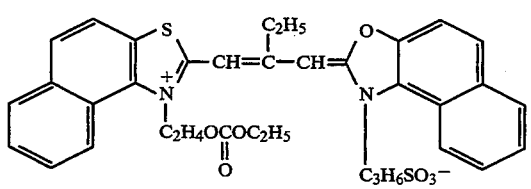
m-41
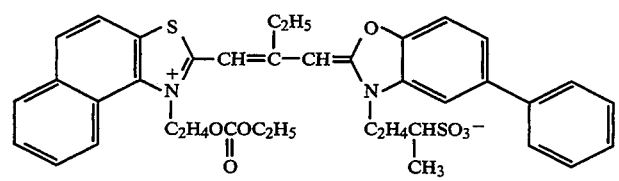
m-42
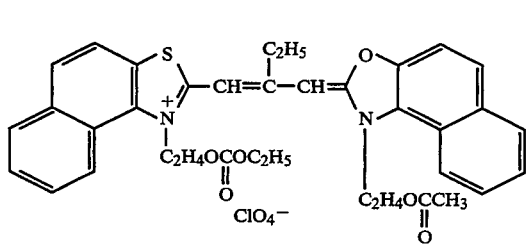
m-43
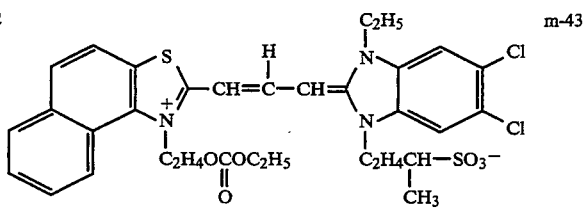
m-44
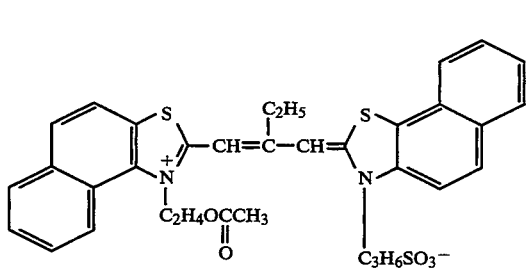
m-45
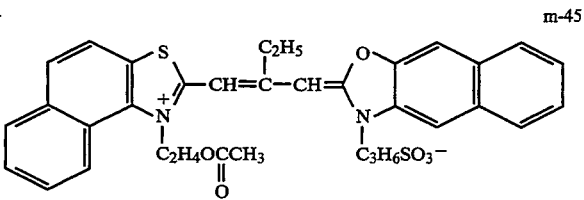
m-46
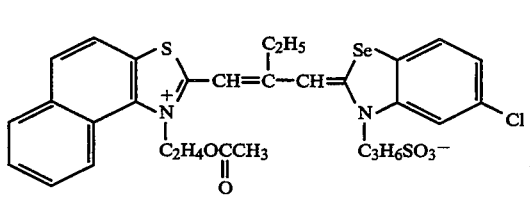
m-47
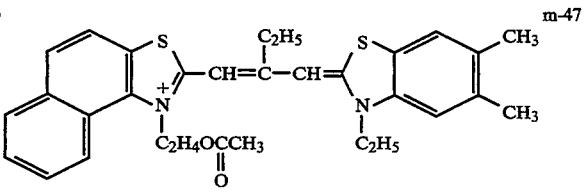
m-48
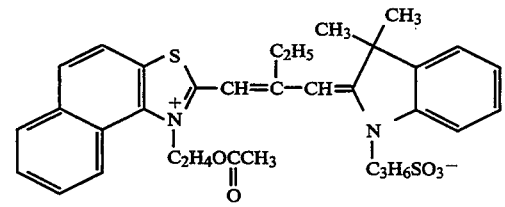
m-49
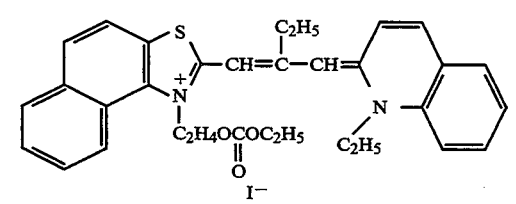

-continued
m-50 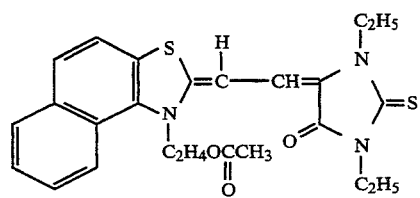
m-51 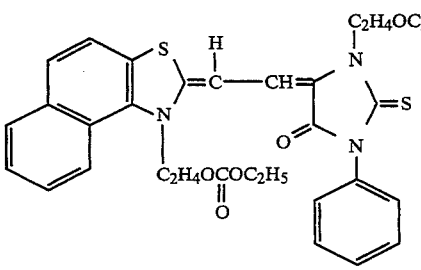
m-52 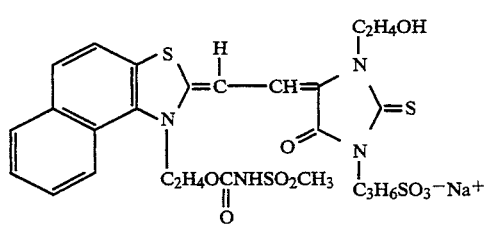
m-53 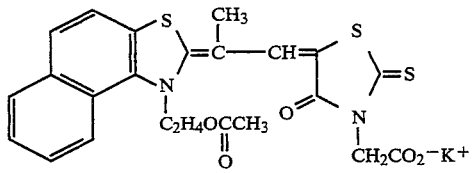
m-54 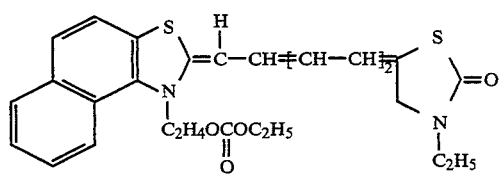
m-55 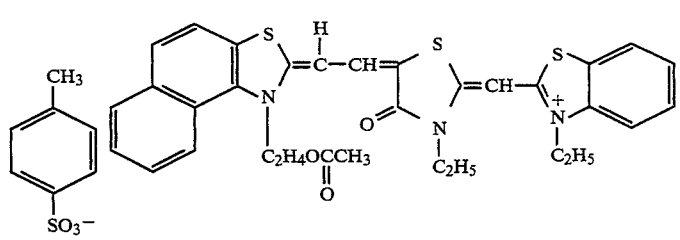
m-57 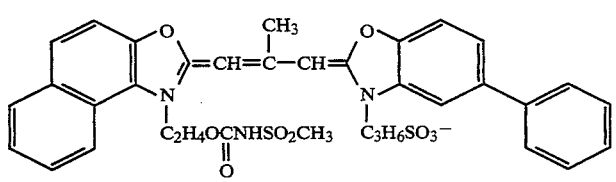
m-58 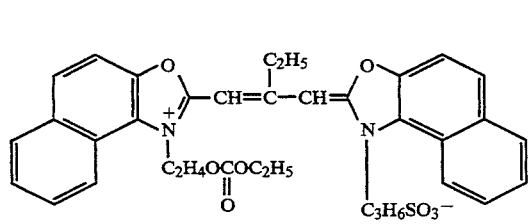
m-59 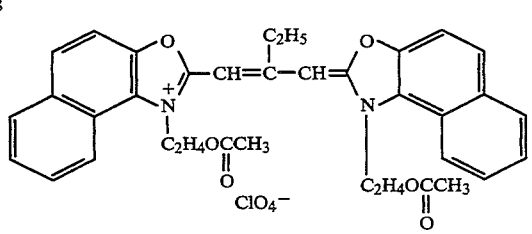
m-60 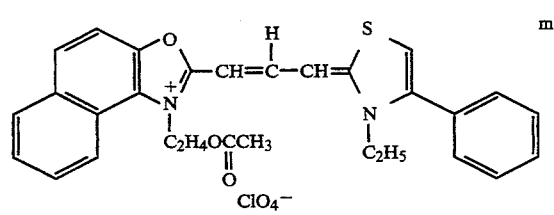
m-61 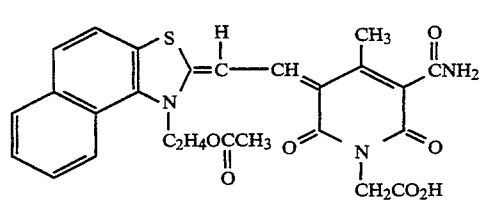

m-62 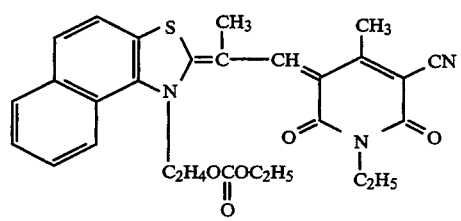
m-63 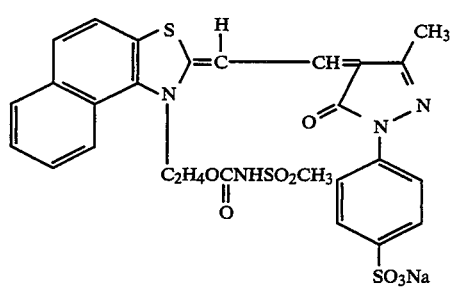
m-64 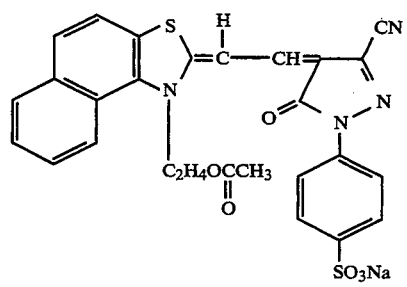
m-65 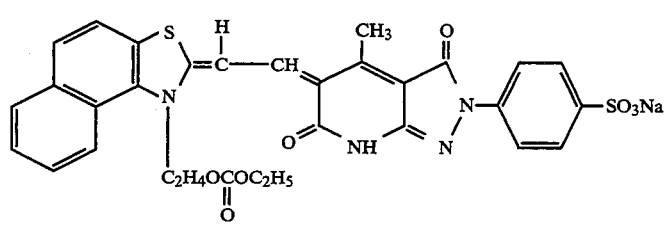
m-66 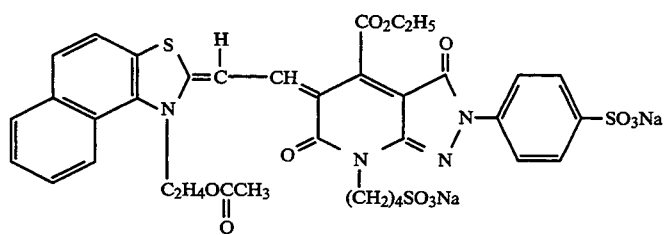
m-67 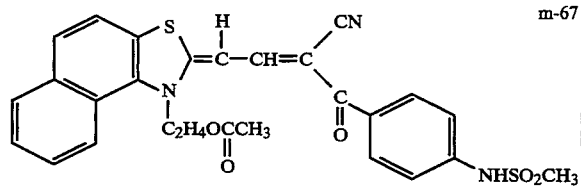
m-68 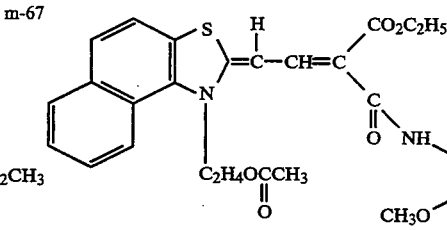
m-69 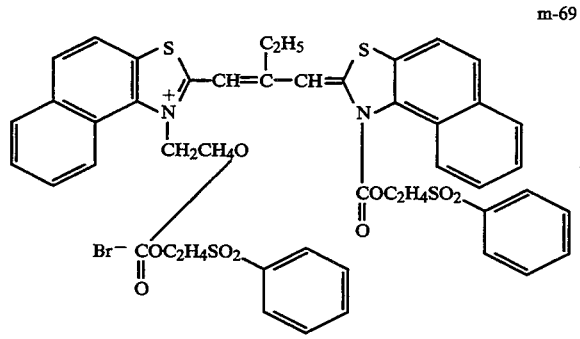
m-70 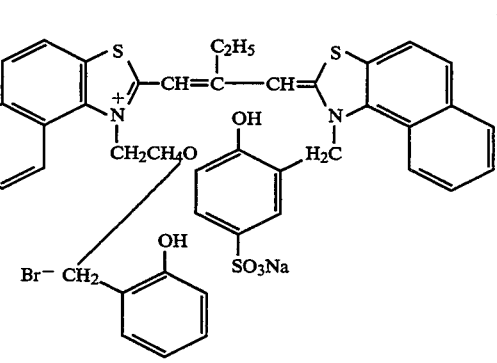

-continued

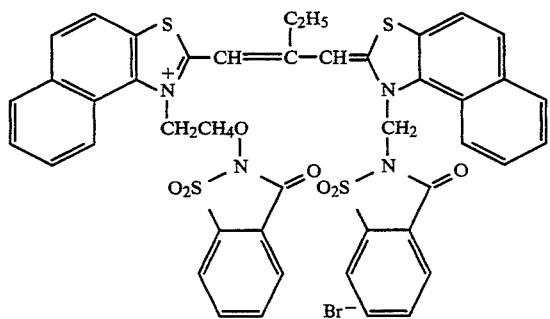
m-71

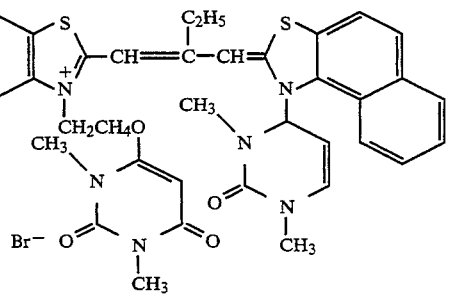
m-72

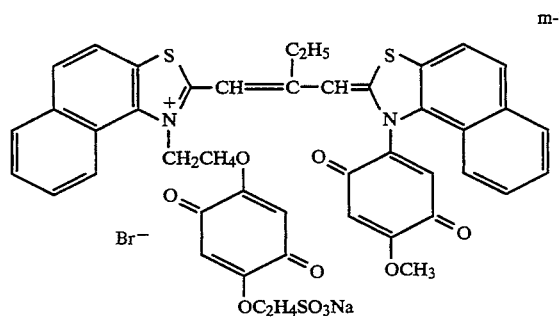
m-73

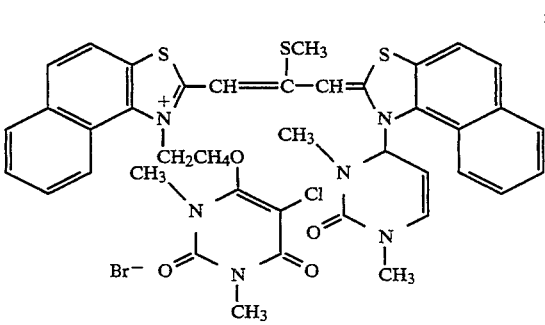
m-74

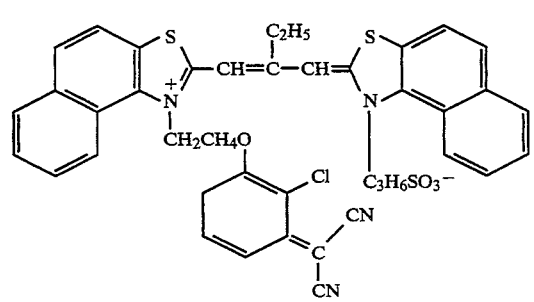
m-75

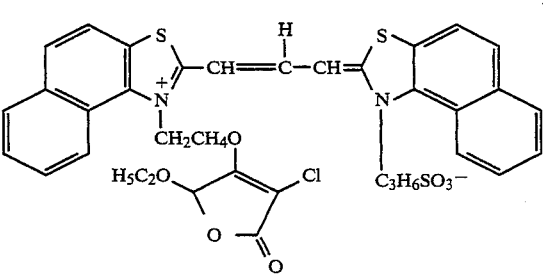
m-76

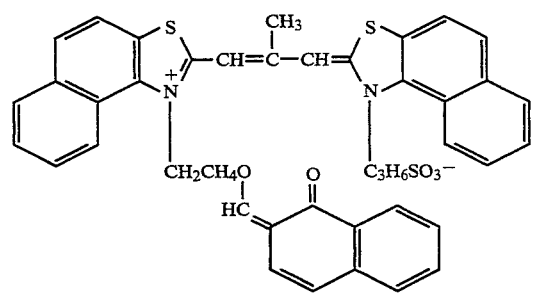
m-77

In the above examples, compounds of the formula (I) include all examples, compounds of the formula (II) include examples of M-8 to M-65 and m-1 to m-77, and compounds of the formula (III) include examples of M-8 to M-13, M-20 to M-23, M-26 to M-30, M-32 to M-38, M-41 to M-65 and m-1 to m-77.

The methine compound of the formula (III) is basically prepared by the process comprising a step of causing a cyclic alkylene carbonate compound of the following formula (1) to react in the presence of Lewis acid with a nitrogen-containing heterocyclic compound having a fused ring of the following formula (3) to give a N-substituted nitrogen-containing heterocyclic compound having a fused ring of the following formula (2), a step of converting the N-substituted nitrogen-containing heterocyclic compound into its quaternary salt and a step of causing the quaternary salt to react with a compound to form a methine or polymethine group which may have a substituent represented by Q according to a conventional method. The method is also employed for the preparation of the compounds of the formula (I) or (II)

The methine compound of the formula (III) is, for example, prepared by the following manner.

The above cyclic alkylene carbonate compound is represented by the formula (1)

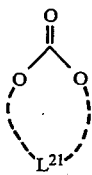

(1)

In the above formula (1), $L^{21}$ represents the meanings defined in the formula (III), i.e., represents an ethylene or propylene group which may have a substituent.

The Lewis acid is defined as a material (i.e., electron acceptor) which has a vacant orbital capable of accepting at least one electron pair. The definition of Lewis acid is, for example, described in "Advanced Organic Chemistry" (Reaction, Mechanisms and structure; J. March, the third edition, pages 227–234)

The Lewis acid employable for the invention may be one of any known Lewis acids. Examples of the Lewis acid generally include semi-metal compounds, metal compounds and complexes thereof. From the viewpoints of a high yield of the N-substituted nitrogen-containing heterocyclic compound and easy after-treatment of the resultant reaction mixture, the Lewis acid is preferred to be $BF_3 \cdot Et_2O$, $BF_3 \cdot Me_2O$, $TiCl_4$, $AlCl_3$, $FeCl_3$, $SnCl_4$, $ZnCl_2$ or $BF_3 \cdot THF$, and particularly preferred to be boron trifluoride etherate such as $BF_3 \cdot Et_2O$, $BF_3 \cdot Me_2O$ or $BF_3 \cdot THF$.

The above nitrogen-containing heterocyclic compound with which a cyclic alkylene carbonate compound is caused to react in the presence of Lewis acid has the following formula (3).

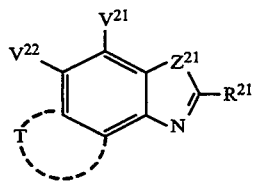

(3)

In the above formula (3), $R^{21}$ represents an alkyl group, an aryl group or a heterocyclic group, and each of $V^{21}$, $V^{22}$ $Z^{21}$ and T represents the meanings defined in the formula (III).

$R^{21}$ generally represents an alkyl group having 1 to 18 carbon atoms which may have a substituent, an aryl group having carbon atoms of not more than 18 which may have a substituent or a heterocyclic group, having carbon atoms of not more than 18 which may have a substituent.

Examples of the alkyl group include methyl, ethyl, propyl, isopropyl, allyl, butyl, isobutyl, hexyl, octyl, dodecyl and octadecyl. Examples of the substituent of the alkyl group include carboxyl, sulfo and halogen.

Examples of the aryl group include phenyl, 2-naphthyl and 1-naphthyl. Examples of the substituent of the aryl group include carboxyl, sulfo,cyano, nitro, hydroxy, halogen, alkyl having carbon atoms of 1 to 8 (e.g., methyl or ethyl), alkoxy having carbon atoms of 1 to 8 (e.g., methoxy or ethoxy), aryloxy having carbon atoms of not more than 15 (e.g., phenoxy), acyloxy having carbon atoms of 1 to 8 (e.g., acetyloxy), acyl having carbon atoms of 1 to 8, sulfamoyl having carbon atoms of 1 to 8, carbamoyl having carbon atoms of 1 to 8 and aryl having carbon atoms of not more than 15 (e.g., phenyl).

Examples of the heterocyclic group include 2-pyridyl, 2-thiazolyl, 2-furyl and 2-thiophenyl.

The group represented by $R^{21}$ preferably is a unsubstituted alkyl group having carbon atoms of not more than 18 (e.g., methyl, ethyl, propyl or butyl) or a unsubstituted aryl group having carbon atoms of not more than 18 (e.g., phenyl or 1-naphthyl), and more preferably is methyl, ethyl or phenyl.

The above nitrogen-containing heterocyclic compound has a fused ring that a 5- or 6-membered nitrogen-containing heterocyclic compound such as pyridine, imidazole, thiazole, oxazole, selenazole, indole or pyrimidine is fused with an aromatic ring such as benzene or naphthalene, an aliphatic ring or a heterocyclic ring.

The known N-substituted nitrogen-containing heterocyclic compound having no fused ring is also prepared by causing the cyclic alkylene carbonate compound to react in the presence of Lewis acid with a nitrogen-containing heterocyclic compound having no fused ring. The obtained N-substituted nitrogen-containing heterocyclic compound undergoes salt-exchange to obtain a quaternary salt of a N-hydroxyalkyl-substituted heterocyclic compound. Examples of the quaternary salt of the N-hydroxyalkyl-substituted heterocyclic compound are as follows:

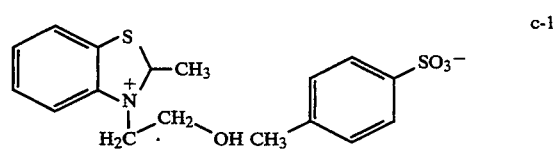

c-1

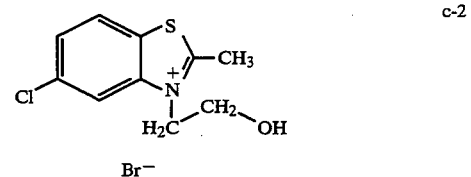

c-2

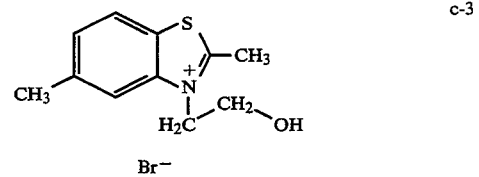

c-3

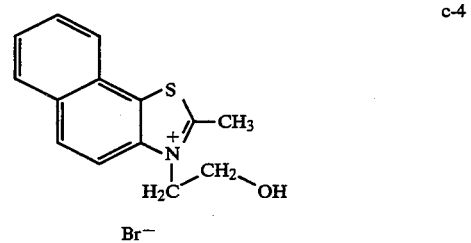

c-4

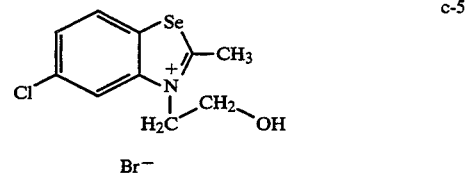

c-5

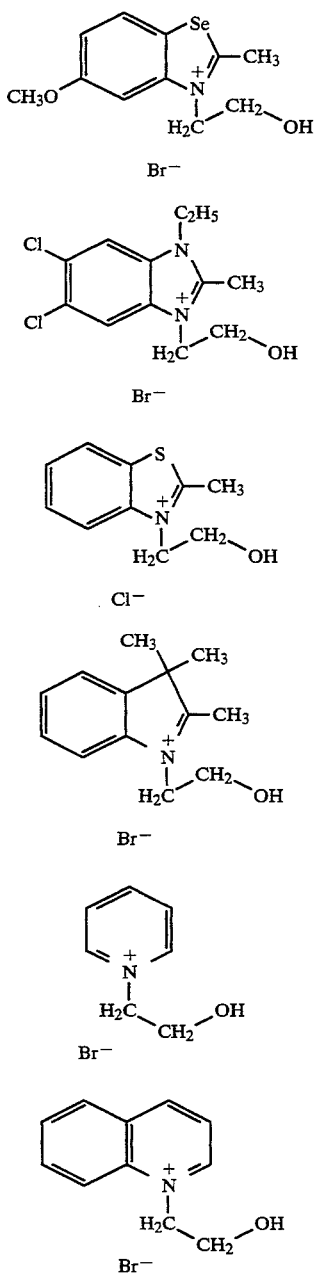

[Synthesis Example 1]

Synthesis of 3-(2-hydroxyethyl)-2-methylbenzothiazolium paratoluenesulfonate (aforementioned compound C-1)

In a round flask equipped with a stirrer and a reflux condenser were placed 14.9 g (0.10 mol) of 2-methylbenzothiazole, 11.4 g (0.13 mol) of ethylene carbonate and 14 ml (0.11 mol) of boron trifluoride ethyl etherate. The flask was immersed in an oil bath and heated at 190° C. for 4.5 hours with stirring of the mixture.

After the reaction was complete, the reaction mixture was cooled to room temperature, and 280 ml of ethyl acetate was added to the flask. When the mixture in the flask was stirred, yellow crystals precipitated. The crystals were collected by filtration, and the collected crystals were stirred in isopropanol containing 17.2 g (0.10 mole) of p-toluenesulfonate for 1 hour, and then the crystals were collected by filtration. The crystals were dried at 50° C. for 1 hour to obtain 29.3 g of pale yellow crystals (yield: 80%).

[Synthesis Example 2]

Synthesis of 5-chloro-3-(2-hydroxyethyl)-2-methylbenzothiazolium bromide (aforementioned compound C-2)

In a round flask equipped with a stirrer and a reflux condenser were placed 18.4 g (0.10 mol) of 5-chloro-2-methylbenzothiazole, 11.4 g (0.13 mol) of ethylene carbonate and 14 ml (0.11 mol) of boron trifluoride ethyl etherate. The flask was immersed in an oil bath and heated at 190° C. for 4.5 hours with stirring.

After the reaction was complete, the reaction mixture was cooled to room temperature, and 280 ml of ethyl acetate was added to the flask. When the mixture in the flask was stirred, yellow crystals precipitated. The crystals were collected by filtration, and the collected crystals were stirred in isopropanol containing 30 g (0.10 mole) of hydrobromic acid for 1 hour, and then the crystals were collected by filtration. The crystals were dried at 50° C. for 1 hour to obtain 24.3 g of pale yellow crystals (yield: 79%).

[Synthesis Example 3]

Synthesis of 3-(2-hydroxyethyl)-2,5-dimethylbenzothiazolium bromide (aforementioned compound C-3)

In a round flask equipped with a stirrer and a reflux condenser were placed 18.4 g (0.10 mol) of 2,5-dimethylbenzothiazole, 11.4 g (0.13 mol) of ethylene carbonate and 14 ml (0.11 mol) of boron trifluoride ethyl etherate. The flask was immersed in an oil bath and heated at 190° C. for 2.5 hours with stirring.

After the reaction was complete, the reaction mixture was cooled to room temperature, and 280 ml of ethyl acetate was added to the flask. When the mixture in the flask was stirred, yellow crystals precipitated. The crystal was collected by filtration, and the collected crystals were stirred in isopropanol containing 30 g (0.10 mole) of hydrobromic acid for 1 hour, and then the crystals were collected by filtration. The crystals were dried at 50° C. for 1 hour to obtain 23.0 g of pale yellow crystals (yield: 80%).

[Synthesis Example 4]

Synthesis of 3-(2-hydroxyethyl)-2,5-methylnaphto[2,1-d]thiazolium bromide (aforementioned compound C-4)

In a round flask equipped with a stirrer and a reflux condenser were placed 19.9 g (0.10 mol) of 2-methylnaphto[2,1-d]thiazole, 11.4 g (0.13 mol) of ethylene carbonate and 14 ml (0.11 mol) of boron trifluoride ethyl etherate. The flask was immersed in an oil bath and heated at 190° C. for 2.5 hours with stirring.

After the reaction was complete, the reaction mixture was cooled to room temperature, and 280 ml of ethyl acetate was added to the flask. When the mixture in the flask was stirred, yellow crystals precipitated. The crystals were collected by filtration, and the collected crystals were stirred in isopropanol containing 30 g (0.10 mole) of hydrobromic acid for 1 hour, and then the crystals were collected by filtration. The crystals were dried at 50° C. for 1 hour to obtain 13.2 g of pale yellow crystals (yield: 41.1%).

The N-substituted nitrogen-containing heterocyclic compound having a fused ring of the following formula (2):

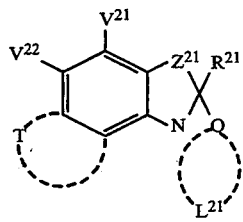
(2)

can be also prepared by causing the cyclic alkylene carbonate compound to react in the presence of Lewis acid with the nitrogen-containing heterocyclic compound having a fused ring of the above formula (3).

In the formula (2), $R^{21}$ represents the meanings defined in the formula (3), and each of $V^{21}$, $V^{22}$, $Z^{21}$, $L^{21}$ and T represents the meanings defined in the formula (III). Examples of the N-substituted heterocyclic compound having a fused ring of the formula (2) are as follows:

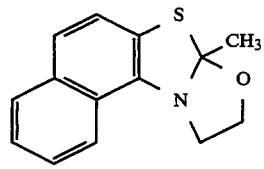 d-1

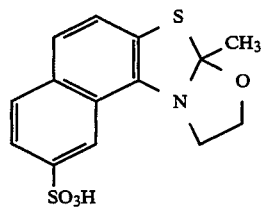 d-2

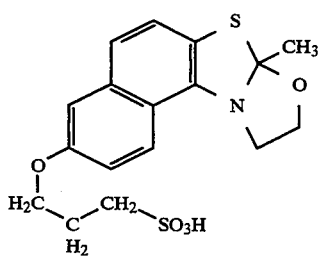 d-3

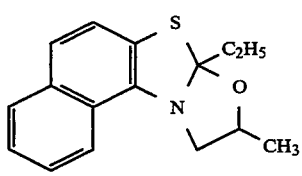 d-4

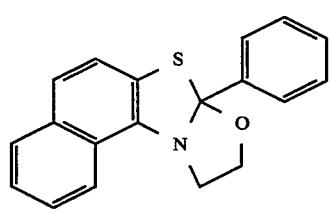 d-5

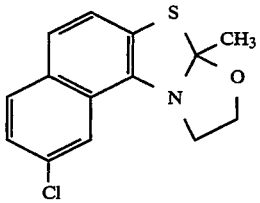 d-6

[Synthesis Example 5]

Synthesis of oxazolino[2,3-b]-2-methylnaphto[1,2-d]thiazole (aforementioned compound d-1)

In a round flask equipped with a stirrer and a reflux condenser were placed 19.9 g (0.10 mol) of 2-methylnaphto[1,2-d]thiazole, 11.4 g (0.13 mol) of ethylene carbonate and 14 ml (0.11 mol) of boron trifluoride ethyl etherate. The flask was immersed in an oil bath and heated at 170° C. for 2 hours with stirring.

After the reaction was complete, the reaction mixture was cooled to room temperature, and 400 ml of n-hexane was added to the flask. When the mixture in the flask was stirred, white crystals precipitated. The crystals were collected by filtration, and were dried at 50° C. for 1 hour to obtain 18.7 g of white crystals (yield: 60%).

It was confirmed that the compound of the above white crystals was the same as the subject compound by NMR and FAB mass spectrum as set forth below.

[NMR]
δ: 2.00 (s, 3H)
3.45 (m, 1H)
3.90 (m, 2H)
4.25 (m, 1H)
7.35 (m, 4H)
7.75 (m, 2H)

[FAB mass spectrum]
m/e: 243

The N-substituted nitrogen-containing heterocyclic compound having a fused ring of the formula (2) can be converted into the quaternary salt of the N-substituted nitrogen-containing heterocyclic compound of the following formula (4):

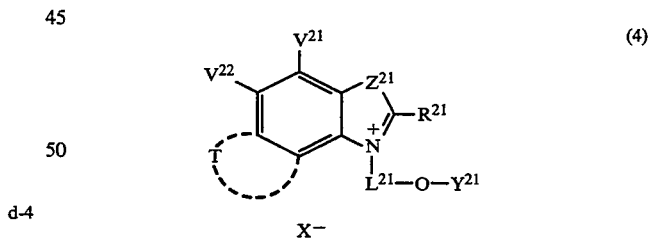
(4)

In the formula (4), $R^{21}$ has the meanings defined in the formula (2), and each of $V^{21}$, $V^{22}$, $Z^{21}$, $L^{21}$, Y and T has the meanings defined in the formula (III). $X^-$ represents a counter anion of a quaternary ammonium ion. The anion serves to supply negative electric charge necessary for neutralizing the electric charge of the quaternary ammonium ion and is not always monovalent.

Examples of the anion include halogen ions such as $F^-$, $Cl^-$, $Br^-$ and $I^-$; $SO_4^{2-}$, $HSO_4^-$, and alkyl sulfuric acid ions such as $CH_3OSO_3^-$; sulfonic acid ions such as paratoluenesulfonic acid ion, methanesulfonic acid ion and trifluoromethanesulfonic acid ion; caboxylic acid ions such as acetic acid ion, trifluoroacetic acid ion and oxalic acid ion; and $PF_6^-$, $BF_4^-$, $ClO_4^-$, $IO_4^-$, $PO_4^{3-}$, $NO_3^-$ and phenolate ions such as picric acid ion.

Examples of the quaternary salt of the N-substituted heterocyclic compound having a fused ring of the formula (4) are as follows:

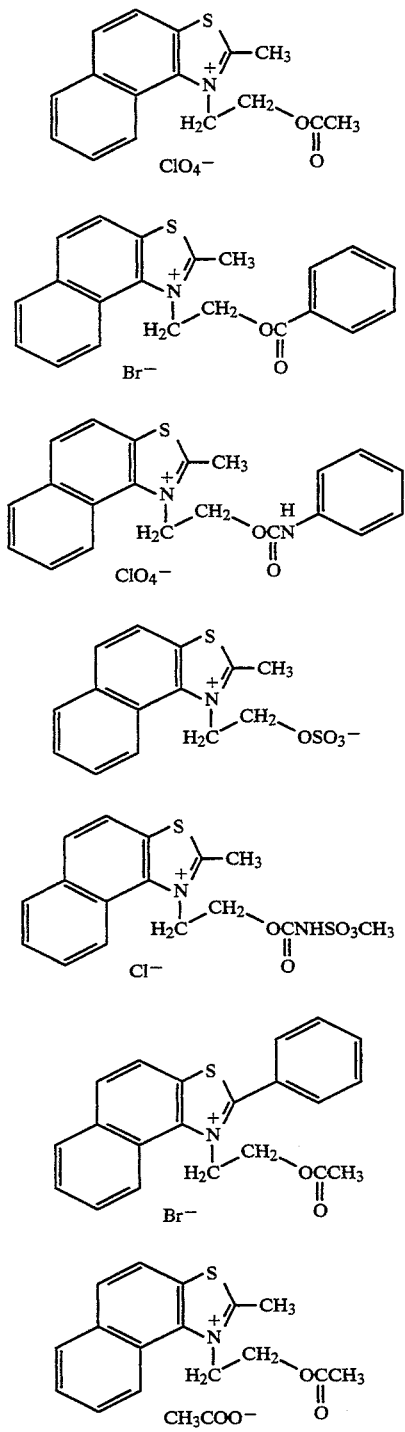

[Synthesis Example 6]

Synthesis of 3-(2-acetoxyethyl)-2-methylnaphto[1,2-d]thiazoliume perchlorate (aforementioned compound e-1)

In a round flask equipped with a stirrer and a reflux condenser were placed 19.9 g (0.10 mol) of 2-methylnaphto[1,2-d]thiazole, 11.4 g (0.13 mol) of ethylene carbonate and 14 ml (0.11 mol) of boron trifluoride ethyl etherate. The flask was immersed in an oil bath and heated at 170° C. for 2 hours with stirring.

After the reaction was complete, the reaction mixture was cooled to room temperature, and 15 ml of acetic anhydride was added to the flask. After 1 hour, to the flask was further added 8.23 g (0.08 mole) of ammonium perchlorate. Further after 1 hour, to the flask was further added 300 ml of ethyl acetate. When the mixture in the flask was stirred, white crystals precipitated. The crystals were collected by filtration, and were dried at 50° C. for 1 hour to obtain 18.7 g of white crystals (yield: 60%).

It was confirmed that the compound of the above white crystals was the same as the subject compound by NMR and FAB mass spectrum as set forth below.

[NMR]
δ: 1.90 (s, 3H)
3.33 (s, 3H)
4.70 (t, 2H)
5.55 (t, 2H)
7.94 (m, 2H)
8.40 (m, 3H)
8.80 (d, 1H)

[FAB mass spectrum]
m/e: 286

[Synthesis Example 7]

Synthesis of 2-methylnaphto[1,2-d]thiazoliume 3-ethyloxysulfonate (aforementioned compound e-4)

In a round flask equipped with a stirrer and a reflux condenser were placed 19.9 g (0.10 mol) of 2-methylnaphto[1,2-d]thiazole, 11.4 g (0.13 mol) of ethylene carbonate and 14 ml (0.11 mol) of boron trifluoride ethyl etherate. The flask was immersed in an oil bath and heated at 170° C. for 2 hours with stirring.

After the reaction was complete, the reaction mixture was cooled to room temperature, and 13.0 g of sulfamic acid was added to the flask. After 1 hour, to the flask was further added 300 ml of ethyl acetate. When the mixture in the flask was stirred, white crystals were precipitated. The crystals were collected by filtration, and were dried at 50° C. for 1 hour to obtain 18.4 g of white crystals (yield: 60% ).

It was confirmed that the compound of the above white crystals was the same as the subject compound by NMR and FAB mass spectrum as set forth below.

[NMR]
δ: 2.25 (s, 3H)
4.45 (t, 2H)
5.40 (t, 2H)
7.90 (m, 2H)
8.35 (m, 3H)
8.73 (d, 1H)

[FAB mass spectrum]
m/e: 323

Subsequently, the process for the preparation of the N-substituted nitrogen-containing heterocyclic compound having a fused ring using the cyclic alkylene carbonate and Lewis acid, is explained in more detail below. The N-substituted nitrogen-containing heterocyclic compound has a fused ring of the above formula (2) or it may be a quaternary salt of the N-substituted nitrogen-containing heterocyclic compound of the following formula (4).

The process for preparing N-substituted nitrogen-containing heterocyclic compound is conducted by heating the mixture of the nitrogen-containing heterocyclic compound of the formula (3), the cyclic alkylene carbonate of the formula (2) and Lewis acid at a desired temperature. Operations for conducting the process are not restricted. Preferred procedures comprise the steps of heating the mixture of the nitrogen-containing heterocyclic compound and the cyclic alkylene carbonate to the desired temperature (reaction temperature), and adding gradually the Lewis acid to the mixture under stirring.

In the process, the ratio between the nitrogen-containing heterocyclic compound and the cyclic alkylene carbonate {heterocyclic compound: carbonate} preferably is 1:1 to 1:5 by mole, and more preferably 1:1.5 to 1:2. The ratio between the nitrogen-containing heterocyclic compound and the Lewis acid {heterocyclic compound: Lewis acid} preferably is 1:1 to 1:3 by mole, and more preferably 1:1 to 1:1.5.

In the process, the temperature (reaction temperature) for heating the above mixture is preferably in the range of 80° C. to 250° C., and more preferably in the range of 120° C. to 200° C. In the case that the reaction temperature is lower than the lower limit of the above range, the yield of the resultant N-substituted nitrogen-containing heterocyclic compound decreases. In the case that the reaction temperature is higher than the upper limit of the above range, the yield of the resultant N-substituted nitrogen-containing heterocyclic compound hardly increases and the compound and the materials are apt to decompose. Therefore, such heating brings about loss of heat energy. Further, the reaction generally reaches the about maximum in the range of 10 minutes to 3 hours, although it differs depending on the materials used in the reaction or the reaction temperature. Hence, the reaction time generally is not shorter than 10 minutes, preferably in the range of 10 minutes to 6 hours, and more preferably in the range of 10 minutes to 3 hours.

It may be not required to use inert solvents in the reaction. If necessary, inert solvents (e.g., sulfolane, anisole or 1,1,2-trichloroethane) which have no participation in the reaction may be added into the reaction mixture.

In the reaction, it may increase the yield to add into the reaction mixture a basic substance (e.g., sodium acetate or 2,6-litidine) which is hardly converted into its quaternary salt.

Thus, the cyclic alkylene carbonate adduct of the nitrogen-containing heterocyclic compound or the cyclic alkylene carbonate adduct of the nitrogen-containing heterocyclic compound of the formula (2) (ring closure product) is obtained. The quaternary salt of the N-substituted nitrogen-containing heterocyclic compound is prepared by adding an acid to the cyclic alkylene carbonate-added nitrogen-containing heterocyclic compound according to a known method.

Otherwise, the quaternary salt of the cyclic alkylene carbonate adduct of the nitrogen-containing heterocyclic compound of the formula (2) (ring closure product), may be obtained in such a manner that the ring closure product is subjected to the following procedures whether after isolating and purifying it or as it is the above reaction mixture containing the ring closure product.

For example, an appropriate reagent (e.g., the following acid or anhydride) for converting into a quaternary salt (quaternization) is portionwise dropped into the mixture to obtain the the quaternary salt. Examples of the reagent include substituted or unsubstituted halogenated alkanes, substituted or unsubstituted halogenated arenes, carboxylicanhydrides, sulfonic anhydrides, isocyanate compounds, halides of acids such as a sulfonic acid, a carboxylic acid, a carbonic acid and a carbamic acid, and sulfamic acid. Further, the obtained quaternary salt may be converted into other quaternary salt having a different salt from the salt, if desired.

In the above process, the ratio between the nitrogen-containing heterocyclic compound and the reagent for converting into a quaternary salt {heterocyclic compound: reagent} preferably is 1:1 to 1:5 by mole, and more preferably 1:1.5 to 1:2.

In the process, the temperature (reaction temperature) for quaternization is preferably in the range of room temperature to 200° C., and more preferably in the range of 30° C. to 100° C. In the case that the reaction temperature is lower than the lower limit of the above range, the yield of the quaternary salt decreases. In the case that the reaction temperature is higher than the upper limit of the above range, the yield of the resultant quaternary salt hardly increases and the compound and the materials are apt to decompose. Therefore, such heating brings about loss of heat energy. Further, the reaction generally reaches the about maximum in the range of 10 minutes to 3 hours, although it differs depending on the materials used in the reaction or the reaction temperature. Hence, the reaction time generally is not shorter than 10 minutes, preferably in the range of 10 minutes to 6 hours, and more preferably in the range of 10 minutes to 3 hours.

It may be not required to use inert solvents in the reaction. If necessary, inert solvents (e.g., sulfolane, anisole or 1,1,2-trichloroethane) which have no participation in the reaction may be added into the reaction mixture.

After the reaction is complete, the quaternary salt of the N-substituted nitrogen-containing heterocyclic compound is separated from the obtained reaction mixture according to a known method and it is further purified, if necessary. The methods to purify the quaternary salt may comprise the steps of pouring the reaction mixture into a poor solvent such as ethyl acetate to allow the quaternary salt to crystallize, separating it by filtration, and recrystallizing it from alcohol solvent such as methanol, ethanol or propanol. However, the nitrogen-containing heterocyclic compound of the formula (2) (ring closure product) does not show such insolubility in organic solvents that the quaternary salt shows, so that it is necessary to carefully select solvent for separation and purification of the quaternary salt. For example, n-hexane can be used.

According to the above process, the yield of the quaternary salt including the salt of the formula (4) or the nitrogen-containing heterocyclic compound including the compound of the formula (2) is not less than 40 weight % (generally not less than 50 weight %) based on the amount of the above nitrogen-containing heterocyclic compound.

The compound of the formula (III) can be synthesized by causing the quaternary salt of the formula (4) corresponding to a structure of the heterocyclic ring other than "$Q^{21}$" to react with a material corresponding to the "$Q^{21}$", according to a structure of desired compound.

Materials used as above can be generally selected by referring to the following: "Heterocyclic Compounds-Cyanine dyes and Related Compounds; John Wiley & Sons; New York, London;, (1964)", and "Heterocyclic Compounds-Special Topics in Hetrocyclic Chemistry; by D. M. Sturmer; Chapter 8, Paragraph 4, pp. 484–515; John Wiley & Sons; New York, London; (1977)".

In the above synthesis, the mixture of these materials (compounds) is generally caused to react at a temperature of 0° to 200° C., preferably at a temperature of 0° to 180° C., and more preferably a temperature of 15° to 200° C. As examples of solvents used in the synthesis, there can be mentioned various solvents including polar solvents such as water, alcohols, N,N-dimethylformamide (DMF) and dimethylsulfoxide (DMSO) and nonpolar solvents such as benzene and hexane. Preferred examples of the solvents include polar solvents such as DMF and DMSO, alocohols such as methanol and ethanol, nitriles such as acetonitrile and benzonitrile, esters such as ethyl acetate and ethers such as tetrahydrofuran and 1,2-dimethoxyethane. Particularly preferred are polar solvents, alcohols and nitriles. The solvents are may be employed singly or in combination.

In the reaction (synthesis), an acid and a base may be employed. Examples of the acid include inorganic acids and organic acids. Preferred are organic acids. Particularly, carboxylic acids such as acetic acid and propionic acid and phenols such as phenol and m-cresol are preferred. Examples of the base include inorganic bases and organic bases. Preferred are organic bases. Particularly, tertiary amines such as triethylamines and aromatic or heterocyclic amines such as pyridine are preferred.

The silver halide photographic light-sensitive material of the invention contains the methine compound of the above formula (I) or (II) in at least one layer (preferably in a silver halide emulsion layer) of layers constituting the light-sensitive material.

For incorporation of the methine compound into the silver halide emulsion (also referred to as "photographic emulsion" hereinafter), the methine compound may be directly dispersed in the emulsion. Otherwise, a solution of the methine compound in a solvent such as water, methanol, ethanol, propanol, methyl cellosolve or 2,2,3,3-tetrafluoropropanol may be added to the emulsion. In this case, the solvents may be used alone or in a mixture of plural kinds. Further, an aqueous solution of the methine compound obtained in the presence of an acid or a base may be added to the emulsion as described in Japanese Patent Publications No. 44(1969)-23389, No. 44(1969)-27555 and No. 57(1982)-22089, or an aqueous solution or a colloidal dispersion of the methine compound obtained in the presence of a surface active agent may be added to the emulsion as described in U.S. Pat. Nos. 3,822,135, and No. 4,006,025. Furthermore, it is also possible to dissolve the methine compound in a solvent which is substantially not miscible with water such as phenoxyethanol, then to disperse the solution in water or a hydrophilic colloid, and to add the resulting dispersion to the emulsion. Moreover, it is also possible to directly disperse the methine compound in a hydrophilic colloid and to add the resulting dispersion to the emulsion as described in Japanese Patent Provisional Publications No. 53(1978)-102733 and No. 58(1983)-105141.

The sensitizing or desensitizing dye and other dye used in the invention may be dissolved in the emulsion using ultrasonic vibration described in U.S. Pat. No. 3,485,634. For adding those dyes to the emulsion, there can be used other dissolving or dispersing methods which are described in U.S. Pat. Nos. 3,482,981, No. 3,585,195, No. 3,469,987, No. 3,425,835 and No. 3,342,605, U.K. Patents No. 1,271,329, No. 1,038,029 and No. 1,121,174, and U.S. Pat. Nos. 3,660,101, and No. 3,658,546.

The above-mentioned dyes may be used in any of stages in the process for preparing the photographic emulsion, or may be used in any of stages after the preparation of the emulsion but before the coating stage. Examples of the stages in the former case include a stage of silver halide grain formation, a stage of physical ripening and a stage of chemical ripening. For example, the dyes may be added in the stage of silver halide grain formation as described in Japanese Patent Provisional Publication No. 55(1980)-26589.

The sensitizing or desensitizing dye employable in the invention is contained in the silver halide emulsion in an amount of $5\times10^{-9}$ mol to $2\times10^{-2}$ mol, preferably $5\times10^{-6}$ mol to $2\times10^{-3}$ mol, and more preferably $1\times10^{-5}$ mol to $1\times10^{-3}$ mol, based on 1 mol of the silver halide.

The silver halide to be contained in the silver halide photographic emulsion used in the invention may be any of silver bromide, silver iodobromide, silver iodochlorobromide, silver chlorobromide and silver chloride. The silver halide grains may have any crystalline phase.

The silver halide emulsion may be an emulsion of tabular grains. The tabular grains preferably have a grain thickness of not more than 0.5 μm, preferably not more than 0.3 μm. The grain diameter preferably is not less than 0.6 μm. In the tabular emulsions, the projected area of the tabular grains having a aspect ratio of not less than 5 is not less than 50% of the total projected area of the grains. The silver halide emulsion may also be a mono-dispersed emulsion in which the sizes of not less than 95% by number of the grains are within a range of ±40% of the mean grain size.

The individual silver halide grains may have a homogeneous phase or a heterogeneous phase in which the phase varies from the outer surface portion to the inside portion. Further, the silver halide emulsion may be such an emulsion that a latent image is formed mainly on the surface of the grain (e.g., negative type emulsion), or may be such an emulsion that a latent image is formed mainly inside of the grain (e.g., internal latent image type emulsion or pre-fogged direct reverse type emulsion).

The photographic emulsion used in the invention can be prepared in accordance with processes described in, for example, P. Glafkides, "Chimie et Physique Phtographique", Paul Montel, 1967; G. F. Duffin, "Photographic Emulsion Chemistry", Focal Press, 1966; and V. L. Zelikman et al., "Making and Coating Photographic Emulsion", Focal Press, 1964.

That is, any of acid process, neutral process and ammonia process can be used. Reaction of a soluble halogen salt may be carried out in accordance with any of one side mixing process, simultaneous mixing method and a combination of them. Further, a process in which grains are formed in the presence of excess silver ion (so-called "reversal mixing method") is also available. A so-called "controlled double jet method", which is a kind of simultaneous mixing method, can also be used. In this method, a pAg value of the liquid phase in which silver halide is formed is kept at a constant value. In accordance with the controlled double jet method, a silver halide emulsion in which silver halide grain has a regular crystal and the grain size is almost uniform can be prepared.

Two or more kinds of silver halide emulsions having been separately prepared may be used by mixing them.

In order to control growth of the silver halide grains, silver halide solvents such as ammonia, potassium rhodanate, ammonium rhodanate, thioether compounds described for example in U.S. Pat. Nos. 3,271,157, No. 3,574,628, No. 3,704,130, No. 4,297,439 and No. 4,276,374, thionic compounds described for example in Japanese Patent Provisional Publications No. 53(1978)-144319, No. 53(1978)-82408 and No. 55(1980)-77737 and amine compounds described for example in Japanese Patent Provisional Publication No. 54(1979)-100717 can be used during the stage of silver halide grain formation.

The process of forming silver halide grains or physical ripening may be carried out in the presence of a cadmium salt, a zinc salt, a lead salt, a thallium salt, an iridium salt or its complex salt, a rhodium salt or its complex salt, an iron salt or an iron complex salt.

The internal latent image type emulsion employable in the invention includes emulsions containing a different metal as described in U.S. Pat. Nos. 2,592,250, No. 3,206,313, No. 3,447,927, No. 3,761,276 and No. 3,935,014.

In general, the silver halide emulsion is chemically sensitized. For the chemical sensitization, a method described in H. Frieser, "Die Grundklagendor Photographischen Prozesse mit Silber halogenlden", Akademizhe Verlagegegellschaft, 1968, pp. 675-734 can be used.

That is, sulfur sensitization using a compound containing sulfur capable of reacting with active gelatin or silver (e.g., thiosulfates, thioureas, mercapto compounds, rhodanines); reduction sensitization using a reducing agent (e.g., stannous salt, amines, hydrazine derivative, formamidinesulfinic acid, silane compound); and noble metal sensitization using a noble metal compound (e.g., gold complex salt, complex salts of metals belonging to Group VIII of a periodic table such as Pt, Rh, Ir and Pd) can be used singly or in combination.

Concrete examples of the chemical sensitizers include sulfur sensitizers such as allylthiocarbamide, thiourea, sodium thiosulfate and cystine; precious metal sensitizers such as potassium chloroaurate, aurous thiosulfate and potassium chloroparadate; reduction sensitizers such as tin chloride, phenylhydrazine and reductone. Other sensitizers such as a polyoxyethylene compound, a polyoxypropylene compound a compound having a quaternary ammonium group may be used in combination.

Various additives may be added to the photographic emulsion to prevent fogging given during preparation of the light-sensitive material, storage thereof and photographic processing thereof or to stabilize photographic properties of the light-sensitive material. That is, there can be used various additives known as antifogging agents or stabilizers, for example, azoles such as benzothiazolium salts, nitroindazoles, triazoles, benzotriazoles and benzimidazoles (particularly, nitro or halogen substituted substance); heterocyclic mercapto compounds such as mercaptothiazoles, mercaptobenzothiazoles, mercaptobenzimidazoles, mercaptothiadiazoles, mercaptotetrazoles (particularly, 1-phenyl-5-mercaptotetrazole) and mercaptopyrimidines; the above-mentioned heterocyclic mercapto compounds having a water-soluble group such as carboxyl group or sulfone group; thioketo compounds such as oxazolinthion; azaindenes such as tetrazaindenes (particularly, 4-hydroxy substituted (1,3,3a,7)tetrazaindenes); benzenethiosulfonic acids; and benzenesulfinic acids.

The silver halide emulsion may contain a polymer latex made of a homopolymer or a copolymer of alkyl acrylate, alkyl methacrylate, acrylic acid, glycidyl acrylate, etc. to enhance dimensional stability of the photographic material or to improve film physical properties. These compounds are disclosed in U.S. Pat. Nos. 3,411,911, No. 3,411,912, No. 3,142,568, No. 3,325,286, No. 3,547,650 and Japanese Patent Publication No. 45(1970)-5331.

In the case where the silver halide emulsion is used as a lithographic light-sensitive material for printing, polyalkylene oxide compounds may be used to enhance contagious development effect. For example, there can be used compounds described in U.S. Pat. Nos. 2,400,532, No. 3,294,537 and No. 3,294,540, French Patents No. 1,491,805 and No. 1,596,673, Japanese Patent Publication No. 40(1965) -234466, and Japanese Patent Provisional Publications No. 60(1985)-156423, No. 54(1979)-18726 and No. 56(1981)-161933. Preferred examples thereof include condensates of alkylene oxides having 2 to 4 carbon atoms (e.g., ethylene oxide, propylene-1,2-oxide, butylene-1,2-oxide; preferably polyalkylene oxide composed of at least 10 ethylene oxide constituent units) with compounds having at least one active hydrogen atom (e.g., water, aliphatic alcohol, aromatic alcohol, aliphatic acid, organic amine and hexytol derivative) and block copolymers of at least two kinds of polyalkylene oxides. Concrete examples of the polyalkylene oxide compounds include polyalkylene glycol alkyl ethers, polyalkylene glycol aryl ethers, polyalkylene glycol alkylaryl ethers, polyalkylene glycol esters, polyalkylene glycol aliphatic amides, polyalkylene glycol amines, polyalkylene glycol block copolymers and polyalkylene glycol graft polymers. The polyalkylene oxide compound employable herein has a molecular weight of 300 to 15,000, preferably 600 to 8,000. An amount of the polyalkylene oxide compound to be added is in the range of 10 mg to 3 g per 1 mol of the silver halide. The polyalkylene oxide compound may be added in any stages of the process for preparing the emulsion.

The silver halide photographic emulsion may contain color couplers such as a cyan coupler, a magenta coupler and an yellow coupler, and coupler dispersing compounds.

In other words, the silver halide photographic emulsion may contain compounds capable of developing color by oxidative coupling reaction with an aromatic primary amine developing solution (e.g., phenylenediamine derivative, aminophenol derivative). Examples of the magenta couplers include a 5-pyrazolone coupler, a pyrazolobenzimidazole coupler, a cyanoacetylcoumarone coupler and a closed acylacetonitrile coupler. Examples of the yellow couplers include acylacetamide couplers such as benzoylacetanilides and pivaloylacetanilides. Examples of the cyan couplers include a naphthol coupler and a phenol coupler. These couplers are desired to be nondiffusion type having a hydrophobic group which is called "a ballast group". The coupler used in the invention may be either four-equivalent or two-equivalent to the silver ion. Also employable are a colored coupler which shows color compensation effect and a coupler which releases a development inhibitor in accordance with the developing process (so-called DIR coupler).

In addition to the DIR coupler, a non-dye-forming coupling compound which gives a colorless product by the coupling reaction and releases a development inhibitor may also be contained in the photographic emulsion.

The silver halide emulsion may contain as filter dyes water-soluble dyes such as oxonole dye, hemioxonole dye and merocyanine dye for the purpose of anti-irradiation or other various purposes.

Further, a variety of surface active agents may be contained in the silver halide emulsion for various purposes such as assisting of coating, inhibition of static electrification, improvement of slipperiness, emulsification or dispersing, inhibition of adhesion and improvements of photographic properties (e.g., development acceleration, promotion of high contrast, sensitization).

Examples of the surface active agents employable in the invention include nonionic surface active agents such as saponin (steroid type), alkylene oxide derivative (e.g., polyethylene glycol), polyethylene glycol alkyl ethers, glycidol derivative, aliphatic esters of polyols and alkyl esters of saccharides; anionic surface active agents such as alkyl carboxylates, alkyl sulfonates, alkylbenzene sulfonates and alkyl sulfates; and cationic surface active agents such as alkylamine salts, aliphatic or aromatic quaternary ammonium salts and heterocyclic quaternary ammonium salts (e.g., pyridinium, imidazolium). For inhibiting static electrification, a fluorine-containing surface active agent is preferably employed.

In the preparation of the light-sensitive material of the invention, the following discoloration inhibitors conventionally known can be also used. Color image stabilizers may be used in the invention alone or in a mixture of two or more kinds. Examples of the discoloration inhibitors include hydroquinone derivatives, gallic acid derivatives, p-alkoxyphenols, p-oxyphenol derivatives and hisphenols.

The photographic emulsion may contain inorganic or organic hardening agents. For example, chromium salts (e.g., chrome alum, chromium acetate), aldehydes (e.g., formaldehyde, glyoxal, glutaraldehyde), active vinyl compounds (e.g., 1,3,5-triacryloyl-hexahydro-s-triazine, 1,3-vinylsulfonyl-2-propanol) and active halide compounds (e.g., 2,4-dichloro-6-hydroxy-s-triazine) may be used singly or in combination.

The silver halide photographic light-sensitive material of the invention may contain a color fogging inhibitor such as hydroquinone derivative, aminophenol derivative or gallic acid derivative.

Further, colloidal silver or dyes may be used in the light-sensitive material of the invention for the purpose of anti-irradiation, antihalation, particularly, separation of spectral sensitivity distribution of each sensitive layer, and safety against a safelight.

Examples of such dyes include oxonol dyes having pyrazolone nucleus, barbituric nucleus or barbituric acid nucleus as described in U.S. Pat. Nos. 506,385, No. 1,177,429, No. 1,131,844, No. 1,338,799, No. 1,385,371, No. 1,467,214, No. 1,438,102 and No. 1,533,516, Japanese Patent Provisional Publications No. 48(1973)-85130, No. 49(1974)-114420, No. 52 (1977) -117123, No. 55 (1989) -161233 and No. 59(1984)-111640, Japanese Patent Publications No. 39 (1964)-22069, No. 43(1968)-13168 and No. 62(1987)-273527, and U.S. Pat. Nos. 3,247,127, No. 3,469,985 and No. 4,078,933; other oxonol dyes as described in U.S. Pat. Nos. 2,533,472 and No. 3,379,533, U.K. Patent No. 1,278,621, and Japanese Patent Provisional Publications No. 1(1989)-134447 and No. 1(1989)-183652; azo dyes as described in U.K. Patents No. 575,691, No. 680,631, No. 599,623, No. 786,907, No. 907,125 and No. 1,045,609, U.S. Pat. No. 4,255,326, and Japanese Patent Provisional Publication No. 59(1984)-211043; azomethine dyes as described in Japanese Patent Provisional Publications No. 50(1975)-100116 and No. 54(1979)-118247, and U.K. Patents No. 2,014,598 and No. 750,031; anthraquinone dyes as described in U.S. Pat. No. 2,865,752; arylidene dyes as described in U.S. Pat. Nos. 2,538,009, No. 2,688,541 and No. 2,538,008, U.K. Patents No. 584,609 and 1,210,252, Japanese Patent Provisional Publications No. 50(1975)-40625, No. 51(1976)-3623, No. 51(1976)-10927 and No. 54(1979)-118247, and Japanese Patent Publications No. 48(1973)-3286 and No. 59(1984)-37303; styryl dyes as described in Japanese Patent Publications No. 28(1953)-3082, No. 4491969)-16594 and No. 59(1984)-28898; triarylmethane dyes as described in U.K. Patents No. 446,538 and No. 1,335,422, and Japanese Patent Provisional Publication No. 59(1984)-288250; merocyanine dyes as described in U.K. Patents No. 1,075,653, No. 1,153,341, No. 1,284,730, No. 1,475,228 and No. 1,542,807; and cyanine dyes as described in U.S. Pat. Nos. 2,843,486 No. 3,294,539, and Japanese Patent Provisional Publication No. 1(1989)-291247. The methine compound according to the invention can be used as the above dye, and in this case, there is such an advantage that decoloration of the dye can be easily made.

For inhibiting diffusion of the above-mentioned dyes, methods described below can be utilized. For example, a ballast group is incorporated into the dye to make the dye resistant to diffusion.

Further, a method in which a hydrophilic polymer having an opposite electric charge to that of the dissociated anionic dye is added to a certain layer as a mordant and the dye is made to be locally present in the specific layer by means of interaction between the hydrophilic polymer and the dye molecule is disclosed, for example, in U.S. Pat. Nos. 2,548,564, No. 4,124,386 and No. 3,625,694.

Furthermore, a method in which a water-insoluble dye solid is used to dye a specific layer is disclosed, for example, in Japanese Patent Provisional Publications No. 56(1981)-12639, No. 55(1980)-155350, No. 5591980)-155351, No. 63(1988)-27838 and No. 63(1988)-197943, and European Patent No. 15,601.

Moreover, a method in which fine grains of a metallic salt adsorbed with a dye are used to dye a specific layer is disclosed, for example, in U.S. Pat. Nos. 2,719,088, No. 2,496,841 and No. 2,496,843, and Japanese Patent Provisional Publication No. 60(1985)-45237.

In the silver halide photographic light-sensitive material of the invention, it is preferred to provide a protective layer on the above-mentioned emulsion layer provided on a support. A back layer may be provided on the reverse side (i.e., side where the emulsion layer is not provided) of the support. The silver halide photographic light-sensitive layer may have a structure comprising a back layer, a support, an antihalation layer, an emulsion layer, an intermediate layer, a ultraviolet absorbing layer and a protective layer. In the case where a dye is added to those layers, the methine compound according to the invention is preferably used as the dye because decoloration of the dye can be easily made.

The silver halide photographic emulsion employable in the invention may contain a protective colloid. Examples of the protective colloids include gelatin; acylated gelatin such as phthalated gelatin and malonated gelatin; cellulose compounds such as carboxyethyl cellulose and carboxymethyl cellulose; soluble starch such as dextrin; hydrophilic polymers such as polyvinyl alcohol, polyvinyl pyrrolidone, polyacrylamide and polystylenesulfonic acid; plasticizers to stabilize dimension; latex polymers; and matting agents. A finished emulsion is applied onto an appropriate support, for example, a baryta paper, a resin coated paper, a synthetic paper, a triacetate film, a polyethylene terephthalate film, other plastic base or a glass plate.

Exposure of the light-sensitive material to obtain a photographic image is carried out in accordance with a conventional process. A variety of known light sources can be used for the exposure. For example, natural light (sunlight), tungsten lamp, mercury vapor lamp, xenon arc lamp, carbon arc lamp, xenon flashlamp, laser, LED and CRT can be used. The exposure time may be appropriately determined. For example, exposure of from 1/1,000 second to 1 second (this period is usually adopted for camera), exposure of from 1/104 to 1/10 second (this period is adopted in the case of using a xenon fluorescent lamp) or exposure of not shorter than 1 second can be carried out. A color filter may be used, if desired, to adjust spectral composition of the light used for the exposure. A laser light may be also employed for the exposure. Further, the light-sensitive material may be exposed to a light emitted by a phosphor excited with X rays, $\gamma$ rays or $\alpha$ rays.

The spectral sensitizing dyes (methine compounds of the formulas (I) and (II)) are used for sensitization of silver halide emulsions for various color and black and white light-sensitive materials. Examples of the silver halide emulsions include a color positive emulsion, an emulsion for color paper, a color negative emulsion, a color reversal emulsion (containing or not containing a coupler), an emulsion used for a reprophotographic light-sensitive material (e.g., lithographic film), an emulsion used for a light-sensitive material for cathode-ray tube display, an emulsion used for silver salt diffusion transfer process, an emulsion used for color diffusion transfer process, an emulsion used for Imbitio transfer process (said process being described in for example U.S. Pat. No. 2,882,156), an emulsion used for silver dye bleaching method, an emulsion used for a material for recording a print-out image (said material being described in for example U.S. Pat. No. 2,369,449), an emulsion used for a direct print image type light-sensitive material (said material being described in for example U.S. Pat. No. 3,033,682), and an emulsion used for a color light-sensitive material for heat development.

For photographic processing of the light-sensitive material of the invention, known processes as described in "Research Disclosure", No. 176, pp. 28–30 (RD-17643) can be utilized, and known processing solutions can be used. The processing temperature is usually between 18° C. and 50° C., but it may be lower than 18° C. or higher than 50° C. In accordance with the purpose, any development processes for forming a silver image (black and white photographic process) and color photographic processes including development for forming a color image can be used.

For the black and white developing solution, known developing agents such as dihydroxybenzenes (e.g., hydroquinone), 3-pyrazolidones (e.g., 1-phenyl-3-pyrazolidone) and aminophenols (e.g., N-methyl-p-aminophenol) may be used singly or in combination.

The color developing solution is usually an alkaline aqueous solution containing a color developing agent. As the color developing agent, there can be used primary aromatic amine developing agents such as phenylenediamines. Examples of the phenylenediamines include 4-amino-N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline and 4-amino-3-methyl-N-ethyl-$\beta$-ethoxyethylaniline.

Developing agents described in F. A. Mason, "Photographic Processing Chemistry", Focal Press, pp. 226–229 (1966); U.S. Pat. Nos. 2,193,015 and No. 2,592,364; and Japanese Patent Provisional Publication No. 48(1973)-64933 are also employable.

The developing solution may contain a pH buffering agent (e.g., sulfite, carbonate, borate and phosphate of alkali metal), a development inhibitor (e.g., bromide and an organic anti-fogging agent) and an anti-fogging agent, in addition to the developing agent. If necessary, the developing solution may further contain a hard water softening agent, a preservative (e.g., hydroxylamine), an organic solvent (e.g., benzyl alcohol and diethylene glycol), a development accelerator (e.g., polyethylene glycol, quaternary ammonium salt and amines), a fogging agent (e.g., a dye forming coupler, a competing coupler and sodium boron hydride), a development assisting agent (e.g., 1-phenyl-3-pyrazolidone), a viscosity imparting agent, a polycarboxylic acid type chelating agent described in U.S. Pat. No. 4,083,723, and an antioxidant described in West German Patent (OLS) No. 2,622,950.

In the color photographic processing, the photographic light-sensitive material having been subjected to color development is generally subjected to bleaching. The bleach process may be carried out simultaneously with the fix process or separately from the fix process. Examples of bleaching agents used for the bleaching solution include compounds of polyvalent metals such as iron(III), cobalt (III), chromium(VI) and copper(II), peracids, quinones and nitroso compounds. Concretely, there can be employed ferricyanides; bichromates; organic complex salts of iron(III) or cobalt-(III); complex salts of aminopolycarboxylic acids such as ethylenediamine tetraacetate, nitrotriacetic acid and 1,3-diamino-2-propanoltetraacetic acid; complex salts of organic acids such as citric acid, tartaric acid and malic acid; persulfates; permanganates; and nitrosophenol. Potassium ferricyanide, ethyelnediamine tetra iron(III) sodium complex salt and ethylenediamine tetra iron(III) ammonium complex salt are particularly useful. Ethylenediamine tetra iron(III) complex salt is useful for both a bleaching solution and a combined bleaching and fixing solution.

The bleaching solution or the bleaching and fixing solution may contain bleaching accelerators described in U.S. Pat. Nos. 3,042,520 and No. 3,241,966, and Japanese Patent Publications No. 45(1970)-8506 and No. 45(1970)-8836; thiol compounds described in Japanese Patent Provisional Publication No. 5391978)-65732; and other various additives. After the bleach process or the bleach-fix process, the light-sensitive material may be subjected to washing process, or may be subjected to stabilizing process only.

The present invention is further described by the following examples.

First, synthesis examples of the novel methine compounds (formulae (II) or (III)) according to the invention are described.

EXAMPLE 1

Synthesis of methine compound (aforementioned compound M-14; represented by the formula (II))

1) Synthesis of nitrogen-containing heterocyclic compound (M-14A) having the following structure

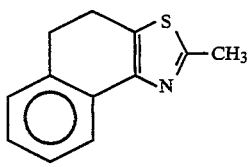

M-14A

In a flask were placed 43.8 g of α-tetralone and 50 ml of acetic acid. To the resulting mixture was dropwise added 17 ml of bromine at 40° C. over 1 hour with stirring, and the mixture was further stirred at 40° C. for 2 hours.

After the reaction was complete, to the reaction mixture were added 500 ml of water and 300 ml of ethyl acetate, and they were stirred for 30 minutes. The resulting mixture was then allowed to stand. Then, water of the lower layer was removed, 50 ml of water was newly added, and they were stirred for 30 minutes. The resulting mixture was allowed to stand, and water of the lower layer was again removed.

To the resulting solution was added 40 g of thioacetamide, the solvent was distilled off from the solution with stirring under heating, and the solution was heated at an external temperature of 170° C. for 5 hours. After cooling, the residue was purified by silica gel chromatography using dichloromethane as a developing solvent, to obtain 36 g of the compound (M-14A).

2) Synthesis of N-substituted nitrogen-containing heterocyclic compound (M-14B) having the following structure

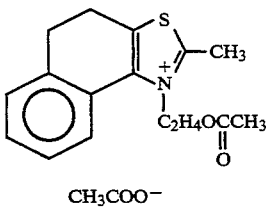

M-14B

In a round flask equipped with a stirrer and a reflux condenser were placed 20.1 g (0.10 mol) of the compound (M-14A) obtained as above and 11.4 g (0.13 mol) of ethylene carbonate and 14 ml (0.11 mol) of boron trifluoride ethyl etherate. The flask was placed in an oil bath and heated at 170° C. for 2 hours with stirring the mixture in the flask.

After the reaction was complete, the reaction mixture was cooled to room temperature, and 15 ml of acetic anhydride was added to the flask. After 1 hour, to the flask was further added 300 ml of ethyl acetate. When the mixture in the flask was stirred, yellow crystals precipitated. The crystals were collected by filtration, and the collected crystals were dried at 50° C. for 1 hour to obtain 12.1 g of pale yellow crystals (compound M-14B).

3) Synthesis of methine compound (compound M-14)

5.0 g of the pale yellow crystals (M-14B) obtained as above were added to a mixture solvent consisting of 20 ml of acetic acid, 14 ml of pyridine, 10 ml of triethylamine and 14 ml of ethyl orthopropionate, and the resulting solution was heated for 2 hours under reflux to allow it to react. The reaction solution was cooled and then poured in 600 ml of ethyl acetate. The resulting crystals were collected by filtration. The crude crystals thus obtained and 2 g of potassium iodide were dissolved in ethanol under heating. After cooling, the resulting crystals were collected by filtration, and the collected crystals were recrystallized twice from methanol and isopropanol to obtain 0.6 g of crystals of the compound (M-14).

$\lambda_{max}$: 573.1 nm (methanol)
$\epsilon$: $0.96 \times 10^5$

EXAMPLE 2

Synthesis of methine compound (aforementioned compound M-19; represented by the formula (II))

1) Synthesis of N-substituted nitrogen-containing heterocyclic compound (M-19A) having the following structure

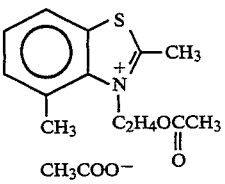

M-19A

In a round flask equipped with a stirrer and a reflux condenser were placed 16.3 g (0.10 mol) of 2,4-dimethylbenzothiazole, 11.4 g (0.13 mol) of ethylene carbonate and 14 ml (0.11 mol) of boron trifluoride ethyl etherate. The flask was placed in an oil bath and heated at 190° C. for 2.5 hours with stirring.

After the reaction was complete, the reaction mixture was cooled to room temperature, then 15 ml of acetic anhydride was added to the flask, and the mixture in the flask was stirred for 1 hour. To the flask was further added 300 ml of ethyl acetate. When the mixture in the flask was stirred, yellow crystals precipitated. The crystals were collected by filtration, and the collected crystals were dried at 50° C. for 1 hour to obtain 18.0 g of pale yellow crystals (compound M-19A).

2) Synthesis of methine compound (compound M-19)

5.0 g of the pale yellow crystals (M-19A) obtained as above were added to a mixture solvent consisting of 20 ml of acetic acid, 14 ml of pyridine, 10 ml of triethylamine and 14 ml of ethyl orthopropionate, and the resulting solution was heated for 2 hours under reflux to allow it to react. The reaction solution was cooled and then poured in 600 ml of ethyl acetate. The resulting crystals were collected by filtration. The crude crystals thus obtained and 2 g of tetrabutylammonium perchlorate were dissolved in ethanol under heating. After cooling, the resulting crystals were collected by filtration, and the collected crystals were recrystallized twice from methanol and isopropanol to obtain 0.9 g of crystals of the compound (M-19).

$\lambda_{max}$: 553.6 nm (methanol)
$\epsilon$: $1.02 \times 10^5$

EXAMPLE 3

Synthesis of methine compound (aforementioned compound M-8; represented by the formula (III))

1) Synthesis of N-substituted nitrogen-containing heterocyclic compound (M-8A) having the following structure

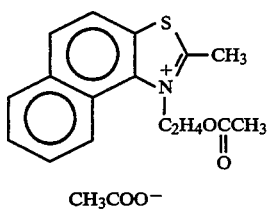

M-8A

CH$_3$COO$^-$

In a round flask equipped with a stirrer and a reflux condenser were placed 19.9 g (0.10 mol) of 2-methyl-naphtho[1,2-d]thiazole, 11.4 g (0.13 mol) of ethylene carbonate and 14 ml (0.11 mol) of boron trifluoride ethyl etherate. The flask was placed in an oil bath and heated at 170 ° C. for 2 hours with stirring of the mixture in the flask.

After the reaction was complete, the reaction mixture was cooled to room temperature, and 15 ml of acetic anhydride was added to the flask. After 1 hour, to the flask was further added 300 ml of ethyl acetate. When the mixture in the flask was stirred, yellow crystals precipitated. The crystals were collected by filtration, and the collected crystals were dried at 50° C. for 1 hour to obtain 15.2 g of pale yellow crystals (compound M-8A).

2) Synthesis of methine compound (compound M-8)

5.0 g of the pale yellow crystals (M-8A) obtained as above were added to a mixture solvent consisting of 20 ml of acetic acid, 14 ml of pyridine, 10 ml of triethylamine and 14 ml of ethyl orthopropionate, and the resulting solution was heated for 2 hours under reflux to allow it to react. The reaction solution was cooled and then poured in 600 ml of ethyl acetate. The resulting crystals were collected by filtration. The crude crystals thus obtained and 2 g of tetrabutylammoniumperchlorate were dissolved in ethanol under heating. After cooling, the resulting crystals were collected by filtration, and the collected crystals were recrystallized twice from methanol and isopropanol to obtain 0.8 g of crystals of the compound (M-8).

$\lambda_{max}$: 581.1 nm (methanol/DMF)
$\epsilon$: $1.16 \times 10^5$

EXAMPLE 4

Synthesis of methine compound (aforementioned compound M-10; represented by the formula (III))

1) Synthesis of compound (M-10A) having the following structure

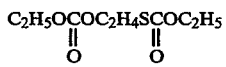

M-10A

In a flask were placed 15 g of HO—CH$_2$CH$_2$—SH and 28 ml of (CH$_3$CH$_2$)$_3$N, and to the resulting mixture in the flask was dropwise added 40 ml of ethyl chloroformate under cooling with ice. After 1 hour, to the mixture were added 300 ml of ethyl acetate and 300 ml of water, and they were stirred for 30 minutes. The mixture was then allowed to stand. Then, the water of the lower layer was removed. Thereafter, ethyl acetate was distilled off from the resulting solution under a reduced pressure, and then 36 g of the compound (M-10A) was obtained by distillation.

2) Synthesis of N-substituted nitrogen-containing heterocyclic compound (M-10B) having the following structure

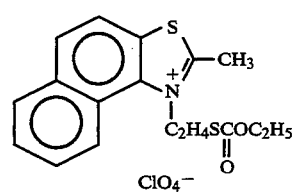

M-10B

In a round flask equipped with a stirrer and a reflux condenser were placed 19.9 g (0.10 mol) of 2-methyl-naphtho[1,2-d]thiazole, 28.9 g (0.13 mol) of the compound (M-10A) obtained as above and 14 ml (0.11 mol) of boron trifluoride ethyl etherate. The flask was placed in an oil bath and heated at 170° C. for 2 hours with stirring.

After the reaction was complete, the reaction mixture was cooled to room temperature, and 15 ml of acetic anhydride was added to the flask. After 1 hour, to the flask was further added 300 ml of ethyl acetate. When the mixture in the flask was stirred, yellow crystals precipitated. The crystals were collected by filtration, and the collected crystals and 4 g of tetrabutylammonium perchlotate were heated in ethanol. After cooling, the resulting crystals were collected by filtration, and the collected crystals were dried at 50° C. for 1 hour to obtain 17.3 g of pale yellow crystals (compound M-10B).

3) Synthesis of methine compound (compound M-10)

5.0 g of the pale yellow crystals (M-10B) obtained as above were added to a mixture solvent consisting of 20 ml of acetic acid, 14 ml of pyridine, 10 ml of triethylamine and 14 ml of ethyl orthopropionate, and the resulting solution was heated for 2 hours under reflux to allow it to react. The reaction solution was cooled and then poured in 600 ml of ethyl acetate. The resulting crystals were collected by filtration. The crudes crystal thus obtained were recrystallized twice from methanol and isopropanol to obtain 0.5 g of crystals of the compound (M-10).

$\lambda_{max}$: 581.1 nm (methanol/DMF)
$\epsilon$: $1.16 \times 10^5$

EXAMPLE 5

Synthesis of methine compound (aforementioned compound M-13; represented by the formula (III))

1) Synthesis of N-substituted nitrogen-containing heterocyclic compound (M-13A) having the following structure

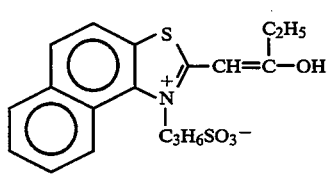

M-13A 40 g of 2-methylnaphtho[1,2-d]thiazolium-3-propane-sulfonate was suspended in 135 ml of anhydrous propionic acid, and the suspension was heated in an oil bath of 130° C. To the resulting solution was dropwise added 17.5 ml of triethylamine, and after 4 hours, the resulting solution was cooled. The solution was then subjected to decantation using three portions of 200 ml of n-hexane, and to the residue was added 5 ml of concentrated hydrochloric acid. By the addition of the concentrated hydrochloric acid, pale grey crystals precipitated. The crystals were collected by filtration, and the collected crystals were dried under vacuum to obtain 31 g (yield: 66%) of the compound (M-13A).

2) Synthesis of methine compound (compound M-13)

6.5 g of the compound (M-13A) obtained as above and 6.5 g of a Lawson reagent (B) having the following structure:

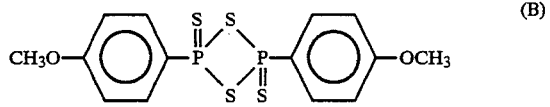

were suspended in 40 ml of toluene. To the suspension was added 5 ml of pyridine, and the resulting suspension was heated for 1 hour under reflux. After cooling, the solution was subjected to decantation using three portions of 300 ml of toluene, and to the residue (crystal) was added 12 g of methyl p-toluenesulfonate. The resulting mixture was heated at 170° C. for 3 hours. After cooling, the mixture was subjected to decantation using three portions of a mixture of 300 ml of ethyl acetate and n-hexane (ethyl acetate: n-hexane=1:1, by volume). To the resulting crystals were added 6.6 g of the compound obtained in Synthesis Example 4 (aforementioned compound M-10B) and were further added 100 ml of ethanol and 20 ml of triethylamine, and they were stirred for 2 hours. After distillation of the solvent under a reduced pressure, the residue was purified by silica gel chromatography to obtain 0.8 g of crystals of the compound (M-13).

$\lambda_{max}$: 581.0 nm (methanol)

$\epsilon$: $1.05 \times 10^5$

EXAMPLE 6

Synthesis of methine compound (the aforementioned compound M-27; represented by the formula (III))

1) Synthesis of N-substituted nitrogen-containing heterocyclic compound (M-27A) having the following structure

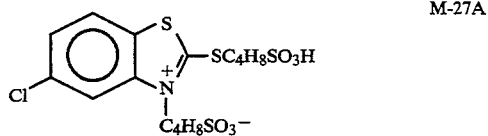

In a round flask equipped with a stirrer and a reflux condenser were placed 18.4 g (0.10 mol) of 5-chloro-2-mercaptobenzothiazole and 32.6 g (0.24 mol) of butanesultone. The flask was placed in an oil bath and heated at 160° C. for 4.5 hours under stirring.

After the reaction was complete, to the reaction mixture was added 30 ml of dimethylacetamide while cooling the mixture to room temperature. Thereafter, 280 ml of ethyl acetate was added to the mixture. When the resulting mixture was stirred, pale grey crystals precipitated. The crystals were collected by filtration, and the collected crystals were dried at 50° C. for 1 hour to obtain 44.1 g of pale yellow crystals (compound M-27A).

2) Synthesis of methine compound (compound M-27)

3.4 g of the pale yellow crystals (M-27A) and 2.9 g of the compound obtained in Synthesis Example 3 (aforementioned compound M-8A) were added to a mixture solvent of 50 ml of ethanol and 2 ml of triethylamine, and the resulting solution was refluxed for 2 hours. The solvent was distilled off from the solution under a reduced pressure, and then the residue was purified by silica gel chromatography to obtain 0.4 g of crystals of the compound (M-27).

$\lambda_{max}$: 443.5 nm (methanol)

$\epsilon$: $7.86 \times 10^4$

EXAMPLE 7

Synthesis of methine compound (the aforementioned compound m-1; represented by the formula (III))

1) Synthesis of N-substituted nitrogen-containing heterocyclic compound; 3-(2-acetoxyethyl)-methylnaphto[1,2-d]thiazoliume acetate (aforementioned compound: e-7)

In a round flask equipped with a stirrer and a reflux condenser were placed 19.9 g (0.10 mol) of 2-methylnaphto[1,2-d]thiazole, 11.4 g (0.13 mol) of ethylene carbonate and 14 ml (0.11 mol) of boron trifluoride ethyl etherate. The flask was placed in an oil bath and heated at 170° C. for 2 hours with stirring.

After the reaction was complete, the reaction mixture was cooled to room temperature, and 15 ml of acetic anhydride was added to the flask. After 1 hour, to the flask was further added 300 ml of ethyl acetate. When the mixture in the flask was stirred, pale yellow crystals precipitated. The crystals were collected by filtration, and dried at 50° C. for 1 hour to obtain 15.2 g of pale yellow crystals (e-7).

2) Synthesis of methine compound (compound m-1)

5.0 g of the pale yellow crystals (e-7) were added to a mixture solvent consisting of 20 ml of acetic acid, 14 ml of pyridine, 2 ml of triethylamine and 14 ml of ethyl orthopropinonate, and the resulting solution was refluxed for 2 hours to allow it to react. After cooling, the reaction mixture was poured into 600 ml of ethyl acetate, and the resultant crystals were collected by filteration. The crude crystals and 2 g of tetrabutylammonium perchlorate were dissolved in ethanol under heating. After cooling, the obtained crystals were recrystallized twice from methanol and isopropanol to obtain 0.8 g of crystals of the compound (m -1).

$\lambda_{max}$: 581.1 nm (methanol/DMF)

$\epsilon$: $1.16 \times 10^5$

EXAMPLE 8

Synthesis of methine compound (aforementioned compound m-20; represented by the formula (III))

1) Synthesis of N-substituted nitrogen-containing heterocyclic compound; 2-(hydroxybutenyl)naphtho[1,2-d]thiazorium 3-propansulfonate (compound A)

40 g of 2-methylnaphtho[1,2-d]thiazolium-3-propanesulfonate was suspended in 135 ml of anhydrous propionic acid, and the suspension was heated in an oil bath at 130° C. To the resulting solution was dropwise added 17.5 ml of triethylamine, and after 4 hours, the resulting solution was cooled. The solution was then subjected to decantation using three portions of 200 ml of n-hexane, and to the residue was added 5 ml of concentrated hydrochloric acid. By the addition of the concentrated hydrochloric acid, pale grey crystals precipitated. The crystals were collected by filtration, and the collected crystals were dried under vacuum to obtain 31 g (yield: 66%) of compound A.

2) Synthesis of methine compound (compound M-13)

6.5 g of the compound (M-13A) obtained as above and 6.5 g of the above-mentioned Lawson reagent were suspended in 40 ml of toluene. To the suspension was added 5 ml of pyridine, and the resulting suspension was heated for 1 hour under reflux. After cooling, the solution was subjected to decantation using three portions of 300 ml of toluene, and to the residue (crystal) was added 12 g of methyl p-toluenesulfonate. The resulting mixture was heated at 170° C. for 3 hours. After cooling, the mixture was subjected to decantations using three portions of a mixture of 300 ml of ethyl acetate and n-hexane (ethyl acetate: n-hexane=1:1, by volume). To the resulting crystals were added 6.6 g of the compound obtained in the aforementioned compound e-7 and were further added 100 ml of ethanol and 20 ml of triethylamine, and they were stirred for 2 hours. After distillation of the solvent under a reduced pressure, the residue was purified by silica gel chromatography to obtain 0.8 g of crystals of the compound (M-13).

$\lambda_{max}$: 581.0 nm (methanol)
$\epsilon$: $1.05 \times 10^5$

EXAMPLE 9

Synthesis of methine compound (aforementioned compound m-32; represented by the formula (III))

40 g of 5-chloro-2-methylbenzothiazolium-3-propanesulfonate and the aforementioned compound e-7 used in Example 7 were refluxed in a mixture solvent consisting of 50 ml of ethanol and 2 ml of triethylamine for 2 hours. After distillation of the solvent under a reduced pressure, the residue was purified by silica gel chromatography to obtain 0.8 g of crystals of the compound (m-32).

$\lambda_{max}$: 443.2 nm (methanol)
$\epsilon$: $1.05 \times 10^5$

EXAMPLE 10

The methine compounds (m-1 of Example 7, m-20 of Example 5 and m-32 of Example 8) each was dissolved in methanol to prepare the solutions of $2.0 \times 10^{-5}$ mole/liter (concentration). To 10 ml of each of the methanol solutions, 1 ml of 2N-NaOH aqueous solution was added.

After 5 minutes, absorption maximum of the solution was measured by an autographic-spectrophotometer. The results are set forth in the following table.

| Compound | Before addition of Alkali | After addition of alkali |
|---|---|---|
| m-1 | 581.1 nm | 421.1 nm |
| m-20 | 581.0 nm | 499.4 nm |
| m-32 | 443.5 nm | 365.0 nm |

As shown in the above table, addition of alkali to the aqueous solution containing the methine compound of the invention shifted the absorption maximum to the short wavelength side.

After 10 minutes, 1 ml of concentrated HCl was added to each of the methanol solutions. After 5 minutes, absorption maximum of the solution was measured using an autographic-spectrophotometer. It was observed that the absorption maximum sifted to the short wavelength side was lowered in height of the peak, and all solutions decolored.

As is apparent from the above results, the absorption maximum of the methine compound of the invention is shifted to the short wavelength side by placing it under alkaline condition, and the methine compound is decolored. Hence, the absorption maximum of the methine compound is shifted to the short wavelength side by an alkaline developing solution, and the methine compound is almost decolored or decolored to some extent. Further, when the methine compound is placed under neutral condition (after development, generally the surrounding condition is rendered neutral), it is completely decolored. Accordingly, it is apparent that the methine compound is easily decolored in a process for formation of a photographic image.

The shifting to the short wavelength is thought to be caused by the fact that the methine compound of the formula (III) is cleaved between "Y" and O (oxygen) under the alkaline condition and the oxygen atom is added to the inner conjugation chain.

The novel methine compound of the formula (II) or (III) of the invention is useful for a spectral sensitizing dye for electrophotography, a colorant, light-absorptive agent, a dye for optical disc and medicine other than the above sensitizing dye.

Subsequently, examples of the silver halide photographic light-sensitive materials using the methine compound of the invention described.

EXAMPLE 11

In a reaction vessel were placed 1,000 ml of water, 25 g of deionized osseous gelatin, 15 ml of a 50% aqueous $NH_4NO_3$ solution and 7.5 ml of a 25% aqueous $NH_3$ solution, and the mixture in the vessel was kept at 50° C. and sufficiently stirred. To the mixture were further added 750 ml of a $1N-AgNO_3$ aqueous solution and a 1N-KBr aqueous solution for 50 minutes to keep the silver electric potential during the reaction at +50 mV based on the saturated calomel electrode.

Silver bromide grains contained in the above-obtained emulsion were cubic and had side lengths of $0.78 \pm 0.06$ μm. After addition of a high-molecular flocculating agent to the emulsion, the emulsion was desalted. Then, to the emulsion were added 95 g of deionized osseous gelatin and 430 ml of water. The emulsion was adjusted to pH 6.5 and pAg 8.3 at 50° C. Thereafter, sodium thiosulfate was added to the emulsion to ripen the emulsion at 55° C. for 50 min. so that the emulsion had an optimum sensitivity. As a result, 0.74 mol of silver bromide was present in 1 kg of the emulsion.

50 g of the emulsion was taken. To each portion of the emulsion was added sensitizing dyes, respectively, as shown in Table 1, and were further added 10 mg of 4-hydroxy-6-methyl-1,3,3a,7-tetrazaindene, 15 g of a 10% gel of deionized gelatin and 55 ml of water. The resulting emulsion was coated over a polyethylene terephthalate film base in the following manner.

The emulsion was coated in such an amount that the amount of silver would be 2.3 g/m² and the amount of gelatin would be 3.5 g/m². At the same time, over the coated emulsion layer was coated an aqueous solution containing, as host components, 0.22 g/L of sodium dodecylbenzenesulfonate, 0.50 g/L of sodium p-sulfostyrene homopolymer, 3.1 g/L of 2,4-dichloro-6-hydroxy-1,3,5-triazine sodium salt and 50 g/L of gelatin in such an amount that the amount of gelatin would be 1.0 g/m².

Each of the samples thus obtained was exposed to light using a tungsten light source (color temperature: 2,854K) through an interference filter of 400 nm and an yellow sharp cut filter SC-48 available from Fuji Photo Film Co., Ltd. (i.e., filter having a transmission of about 35% at 480 nm and transmitting a light of longer wavelength than about 460 nm) with a step wedge.

Each of the samples thus exposed was developed in a developing solution having the following composition at 20° C. for 4 minutes, and then successively subjected to stopping (30 seconds in an aqueous solution of acetic acid having a pH value of 2), fixing (1 minute using SUPER FUJIFIX—tradename—available from Fuji Photo Film Co., Ltd.) and washing for 10 minutes. Then, each sample was measured on the density using a P-type densitometer available from Fuji Photo Film Co., Ltd. to obtain a sensitivity at 400 nm (SB) and an yellow filter sensitivity (SY). The results are set forth in Table 1.

(Composition of developing solution)

| | |
|---|---|
| Water | 700 ml |
| Metol | 3.1 g |
| Anhydrous sodium sulfite | 45.0 g |
| Hydroquinone | 12.0 g |
| Sodium carbonate (monohydrate) | 79.0 g |
| Potassium bromide | 1.9 g |
| Water to make up to | 1,000 ml |

In the use of the developing solution, to the developing solution was added water in an amount (by weight) of two times of the amount of the solution.

The reference point of the optical density for determining the sensitivity is a density point of "fogging+0.2", and the sensitivity is expressed by a reciprocal number of the exposure amount required for giving the sensitivity. The relative sensitivity at 400 nm in Table 1 is expressed by a relative value based on the sensitivity of the sample 1 (control) containing no sensitizing dye being 100; the relative yellow sensitivity of each of the samples 2 to 13 is expressed by a relative value based on the sensitivity of the sample 2 being 100; and the relative yellow sensitivity of each samples 14 to 19 is expressed by a relative value based on the sensitivity of the sample 14 being 100.

Further, each of the samples was successively subjected to developing, stopping, fixing and washing in the same manner as described above without subjecting it to exposure, and was dried at 20° C. in a dark room. Then, each sample was measured on the stain caused by the sensitizing dye remaining after the processing. The measurement of the stain was carried out using the control sample as a reference sample by means of an autographic spectrophotometer U-3500 available from Hitachi, Ltd. In Table 1, an absorption density at the maximum absorption wavelength of the absorption by the remaining sensitizing dye is given as the stain density.

TABLE 1

| Sample No. | Sensitizing dye Kind: Amount ($\times 10^{-4}$ mol/molAg) | Relative sensitivity at 400 nm (SB) | Relative yellow sensitivity (SY) | Stain density |
|---|---|---|---|---|
| 1 | — | 100 (reference) | — | 0.0000 (reference) |
| 2 | A: 1.5 | 60.3 | 100 (reference) | 0.0512 |
| 3 | A: 3.0 | 15.1 | 39.8 | 0.0969 |
| 4 | M-7: 1.5 | 74.1 | 102.3 | 0.0000 |
| 5 | M-7: 3.0 | 19.1 | 57.5 | 0.0000 |
| 6 | M-8: 1.5 | 70.7 | 81.3 | 0.0000 |
| 7 | M-8: 3.0 | 17.8 | 61.7 | 0.0001 |
| 8 | M-9: 1.5 | 69.2 | 100.0 | 0.0000 |
| 9 | M-9: 3.0 | 18.2 | 67.6 | 0.0000 |
| 10 | M-12: 1.5 | 72.4 | 87.1 | 0.0159 |
| 11 | M-12: 3.0 | 23.4 | 89.1 | 0.0354 |
| 12 | M-13: 1.5 | 74.1 | 93.3 | 0.0356 |
| 13 | M-13: 3.0 | 17.0 | 97.7 | 0.0755 |

Structures of the dyes (A) and (B) for comparison set forth in the Table 1 and the dye (C) which will be used later in Example 5 are described below.

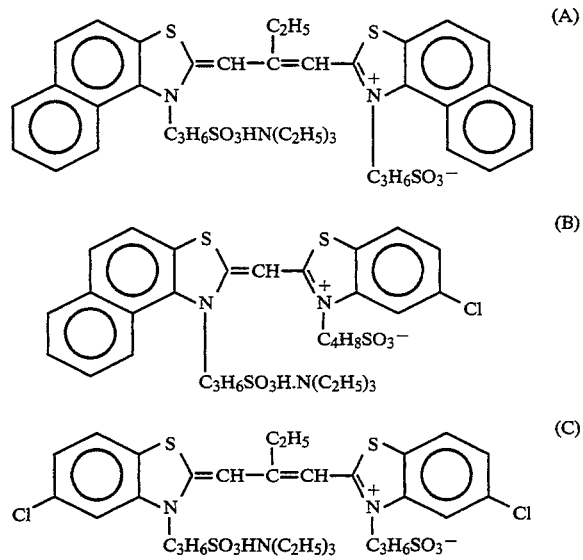

In the samples containing the sensitizing dyes according to the invention, any stain caused by the sensitizing dyes after the developing process was not observed as shown in Table 1. Further, these sensitizing dyes have high spectral sensitivities (corresponding to yellow sensitivity in Table 1) almost the same as those of the sensitizing dyes for comparison which are known as sensitizing dyes which give high spectral sensitivities to silver halides, and therefore the sensitizing dyes have features that they gave no stain or extremely reduced stain after the developing process. Sensitizing dyes which give stain of low level have been heretofore disclosed, but those sensitizing dyes only provide spectral sensitivity of very low level as compared with the sensitizing dyes for comparison in Table 1. If the spectral sensitivity is sacrificed, it is very easy to reduce stain given after the developing process. However, such means cannot be applied to various silver halide light-sensitive materials requiring high spectral sensitivity. As is evident from the results set forth in Table 1, the light-sensitive materials of the present invention are excellent ones containing sensitizing dyes which provide high spectral sensitivities as well as give stain of extremely low level.

EXAMPLE 12

(Preparation of emulsion)

To a mixture of 1 liter of water, 30 g of gelatin and 6 g of potassium bromide in a container were added an aqueous solution of silver nitrate (silver nitrate: 5 g) and an aqueous solution of potassium bromide containing 0.15 g of potassium iodide with stirring for 1 minute according to a double jet method. Further, to the container were added an aqueous solution of silver nitrate (silver nitrate: 145 g) and an aqueous solution of potassium bromide containing 4.2 g of potassium iodide according to a double jet method. In this addition stage, the flow rate of each solution was accelerated so that the flow rate at the time of completion of the addition was five times the flow rate at the time of initiation of the addition. After the addition was complete, the soluble salts were removed from the emulsion by a sedimentation method at 35° C., and the temperature of the emulsion was made to 40° C. To the emulsion was further added 75 g of gelatin to adjust a pH value of the emulsion to 6.7. The resulting emulsion contained tabular grains having a diameter of projected area of 0.98 $\mu$m and a mean thickness of 0.138 $\mu$m, and a content of the silver iodide in the emulsion was 3% by mol. The emulsion was then subjected to chemical sensitization (sulfur sensitization).

(Preparation of photographic material 101)

A gelatin aqueous solution containing gelatin, polyacrylamide having an average molecular weight of 8,000, sodium polystyrenesulfonate, fine grains of polymethylmethacrylate (mean grain size: 3.0 $\mu$m), polyethylene oxide, a hardening agent was used as a coating solution for forming a surface protective layer.

To the emulsion obtained in the above was added a sensitizing dye as shown in Table 2. Further, to the emulsion were added stabilizers (4-hydroxy-6-methyl-1,3,3a,7-tetrazaindene, 2,6-bis(hydroxyamino)-4-diethylamino-1,3,5-triazine and nitrone), a dry fogging inhibitor (trimethylolpropane), a coating aid, and a hardening agent to prepare a coating solution. Both sides of a polyethylene terephthalate support were simultaneously coated with this coating solution (emulsion) and the above-obtained coating solution for a surface protective layer, respectively, and the support with the coated solutions was dried to prepare a photographic material. The amount of silver applied onto the photographic material was 2 g/m$^2$ per one surface.

(Preparation of development processing kit)

A development processing kit (concentrated liquid) composed of the following part (A), part (B) and part (C) was prepared.

| Part (A) | |
|---|---|
| Potassium hydroxide | 291 g |
| Potassium sulfite | 442 g |
| Sodium hydrogencarbonate | 75 g |
| Boric acid | 10 g |
| Diethylene glycol | 120 g |
| Ethylenediaminetetraacetic acid | 17 g |
| 5-Methylbenzotriazole | 0.6 g |
| Hydroquinone | 300 g |
| 1-Phenyl-4,4-dimethyl-3-pyrazolidone | 20 g |
| Water to make up to | 2.5 l |
| pH | 11.0 |

The amount of each component is based on 10 liters of the developing solution (used solution).

| Part (B) | |
|---|---|
| Triethylene glycol | 20 g |
| 5-Nitroindazole | 2.5 g |
| Glacial acetic acid | 3 g |
| 1-Phenyl-3-pyrazolidone | 15 g |
| Water to make up to | 250 ml |

The amount of each component is based on 10 liters of the developing solution (used solution).

| Part (C) | |
|---|---|
| Glutaraldehyde | 99 g |
| Sodium metabisulfite | 126 g |
| Water to make up to | 250 ml |

The amount of each component is based on 10 liters of the developing solution (used solution).

Further, a starter having the following composition was prepared.

| Starter | |
|---|---|
| Glacial acetic acid | 270 g |
| Potassium bromide | 300 g |
| Water to make up to | 1.5 l |

(Preparation of developing solution)

To about 6 liters of water were successively added 2.5 liters of the part (A), 250 ml of the part (B) and 250 ml of the part (C) with stirring to dissolve them therein, and to the resulting solution was finally added water to obtain 10 liters of a developing solution.

Then, to the developing solution was added the above-mentioned starter in an amount of 20 ml per 1 liter of the developing solution.

For fixing of the photographic material, Fuji F available from Fuji Photo Film Co., Ltd. was used.

For washing of the photographic material, water containing 0.5 g/L of disodium ethylenediaminetetraacetate dihydrate (mildew proofing agent) was used.

Subsequently, the photographic material was subjected to the following developing process in a roller transfer type automatic developing machine system.

| Process | Temperature | Period |
|---|---|---|
| Developing | 35° C. | 12.5 seconds |
| Fixing | 30° C. | 10 seconds |
| Washing and squeegee | 20° C. | 12.5 seconds |
| Drying | 50° C. | 12.5 seconds |

After the above process, the stain caused by the sensitizing dye remaining in each sample (light-sensitive material) was measured in the same manner as described in Example 1. The results are set forth in Table 2 as the stain density.

The samples 3 and 4 according to the invention are excellent because they are lower in the stain density than the sample 2 for comparison, and the sample 6 of the invention is also excellent because it is extremely lower in the stain density than the sample 5 for comparison.

TABLE 2

| Sample No. | Sensitizing dye Kind: Amount ($\times 10^{-4}$ mol/molAg) | Stain density | Remark |
|---|---|---|---|
| 1 | — | 0.0000 (reference) | for control |
| 2 | A: 3.5 | 0.1624 | for comparison |
| 3 | M-8: 3.5 | 0.0001 | present invention |
| 4 | M-10: 3.5 | 0.0004 | present invention |
| 5 | B: 7.8 | 0.3300 | for comparison |
| 6 | M-29: 7.8 | 0.1760 | present invention |

EXAMPLE 13

To a gelatin aqueous solution kept at 50° C. was added $4 \times 10^{-7}$ mol (in terms of silver) of potassium iridium(III) hexachloride, and were further added simultaneously an aqueous solution of silver nitrate and an aqueous solution containing potassium iodide and potassium bromide over 60 minutes in the presence of ammonia, while keeping a pAg value at 7.8, to prepare a cubic grain monodispersed emulsion containing grains having a mean grain diameter of 0.30 μm and having a content of silver iodide of 2% by mol. To the emulsion was added a high-molecular flocculating agent to desalt the emulsion by a flocculation method. To the emulsion was further added a hypo and the emulsion was kept at 60° C. to perform chemical ripening of the emulsion.

To the emulsion obtained in the above was added a sensitizing dye as shown in Table 3. To the emulsion were added the following hydrazine derivative in an amount of 1.3 g based on 1 mol of silver and polyethylene glycol (molecular weight: about 1,000) in an amount of 300 g based on 1 mol of silver, and were further added a dispersion of 5-methylbenzotriazole, 4-hydroxy-6-methyl-1,3,3a,7-tetrazaindene and polymethyl acrylate, and 2-hydroxy-1,3,5-triazine sodium salt. Furthermore, to the emulsion was added 1,3-divinylsulfonyl-2-propanol as a hardening agent in such an amount that the swelling percentage would be 120%.

Hydrazine derivative

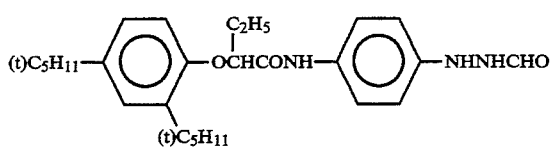

The coating solution thus prepared was coated over a polyethylene terephthalate film support simultaneously with coating of a protective layer (Example 11) in such an amount that the amount of silver would be 3.5 g/m² and the amount of gelatin (in both of the emulsion layer and the protective layer) would be 3.0 g/m², to obtain a photographic film.

The photographic film was exposed to light using a 150-ray magenta contact screen through an exposure wedge for sensitometry, then developed in a developing solution having the following composition at 40° C. for 15 seconds, and then successively subjected to fixing using a fixing solution (GR-F1 available from Fuji Photo Film Co., Ltd.), washing and drying.

The automatic developing machine used herein was set to work for 65 seconds in Dry to Dry system.

| (Composition of developing solution) | |
|---|---|
| Tetrasodium ethylenediaminetetraacetate | 1.0 g |
| Sodium hydroxide | 9.0 g |
| 5-Sulfosalicylic acid | 44.0 g |
| Potassium sulfite | 100.0 g |
| 5-Methylbenzotriazole | 0.5 g |
| Potassium bromide | 6.0 g |
| N-Methyl-p-aminophenol ½.H₂SO₄ | 0.4 g |
| Hydroquinone | 54.0 g |
| Sodium p-toluenesulfonate | 30.0 g |
| Water    to make up to | 1 liter |
| pH | 11.7 |

The washing water was replenished with 250 ml of replenisher per one sheet having a size of 20 inches × 24 inches. The degree of color remaining (stain) after the above processing was measured in the same manner as described in Example 11, and the results are set forth in Table 3 in terms of the stain density.

In the case of using the light-sensitive materials of the invention, the stain is extremely low as in the case of the aforementioned examples.

TABLE 3

| Sample No. | Sensitizing dye Kind: Amount ($\times 10^{-4}$ mol/molAg) | Stain density | Remark |
|---|---|---|---|
| 1 | — | 0.0000 (reference) | for control |
| 2 | A: 2.0 | 0.0985 | for comparison |
| 3 | M-8: 2.0 | 0.0003 | present invention |
| 4 | M-9: 2.0 | 0.0004 | present invention |
| 5 | B: 3.6 | 0.1922 | for comparison |
| 6 | M-29: 3.6 | 0.0792 | present invention |

EXAMPLE 14

A silver halide emulsion of silver chlorobromide (silver bromide: 5% by mol, mean grain diameter: 0.25 μm) containing $1 \times 10^{-5}$ mol of Rh per 1 mol of silver was prepared.

To the emulsion was added a sensitizing dye as shown in Table 4. Further, to the emulsion were added 2-hydroxy-4,6-dichloro-1,3,5-triazine sodium salt as a hardening agent and potassium polystyrenesulfonate as a thickening agent, and the resulting emulsion was applied on a polyethyelne terephthalate film in such an amount that the amount of silver would be 4 g/m². On the emulsion layer was applied a gelatin solution in such an amount that the amount of gelatin would be 1.0 g/m², to form a protective layer. Sodium p-dodecylbenzenesulfonate was used as a coating aid for the protective layer, and the same thickening agent as for the emulsion layer was used for the protective layer.

Each of the samples thus obtained was exposed to light using a printer (P-607 type produced by Dainippon Screen Co., Ltd.) through an optical wedge, and then subjected to developing process using the following developing solution and the following fixing solution.
(Developing solution)

Developing solution LD-8-35 available from Fuji Photo Film Co., Ltd. (38° C., 20 seconds)
(Fixing solution)
Fixing solution LF308 available from Fuji Photo Film Co., Ltd.
(Automatic developing solution)
FD-800RA available from Fuji Photo Film Co., Ltd.

The results on the stain density measured in the same manner as described in the aforementioned examples are set forth in Table 4. As is evident from the results set forth in Table 4, the stain is extremely low in the case of using the light-sensitive materials of the invention.

TABLE 4

| Sample No. | Sensitizing dye Kind: Amount ($\times 10^{-4}$ mol/molAg) | Stain density | Remark |
| --- | --- | --- | --- |
| 1 | — | 0.0000 | for control (reference) |
| 2 | B: 8.2 | 0.4112 | for comparison |
| 3 | M-29: 8.2 | 0.1857 | present invention |
| 4 | M-30: 8.2 | 0.0409 | present invention |

EXAMPLE 15

On a cellulose triacetate film support having been provided with a subbing layer was coated layers having the following compositions in the superposed form, to prepare a multilayer color light-sensitive material 1101.
(Composition of light-sensitive layers)

The value for each component means an amount expressed by g/m$^2$, and the value for the silver halide emulsion means an amount in terms of silver. The value for the sensitizing dye means an amount (by mol) based on 1 mol of the silver halide contained in the same layer.

The first layer (first red sensitive emulsion layer)

| | |
| --- | --- |
| Monodispersed silver iodobromide emulsion [silver iodide: 6 mol %; mean grain diameter: 0.6 μm; grain size distribution (coefficient of variation): 0.15] | 0.55 (silver) |
| Sensitizing dye A | $1.8 \times 10^{-5}$ |
| Sensitizing dye B | $3.1 \times 10^{-4}$ |
| Ex-2 | 0.350 |
| HBS-1 (tricresyl phosphate) | 0.005 |
| EX-10 | 0.020 |
| Gelatin | 1.45 |

EX-2:

[Chemical structure: naphthalene with OH, CONH(CH$_2$)$_3$OC$_{12}$H$_{25}$(n), and (i)C$_4$H$_9$OCNH substituents]

EX-10:

[Chemical structure with (t)C$_5$H$_{11}$ groups, OCH$_2$CONH, OH, NHCOC$_3$F$_7$(n), HO, CONHC$_3$H$_7$(n), and thiadiazole ring]

R = SCHCOOCH$_3$
     |
     CH$_3$

The second layer (second red sensitive emulsion layer)

| | |
| --- | --- |
| Tabular silver iodobromide emulsion [silver iodide: 10 mol %; mean grain diameter: 0.7 μm; mean aspect ratio: 5.5; mean thickness: 0.2 μm] | 1.0 (silver) |
| Sensitizing dye A | $1.4 \times 10^{-5}$ |
| Sensitizing dye C | $2.3 \times 10^{-4}$ |
| EX-2 | 0.400 |
| EX-10 | 0.015 |
| Gelatin | 1.50 |

The third layer (third red sensitive emulsion layer)

| | |
| --- | --- |
| Silver iodobromide emulsion [silver iodide: 16 mol %; mean grain diameter: 1.1 μm] | 1.60 (silver) |
| Sensitizing dye A | $1.4 \times 10^{-5}$ |
| Sensitizing dye C | $2.4 \times 10^{-4}$ |
| EX-4 | 0.120 |
| HBS-1 | 0.22 |
| HBS-2 (dibutyl phthalate) | 0.10 |
| Gelatin | 2.00 |

EX-4:

[Chemical structure: naphthalene with OH, CONH(CH$_2$)$_3$OC$_{12}$H$_{25}$(n), (i)C$_4$H$_9$OOCNH, and OCH$_2$CH$_2$SCH$_2$COOH substituents]

The fourth layer (first protective layer)

| | |
| --- | --- |
| Silver iodobromide emulsion [silver iodide: 1 mol %; mean grain diameter: 0.07 μm] | 0.5 (silver) |
| U-4 | 0.11 |
| U-5 | 0.17 |
| HBS-1 | 0.90 |
| Gelatin | 1.20 |

U-4:

[Chemical structure: copolymer with CH$_3$, COOCH$_2$CH$_2$OCO, CH=C(CN), and COOCH$_3$ groups]

U-5:

[Chemical structure with C$_2$H$_5$, N—CH=CH—CH=C, COOR, SO$_2$-phenyl groups]

R = C$_8$H$_{17}$

-continued

The fifth layer (second protective layer)

| | |
|---|---|
| Grains of polymethyl acrylate (diameter: about 1.5 μm) | 0.54 |
| S-1 | 0.15 |
| S-2 | 0.05 |
| Gelatin | 0.90 |

To each of the above layers were added a gelatin hardening agent H-1 and a surface active agent in addition to the above-mentioned components.

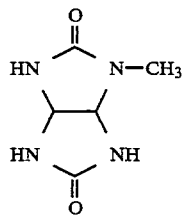  S-1

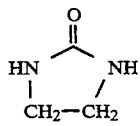  S-2

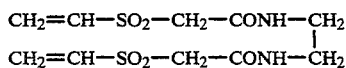  H-1

The above procedure was repeated except for replacing the sensitizing dye A with the sensitizing dye M-13 and replacing the sensitizing dye C with the sensitizing dye M-19, to prepare a color light-sensitive material 1102. Further, the above procedure was repeated except for adding no sensitizing dye to each emulsion layer, to prepare a color light-sensitive material 1103 as a control.

Each of the three kinds of samples obtained as above was subjected to the following developing process without subjecting it to exposure process.

| Process | Period (sec) | Temperature (°C.) | Replenisher (ml/m²) | Volume of the Tank |
|---|---|---|---|---|
| Color developing | 120 | 38 | 390 | 10 l |
| Bleach | 45 | 38 | 270 | 4 l |
| Bleach-fix | 90 | 38 | 530 | 8 l |
| Washing (1) | 15 | 35 | * | 4 l |
| Washing (2) | 15 | 38 | 270 | 4 l |
| Stabilizing | 15 | 38 | 270 | 4 l |
| Drying | 75 | 55 | — | — |

*: Counter current replenishing system in which the overflowed liquid of the washing bath (2) was introduced into the washing bath (1).

In the above, the time required for the wet process including various steps of from immersion of the light-sensitive material to drawing it from the stabilizing solution was 5 minutes. The total amount of the replenishers was 1,730 ml.

| Color developing solution | Mother liquor | Replenisher |
|---|---|---|
| Diethylenetriaminepentaacetic acid | 1.0 g | 1.1 g |
| 1-Hydroxyethylidene-1,1-diphosphonic acid | 3.0 g | 3.2 g |
| Sodium sulfite | 4.0 g | 5.8 g |
| Potassium carbonate | 30.0 g | 37.0 g |
| Potassium bromide | 1.4 g | — |

-continued

| Color developing solution | Mother liquor | Replenisher |
|---|---|---|
| Potassium iodide | 1.5 mg | — |
| Hydroxylaminesulfate | 2.4 g | 3.5 g |
| 4-(N-Ethyl-N-β-hydroxyethylamino)-2-methylanilinesulfate | 4.5 g | 7.2 g |
| Water (tap water) to make up to | 1.0 L | 1.0 l |
| pH | 10.05 | 10.20 |

| Bleaching solution | Mother liquor | Replenisher |
|---|---|---|
| Ammonium ethylenediaminetetraacetate Fe(II) dihydrate | 160.0 g | Same |
| Disodium ethylenediaminetetraacetate | 10.0 g | Same |
| Ammonium bromide | 160.0 g | Same |
| Ammonium nitrate | 10.0 | Same |
| Bleaching accelerator | 0.010 mol | Same |
| Ammonia water (27%) | 5.0 ml | Same |
| Water (tap water) to make up to | 1.0 L | Same |
| pH | 5.3 | Same |

Bleaching accelerator:
$[(CH_3)_2N-CH_2-CH_2-S)_2].2HCl$

| Bleach-Fix solution | Mother liquor | Replenisher |
|---|---|---|
| Ammonium ethylenediaminetetraacetate Fe(II) dihydrate | 80.0 g | Same |
| Disodium ethylenediaminetetraacetate | 5.0 g | Same |
| Ammonium sulfite | 15.0 g | Same |
| Aqueous solution of ammonium thiosulfate (700 g/l) | 300.0 ml | Same |
| Ammonia water (27%) | 6.0 l | Same |
| Water to make up to | 1.0 L | Same |
| pH | 7.2 | Same |

Washing water (for mother liquid and replenisher)

Tap water was passed through a mixed-bed system column charged with a strongly acidic cation exchange resin of H type (Amberlite IR-120B available from Rohm & Haas Co.) and an anion exchange resin of OH type (Amberlite IR-400 available from Rohm & Haas Co,) so that the tap water contained calcium in an amount of 0.3 mg/L and magnesium in an amount of not less than 0.1 mg/L and had pH 6.5 and a conductivity of 5.0 μs/cm.

| Stabilizing solution | Mother liquor | Replenisher |
|---|---|---|
| Formalin | 1.0 ml | Same |
| Polyoxyethylene-p-monononylphenyl ether (mean polymerization degree: 10) | 0.3 g | Same |
| Disodium ethylenediaminetetraacetate | 0.05 g | Same |
| Water (tap water) to make up to | 1.0 L | Same |
| pH | 5.0–8.0 | Same |

Each of the samples having been developed as described above was measured on the stain density in the same manner as described in Example 11. As a result, the stain density given in the case of using the sample 1101 (sample for comparison) was 0.0431, but the stain density given in the case of using the sample 1102 (sample of the invention) was 0.0214, in the case where the stain density given in the case of using the sample 1103 (control) was reference. Accordingly, the stain in the sample of the invention was reduced by half than that in the sample for comparison.

EXAMPLE 16

On a paper support having been coated with polyethylene on both sides were provided the following layers to prepare a color photographic paper sample 201. Coating solutions for forming each layers were prepared in the following manner.

(Preparation of coating solution for the first layer)

19.1 g of the following yellow coupler (ExY), 4.4 g of the following color image stabilizer (Cpd-1) and 0.7 g of the following color image stabilizer (Cpd-7) were dissolved in 27.2 cc of ethyl acetate and 8.2 g of the following solvent (Solv-3). The resulting solution was emulsified and dispersed in 185 cc of a 10% gelatin aqueous solution containing 8 cc of 10% sodium dodecylbenzenesulfonate.

Ex-Y

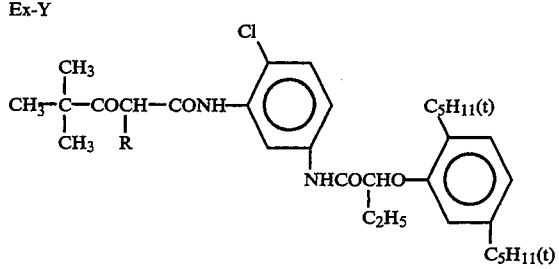

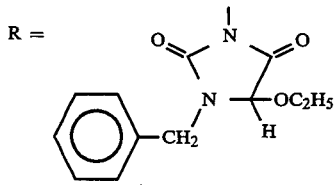

(a)

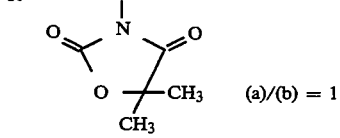

(b)

(a)/(b) = 1

Cpd-1

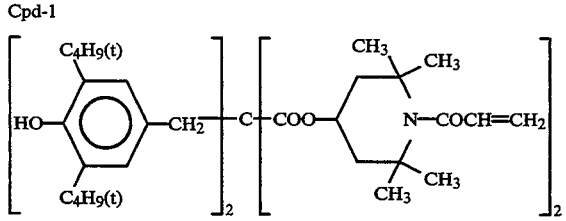

Cpd=7

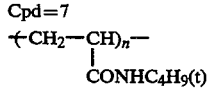

Solv-3

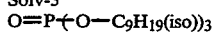

Separately, to a silver chlorobromide emulsion [cubic, mean grain size: 0.88 μm; grain size distribution (coefficient of variation): 0.08; 0.2 mol % of silver bromide being locally present on grain surfaces] was added the aforementioned sensitizing dye B in an amount of $4.0 \times 10^{-4}$ mol per 1 mol of silver. Further, to other silver chlorobromide emulsion [cubic, mean grain size: 0.70 μm; grain size distribution (coefficient of variation: 0.10; 0.2 mol % of silver bromide being locally present on grain surfaces] was added the aforementioned sensitizing dye B in an amount of $50 \times 10^{-4}$ mol per 1 mol of silver. The resulting two kinds of emulsions were mixed with each other in a mixing ratio of 3:7 (emulsion of large-sized grains: emulsion of small-sized grains, by mol in terms of silver), and the mixture was subjected to sulfur sensitization. To the resulting emulsion was added the aforementioned dispersion to prepare a coating solution for forming the first layer having the following composition.

Coating solutions for forming the second and third layers were prepared in the same manner as described above. As a gelatin hardening agent for each layer, 1-oxy-3,5-dichloro-s-triazine sodium salt was used.

[Composition of each layer]

The composition of each layer and the amount (in terms of $g/m^2$) of each component are described below. The value for the silver halide emulsion means an amount in terms of silver.

Support

Polyethylene-coated paper

Polyethylene on the first layer side included a white pigment ($TiO_2$) and a blue dye (ultramarine).

| The first layer | |
|---|---|
| The aforementioned silver chlorobromide emulsion | 0.30 |
| Gelatin | 1.86 |
| Yellow coupler (ExY) | 0.82 |
| Color image stabilizer (Cpd-1) | 0.19 |
| Solvent (Solv-3) | 0.35 |
| Color image stabilizer (Cpd-7) | 0.06 |
| The second layer (Ultraviolet absorbing layer) | |
| Gelatin | 0.53 |
| Ultraviolet absorbent (UV-1) | 0.16 |
| Color stain inhibitor (Cpd-5) | 0.02 |
| Solvent (Solv-5) | 0.08 |

Ultraviolet absorbent (UV-1):

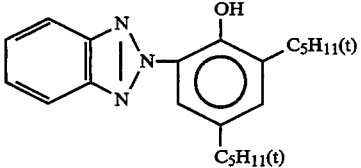

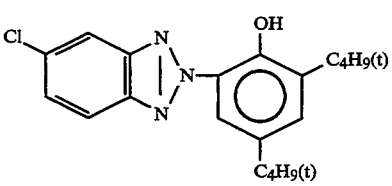

Color stain inhibitor (Cpd-5):

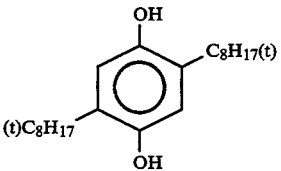

Solvent (Solv-5):

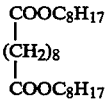

| The third layer | |
|---|---|
| Gelatin | 1.33 |

| -continued | |
|---|---|
| Acryl-modified copolymer of polyvinyl alcohol (modification degree: 17%) | 0.17 |
| Liquid paraffin | 0.03 |

The above procedure was repeated except for replacing the sensitizing dye B with the sensitizing dye M-13 to prepare a color photographic paper sample 202. Further, the above procedure was repeated except for using no sensitizing dye to prepare a sample 203.

Then, each of the samples was subjected to the following continuous processing (running test) using a paper processing machine without subjecting it to exposure process, until the amount of the replenisher became two times the volume of the tank in the color developing process.

| Process | Temperature (°C.) | Period (sec) | Replenisher (ml/m²) | Volume of the Tank |
|---|---|---|---|---|
| Color developing | 38 | 20 | 16 | 17 L |
| Bleach-fix | 35–38 | 20 | 215 | 17 L |
| Rinsing (1) | 35–38 | 7 | * | 10 L |
| Rinsing (2) | 35–38 | 7 | * | 10 L |
| Rinsing (3) | 35–38 | 6 | 350 | 10 L |
| Drying | 70–80 | 30 | | |

*: Counter current replenishing system in which the overflowed liquid of the rinsing bath (3) is introduced into the rinsing bath (1) and the overflowed liquid of the rinsing bath (1) is introduced into the rinsing bath (2).

The composition of each processing solution is as follows.

| Color developing solution | Mother liquor | Replenisher |
|---|---|---|
| Water | 800 ml | 800 ml |
| Ethylenediamine-N,N,N,N-tetramethylenephosphonic acid | 1.5 g | 2.0 g |
| Potassium bromide | 0.015 g | — |
| Triethanolamine | 8.0 g | 12.0 g |
| Sodium chloride | 1.4 g | — |
| Potassium carbonate | 25 g | 25 g |
| N-ethyl-N-(β-methanesulfonamidoethyl)-3-methyl-4-aminoanilinesulfate | 5.0 g | 7.0 g |
| N,N-bis(carboxymethyl)hydrazine | 5.5 g | 7.0 g |
| Water to make up to | 1,000 ml | 1.000 ml |
| pH (25° C.) | 10.05 | 10.45 |

| Bleach-Fix solution | Mother liquor | Replenisher |
|---|---|---|
| Water | 400 ml | Same |
| Ammonium thiosulfate (70%) | 1,000 ml | Same |
| Sodium sulfite | 17 g | Same |
| Ammonium ethylenediaminetetraacetate Fe(III) | 55 g | Same |
| Disodium ethylenediaminetetraacetate | 5 g | Same |
| Ammonium bromide | 40 g | Same |
| Water to make up to | 1,000 ml | Same |
| pH (25° C.) | 6.0 | Same |

Rinsing liquid (for mother liquor and replenisher)

Ion exchanged water (containing calcium and magnesium in each amount of not more than 3 ppm)

Using the sample 203 (control) having been developed as a reference sample, the reflection density of an image provided by each of the sample 201 (sample for comparison) and the sample 202 (sample of the invention) was measured by means of an autographic spectrophotometer U-3400 (produced by Hitachi, Ltd.) equipped with a spherical integrator. As a result, the absorption density at the maximum wavelength of absorption by the sensitizing dye remaining after the processing of the sample 202 was lower by 0.055 than that of the sample 201, namely, it was about 16% of the value of the sample 201. Accordingly, the sample 202 was remarkably improved.

EXAMPLE 16

(1. Preparation of silver halide emulsion)

In 1 liter of water was dissolved 40 g of gelatin. To the resulting solution in a container warmed at 53° C. were added 5 of of sodium chloride, 0.4 g of potassium bromide and 60 mg of the following compound (A). To the container was further added 1,000 ml of an aqueous solution containing 200 g of silver nitrate, hexachloroiridium(III) acid potassium salt (wherein the molar ratio of iridium to final silver halide was $10^{-7}$) and 1,080 ml of an aqueous solution containing 21 g of sodium chloride and 100 g of potassium bromide according to a double jet method, to prepare a monodispersed emulsion of cubic silver chlorobromide grains (mean grain size: 0.35 μm). After desalting of the emulsion, 40 g of gelatin was added to the emulsion so that the emulsion had a pH value of 6.0 and a pAg of value of 8.5. Then, to the emulsion were added 2.5 mg of sodium thiosulfate and 4 mg of chloroaurate to perform chemical sensitization at 60° C. Thereafter, 0.2 g of 4-hydroxy-6-methyl-1,3,3a,7-tetrazaindene was added to the emulsion, and the resulting emulsion was rapidly cooled until it solidified.

Compound (A)

(2. Preparation of coating solution for emulsion layer)

To 1,000 g of the above emulsion in a container warmed at 40° C. were added additives to prepare a coating solution for forming an emulsion layer having the following composition.

| Composition of a coating solution for an emulsion layer | |
|---|---|
| a. Emulsion | 1,000 g |
| b. Spectral sensitizing dye (2) | $1.2 \times 10^{-4}$ mol |
| c. Supersensitizer (3) | $0.8 \times 10^{-3}$ mol |
| d. Storage life improving agent | $1 \times 10^{-3}$ mol |
| e. Polyacrylamide (molecular weight: 40,000) | 7.5 g |
| f. Trimethylolpropane | 1.6 g |
| g. Sodium polystyrenesulfonate | 1.2 g |
| h. Latex of poly(ethyl acrylate/methacrylic acid) | 12 g |
| i. N,N'-ethylenebis(vinylsulfonacetamide) | 3.0 g |
| j. 1-Phenyl-5-mercaptotetrazole | 50 mg |

Spectral sensitizing dye (2)

-continued

Composition of a coating solution for an emulsion layer

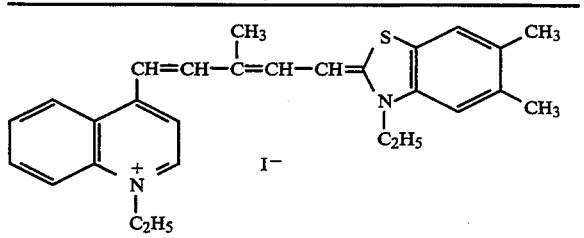

Supersensitizer (3)

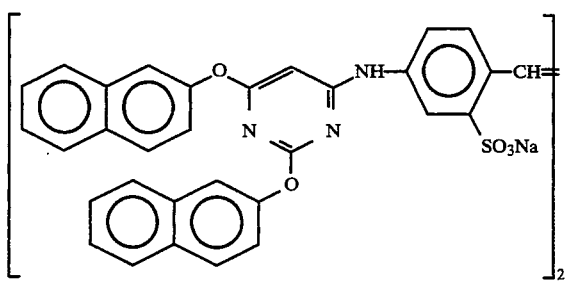

Storage life improving agent (4)

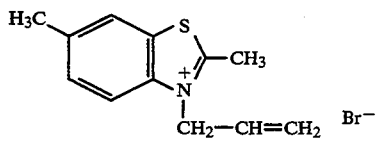

(3. Preparation of coating solution for surface protective layer)

In a container warmed at 40° C., a coating solution for forming a surface protective layer having the following composition was prepared.

| Composition of a coating solution for a surface protective layer | |
|---|---|
| a. Gelatin | 100 g |
| b. Polyacrylamide (molecular weight: 40,000) | 12 g |
| c. Polystyrenesulfonic acid soda (molecular weight: 600,000) | 0.6 g |
| d. N,N'-Ethylenebis(vinylsulfonacetamide) | 2.2 g |
| e. Fine grains of polymethylmethacrylate (mean grain size: 2.0 μm) | 2.7 g |
| f. Sodium t-octylphenoxyethoxyethanesulfonate | 1.8 g |
| g. $C_{16}H_{33}O-(CH_2CH_2O)_{10}-H$ | 4.0 g |
| h. Polyacrylic acid soda | 6.0 g |
| i. $C_8F_{17}SO_3K$ | 70 mg |
| j. $C_8F_{17}SO_2N(C_3H_7)(CH_2CH_2O)_4(CH_2)_4-SO_3Na$ | 70 mg |
| k. NaOH (1N) | 6 ml |
| l. Methanol | 90 ml |
| m. Compound (5) | 0.06 g |

Compound (5):

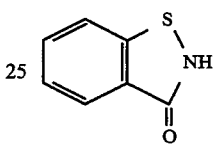

(4. Preparation of coating solution for back layer)

In a container warmed at 40° C., a coating solution for forming a back layer having the following composition was prepared.

| Composition of a coating solution for a back layer | |
|---|---|
| a. Gelatin | 100 g |
| b. Dye (1) | 4.2 g |
| c. Polystyrenesulfonic acid soda | 1.2 g |
| d. Latex of poly(ethyl acrylate/methacrylic acid) | 5 g |
| e. N,N'-Ethylenebis(vinylsulfonacetamide) | 4.8 g |
| f. compound (5) | 0.06 g |
| g. Dye (2) | 0.3 g |
| h. Dye (3) | 0.05 g |

Dye (1)

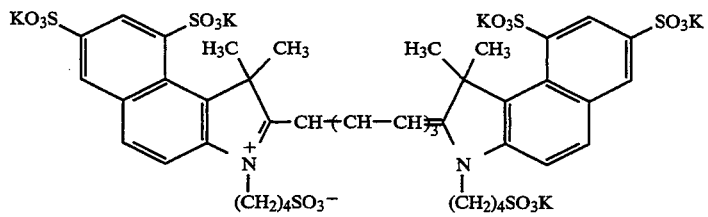

Dye (2)

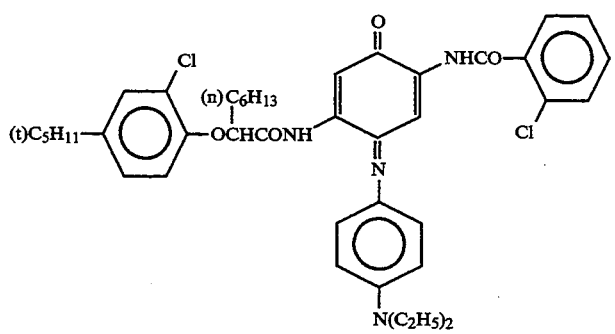

-continued

| Composition of a coating solution for a back layer |
|---|

Dye (3)

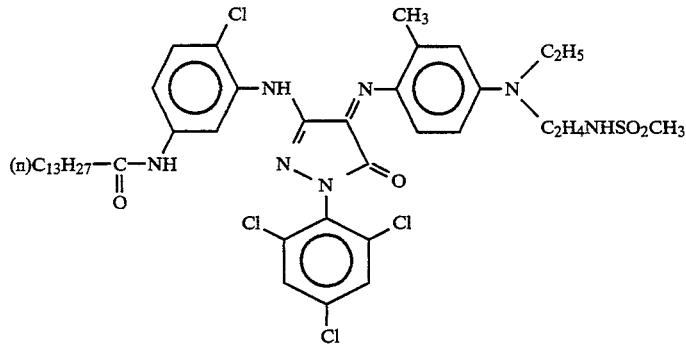

(5. preparation of coating solution for back surface protective layer)

In a container warmed at 40° C., a coating solution for forming a back surface protective layer having the following composition was prepared.

| Composition of a coating solution for a back surface protective layer | |
|---|---|
| a. Gelatin | 100 g |
| b. Polystyrenesulfonic acid soda | 0.5 g |
| c. N,N'-Ethylenebis(vinylsulfonacetamide) | 1.9 g |
| d. Fine grains of polymethylmethacrylate (mean grain size: 4.0 μm) | 4 g |
| e. Sodium t-octylphenoxyethoxyethanesulfonate | 2.0 g |
| f. NaOH (1N) | 6 ml |
| g. Polyacrylic acid soda | 2.4 g |
| h. $C_6H_{33}O$—$(CH_2CH_2O)_{10}$—H | 4.0 g |
| i. $C_8F_{17}SO_3K$ | 70 mg |
| j. $C_8F_{17}SO_2N(C_3H_7)(CH_2CH_2O)_4(CH_2)_4$—$SO_3Na$ | 70 mg |
| k. Methanol | 150 ml |
| l. Compound (5) | 0.06 g |

(6. Preparation of photographic material)

The coating solution for a back layer and the coating solution for a back surface protective layer prepared as above were applied onto one surface of a polyethylene terephthalate support in such amount that the amount of gelatin would be 3 g/m². Onto the other surface of the support were applied the coating solution for an emulsion layer and the coating solution for a surface protective layer prepared as above in such amounts that the amount of Ag would be 2.5 g/m² and the amount of gelatin on the resulting surface protective layer would be 1 g/m², to prepare a photographic material 1.

The above procedure was repeated except for using the dye (M-15) according to the invention and the dye (M-16) according to the invention, respectively, instead of the dye (1), to prepare photographic materials 2 and 3.

(7. Evaluation on storage stability)

Each of the photographic materials (light-sensitive materials shown in Table 5) prepared as above was allowed to stand for 3 days at 70% RH and a temperature of 50° C., and was measured on the reflection spectrum. From the reflection spectrum, a change of absorptivity at the absorption maximum wavelength of each dye (absorptivity after allowing the material to stand at 50° C. and 70% RH/absorptivity before allowing the material to stand at 50° C. and 70% RH) was determined. The results are set forth in Table 5.

(8. Evaluation on decoloring properties)

Each of the light-sensitive materials shown in Table. 5 was subjected to the following image formation process, and a reflection spectrum of a white portion on the obtained image was measured. The absorptivity of absorption maximum of each dye before the image formation and that after the image formation were compared with each other, to determine a color remaining ratio. The results are set forth in Table 5.

Image formation process

Each of the photographic materials 1 to 3 was allowed to stand for 7 days at 25° C. and 60% RH, then subjected to scanning exposure for $10^{-7}$ seconds at room temperature using a semiconductor laser of 780 nm, and was further subjected to developing process using the following developing solution (1) and the following fixing solution (1). The periods for developing, fixing, washing, hydro-extraction and drying were 7 seconds, 7 seconds, 4 seconds, 11 seconds and 11 seconds, respectively.

| (Composition of developing solution (1)) | |
|---|---|
| Potassium hydroxide | 29 g |
| Sodium sulfite | 31 g |
| Potassium sulfite | 44 g |
| Ethyelnetriaminetetraacetic acid | 1.7 g |
| Boric acid | 1 g |
| Hydroquinone | 30 g |
| Diethylene glycol | 29 g |
| 1-Phenyl-3-pyrazolidone | 1.5 g |
| Glutaraldehyde | 4.9 g |
| 5-Methylbenzotriazole | 60 mg |
| 5-Nitroindazole | 0.25 g |
| Potassium bormide | 7.9 g |
| Acetic acid | 18 g |
| Water to make up to | 1,000 ml |
| pH | 10.3 |
| (Composition of fixing solution (1)) | |
| Ammonium thiosulfate | 140 g |
| Sodium sulfite | 15 g |
| Disodium ethylenediaminetetraacetate dihydrate | 20 mg |
| Sodium hydroxide | 7 g |
| Aluminum sulfate | 10 g |
| Boric acid | 10 g |
| Sulfuric acid | 3.9 g |
| Acetic acid | 15 g |
| Water to make up to | 1,000 ml |
| pH | 4.30 |

The results are set forth in Table 5

TABLE 5

| Light-sensitive material | Dye | Dye remaining ratio (%) | Color remaining ratio (%) | Remark |
|---|---|---|---|---|
| 1 | Dye (1) | 92 | 6 | for comparison |
| 2 | M-15 | 94 | 3 | present invention |
| 3 | M-16 | 95 | 2 | present invention |

As is evident from the results set forth in Table 5, the dyes according to the invention were effective for stability and color remaining. In more detail, the light-sensitive materials of the invention were excellent in storage stability because the dyes were hardly decomposed or decolored, and the light-sensitive materials of the invention provided images of reduced residual color after the image formation.

We claim:

1. A silver halide photographic light-sensitive material comprising an emulsion layer containing a methine compound represented by the following formula (III):

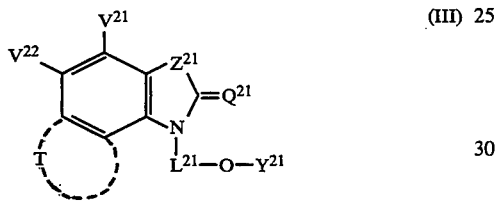

(III)

wherein each of $V^{21}$ and $V^{22}$ independently represents a hydrogen atom, an alkyl group, an alkyl group which is substituted with carboxyl, sulfo or halogen, a halogen atom, an acyl group, an acyloxy group, an alkoxycarbonyl group, a carbamoyl group, a sulfamoyl group, a sulfo group, a carboxy group, a cyano group, a hydroxyl group, an amino group, an acylamino group, an alkoxy group, an aryloxy group, an alkylthio group, an arylthio group, a sulfonamide group, a ureido group, an alkylsulfonyl group, an arylsulfonyl group, an aryl group, an aryl group which is substituted with halogen or methyl, or a heterocyclic group;

$Z^{21}$ represents —O—, —S—, —NR$^{22}$— in which $R^{22}$ represents a halogen atom, a hydrogen atom, an alkyl group, an alkyl group which is substituted with carboxyl, sulfo, halogen, hydroxyl, acetyl, methylthio, methoxy, methanesulfonamino, acetylamino or methanesulfonylcarbamoyl, an aryl group, an aryl group which is substituted with carboxyl, sulfo, cyano, nitro, hydroxyl, halogen, alkyl, alkoxy, aryloxy, acyloxy, acyl, sulfamoyl, carbamoyl or aryl, or a heterocyclic group, —CR$^{23}$R$^{24}$— in which each of $R^{23}$ and $R^{24}$ independently represents a hydrogen atom, an alkyl group or an alkyl group which is substituted with carboxyl, sulfo, halogen, hydroxyl, acetyl, methylthio, methoxy, methanesulfonamino, acetylamino or methanesulfonylcarbamoyl, or —CV$^{23}$=CV$^{24}$— in which each of $V^{23}$ and $V^{24}$ independently represents a hydrogen atom, an alkyl group, an alkyl group which is substituted with carboxyl, sulfo or halogen, a halogen atom, an acyl group, an acyloxy group, an alkoxycarbonyl group, a carbamoyl group, a sulfamoyl group, a sulfo group, a carboxy group, a cyano group, a hydroxyl group, an amino group, an acylamino group, an alkoxy group, an aryloxy group, an alkylthio group, an arylthio group, a sulfonamide group, a ureido group, an alkylsulfonyl group, an arylsulfonyl group, an aryl group, an aryl group which is substituted with halogen or methyl, or a heterocyclic group;

T represents a group of atoms to form an aromatic ring, an aliphatic ring or a heterocyclic ring together with the hydrocarbon moiety of the benzene ring to which T is bonded;

$L^{21}$ represents an ethylene group; a propylene group; an ethylene group which is substituted with a hydroxyl group, a sulfo group, a carboxyl group, an alkyl group, an alkoxy group, an aryloxy group, an alkylthio group, an acyloxy group, an acyl group, a sulfamoyl group, an aryl group or a heterocyclic group; or a propylene group which is substituted with a hydroxyl group, a sulfo group, a carboxyl group, an alkyl group, an alkoxy group, an aryloxy group, an alkylthio group, an acyloxy group, an acyl group, a sulfamoyl group, an aryl group or a heterocyclic group;

$Y^{21}$ represents a group that is cleavable at a portion bonding to —O—; and $Q^{21}$ represents a methine group or a polymethine group which is terminated by a heterocyclic group.

2. The silver halide photographic light-sensitive material as defined in claim 1, wherein $Y^{21}$ is acetyl, an ethoxycarbonyl group, an ethylcarbamoyl group or a dimethylsulfamoyl group;

$Z^{21}$ is —S—, —Se— or —NR$^{22}$— in which $R^{22}$ is methyl, ethyl or phenyl;

$L^{21}$ is an ethylene group;

$V^{21}$ and $V^{22}$ are each hydrogen, methyl, methoxy, methylthio or halogen; and T represents a group to form a benzene ring together with a hydrocarbon moiety of the benzene ring to which T is bonded.

* * * * *